(12) United States Patent
Jones et al.

(10) Patent No.: US 7,125,865 B2
(45) Date of Patent: Oct. 24, 2006

(54) THERAPEUTIC COMPOUNDS FOR TREATING DYSLIPIDEMIC CONDITIONS

(75) Inventors: A. Brian Jones, Walden (GB); Alan D. Adams, Cranford, NJ (US); Ahren I. Green, Green Brook, NJ (US); Shaei Y. Huang, Jeffersonville, PA (US); Bruno Tse, Philadelphia, PA (US); Clare E. Gutteridge, Annapolis, MD (US); Yuan Cheng, Newbury Park, CA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/522,114

(22) PCT Filed: Jul. 21, 2003

(86) PCT No.: PCT/US03/22807

§ 371 (c)(1),
(2), (4) Date: Jan. 24, 2005

(87) PCT Pub. No.: WO2004/011448

PCT Pub. Date: Feb. 5, 2004

(65) Prior Publication Data

US 2005/0239769 A1    Oct. 27, 2005

Related U.S. Application Data

(60) Provisional application No. 60/398,716, filed on Jul. 25, 2002.

(51) Int. Cl.
C07D 277/04 (2006.01)
C07D 277/12 (2006.01)
C07D 261/20 (2006.01)
C07D 421/00 (2006.01)
C07D 241/00 (2006.01)

(52) U.S. Cl. ............... 514/212.08; 514/230.8; 514/241; 514/254.02; 514/255.05; 514/256; 514/269; 514/274; 514/338; 514/369; 514/379; 540/524; 544/137; 544/220; 544/310; 544/331; 544/368; 544/405; 546/272.1; 548/183; 548/241

(58) Field of Classification Search ............... 540/524; 544/137, 220, 310, 331, 368, 405; 548/183, 548/241; 546/272.1; 514/212.08, 230.8, 514/241, 254.02, 255.05, 256, 269, 274, 514/338, 369, 379
See application file for complete search history.

(56) References Cited

U.S. PATENT DOCUMENTS

| 6,008,237 A * | 12/1999 | Sahoo et al. ............... 514/369 |
| 6,908,934 B1 | 6/2005 | Adams et al. |
| 2002/0173663 A1 | 11/2002 | Liu et al. |
| 2003/0086923 A1 | 5/2003 | Sparrow et al. |
| 2003/0125357 A1 | 7/2003 | Adams et al. |

FOREIGN PATENT DOCUMENTS

| WO | WO 01/41704 | 6/2001 |
| WO | WO 03/045382 | 6/2003 |
| WO | WO 03/053352 | 7/2003 |

OTHER PUBLICATIONS

Menke, et al., Endocrinology, "A Novel Liver X Receptor Agonist Establishes Species Differences in the Regulation of Cholesterol 7alpha-Hydroxylase (CYP7a)", 143(7) pp. 2548-2558, Jul. 2002.

* cited by examiner

*Primary Examiner*—Bruck Kifle
(74) *Attorney, Agent, or Firm*—Carol S. Quagliato; Melvin Winckur

(57) ABSTRACT

The present invention relates to novel LXR ligands of Formula I and the pharmaceutically acceptable salts, esters and tautomers thereof, which are useful in the treatment of dyslipidemic conditions, particularly depressed levels of HDL cholesterol.

(I)

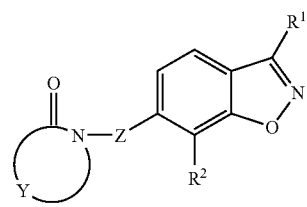

19 Claims, No Drawings

THERAPEUTIC COMPOUNDS FOR TREATING DYSLIPIDEMIC CONDITIONS

CROSS REFERENCE TO RELATED APPLICATIONS

This application is a 35 U.S.C. § 371 filing from International Application No. PCT/US03/22807, filed Jul. 21, 2003, which claims the benefit under 35 U.S.C. 119(e) of U.S. Provisional Application No. 60/398,716, filed Jul. 25, 2002.

BACKGROUND OF THE INVENTION

Recent publications in Nature Genetics, August, 1999 (Young et al., page 316; Bodzioch et al., page 347; Brooks-Wilson et al., page 335, and Rust et al., page 352) showed that humans with mutations in the gene ABCA1 (also previously known in the art as ABC1) have low levels of high density lipoprotein (HDL). Low HDL levels are a risk factor for atherosclerosis, myocardial infarction and related conditions such as ischemic stroke. Therefore, increasing the expression of the ABCA1 gene would be expected to increase HDL levels and decrease the occurrence of atherosclerosis, myocardial infarction and related conditions such as ischemic stroke. It has been reported that expression of the ABCA1 gene is increased by cholesterol loading of cells (Langmann et al., *Biochem. Biophys. Res. Comm.*, 257, 29–33 (1999)). LXRα is a nuclear receptor that is required for the induction of cholesterol 7α-hydroxylase in mouse liver following cholesterol feeding (Peet et al., *Cell*, 93, 693–704 (1998)). LXRα and LXRβ are activated by 22-(R)-hydroxycholesterol and other oxysterols (Janowski et al. *Proc. Natl. Acad. Sci USA*, 96, 266–271 (1999), Thomas A. Spencer et al. *J. Med. Chem.*, 44, 886–897, (2001)). Some non-steroidal small molecule agonists of LYRα and LXRβ have been reported to affect circulating HDL levels, cholesterol absorption, reverse cholesterol transport and ABCA1 expression in vivo (J. R. Schultz, et al. *Genes & Devel.* 14, 2831–2838, (2000), J. J. Repa et al. *Science*, 289, 1524–1529, (2000)). It has been found that LXRα and/or LXRβ cause the induction or regulation of ABCA1 expression, and that small molecule ligands of LXR are useful as drugs to increase the expression of ABCA1, increase levels of HDL and thereby decrease the risk of atherosclerosis, myocardial infarction and related conditions such as peripheral vascular disease and ischemic stroke.

The various dyslipidemic conditions, which are risk factors for atherosclerosis, are currently treated with several different classes of drugs, such as statins which are HMG-CoA reductase inhibitors, bile acid sequestrants (e.g., cholestyramine and colestipol), nicotinic acid (niacin), and fibrates. However, except for niacin, most of these treatments do not raise HDL as their primary effect. With favorable outcomes in many human studies, the statin class of drugs is used to modulate LDL and, to a lesser extent, HDL and triglycerides. Conditions principally characterized by elevated plasma triglycerides and low HDL are frequently treated with drugs belonging to the fibrate class. The fibrates are PPAR alpha agonists that lower triglycerides and raise HDL in many instances. There are no currently marketed drugs whose principal actions are mediated by LXR.

We have now discovered a new class of small molecules which are LXR ligands, i.e., LXRα and/or LXRβ ligands, and are therefore expected to be useful for modulation of HDL levels, ABCA1 gene expression and reverse cholesterol transport. The instant compounds have been shown to raise plasma levels of HDL in animal models and to increase cholesterol efflux from cells in vitro. These biological activities are critical for reverse cholesterol transport.

The novel compounds of this invention are intended as a treatment for dyslipidemias, especially low plasma HDL cholesterol levels, as well as for treatment and/or prevention of lipid accumulation in atherosclerotic plaques, which is an underlying cause or aggravating factor in atherosclerosis.

SUMMARY OF THE INVENTION

Compounds of Formula I are novel LXR ligands and are useful in the treatment of dyslipidemic conditions including below-desirable levels of HDL cholesterol.

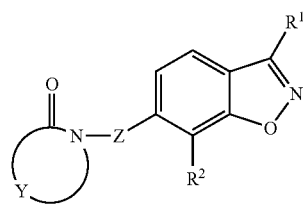

One object of the instant invention is to provide a method for treating depressed plasma HDL cholesterol levels comprising administering a therapeutically effective amount of a compound of Formula I to a patient in need of such treatment.

Another object is to provide a method for preventing or treating dyslipidemic conditions comprising administering a prophylactically or therapeutically effective amount, as appropriate, of a compound of Formula I to a patient in need of such treatment.

As a further object, methods are provided for preventing or reducing the risk of developing atherosclerosis, as well as for halting or slowing the progression of atherosclerotic disease once it has become clinically evident, comprising the administration of a prophylactically or therapeutically effective amount, as appropriate, of a compound of Formula I to a patient who is at risk of developing atherosclerosis or who already has atherosclerotic disease. The method of this invention also serves to remove cholesterol from tissue deposits such as xanthomas and atherosclerotic lesions by hastening the efflux of cholesterol from cells in those lesions.

Another object of the present invention is the use of the compounds of the present invention for the manufacture of a medicament useful in treating, preventing or reducing the risk of developing these conditions.

Other objects of this invention are to provide processes for making the compounds of Formula I and to provide novel pharmaceutical compositions comprising these compounds. Additional objects will be evident from the following detailed description.

DETAILED DESCRIPTION OF THE INVENTION

The novel LXR ligands of the instant invention are compounds of Formula I

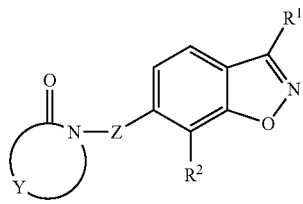

I and the pharmaceutically acceptable salts, esters and tautomers thereof, wherein $R^1$ is selected from the group consisting of:
(a) —$CF_3$,
(b) —$CH_2C(CH_3)_3$,
(c) phenyl, unsubstituted, mono- or poly-substituted with halo,
(d) —$C_{1-6}$alkyl, and
(e) —$C_{1-2}$alkyl-phenyl;

$R^2$ is selected from the group consisting of:
(a) —$C_{1-6}$alkyl,
(b) —$COOR^3$,
(c) —$CR^3R^4$—O—$R^5$,
(d) —$CR^3R^4$—S—$R^5$, and
(e) —$COR^3$;

$R^3$, $R^4$ and $R^5$ are independently selected at each occurrence from the group consisting of —H, phenyl, and $C_{1-6}$alkyl;

Y is joined together with the nitrogen and the carbonyl carbon shown in Formula I to which Y is respectively attached, to form a heterocyclic ring selected from:

(a) a 5-membered heterocyclic ring selected from the group consisting of:

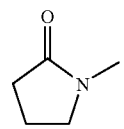
(i)

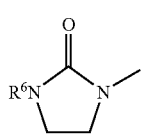
(ii)

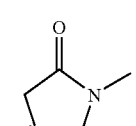
(iii)

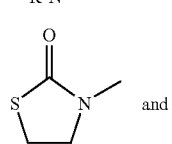 and
(iv)

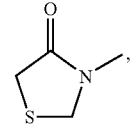
(v)

(b) a 6-membered heterocyclic ring selected from the group consisting of:

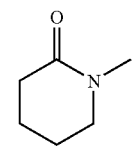
(i)

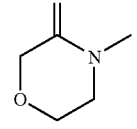
(ii)

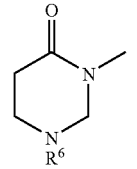
(iii)

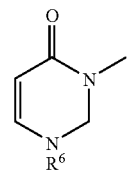
(iv)

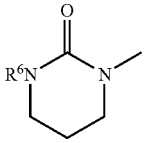
(v)

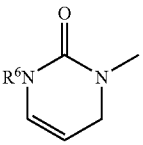
(vi)

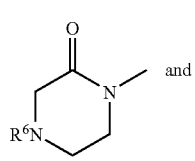 and
(vii)

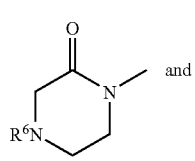
(viii)

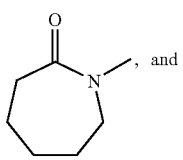, and (d) a bicyclic heterocyclic ring selected from the group consisting of:

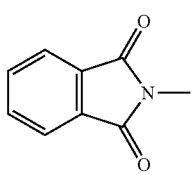

(i)

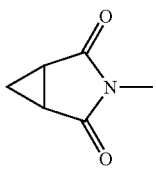

(ii)

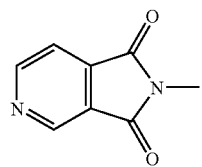

(iii)

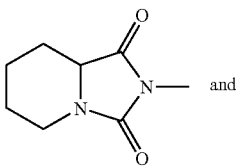 and (iv)

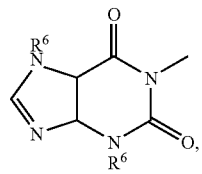

(v)

wherein each carbon atom in the heterocyclic ring, formed when Y is joined together with the nitrogen and the carbonyl carbon shown in Formula I, is independently unsubstituted, mono- or di-substituted with a substituent independently selected at each occurrence from $R^7$;

$R^6$ is independently selected at each occurrence from the group consisting of:
(a) —H,
(b) —$C_{1-6}$alkyl, unsubstituted, mono- or poly-substituted with a substituent selected from the group consisting of halo, —OH, —$NR^3R^4$, —$OR^3$, —$COOR^3$, and —CN,
(c) —$C_{1-6}$alkyl-phenyl, unsubstituted, mono- or poly-substituted with a substituent selected from the group consisting of halo, —$C_{1-3}$alkyl, and —$COOR^3$,
(d) —$C_{3-6}$cycloalkyl, unsubstituted, mono- or poly-substituted with a substituent selected from the group consisting of halo, —OH, —$OR^3$, —$COOR^3$, and —CN,
(e) —$C_{3-6}$cycloheteroalkyl, unsubstituted, mono- or poly-substituted with a substituent selected from the group consisting of halo, —OH, —$(CH_2)_nOR^3$, —$OR^3$, —$COOR^3$, and —CN, wherein n is an integer selected from 2, 3, 4, 5 and 6,
(f) —$C_{2-6}$alkenyl,
(g) —$C(O)C_{1-6}$alkyl,
(h) —$COOR^3$,
(i) —$C(O)$—$(CH_2)_p$—$COOR^3$, wherein p is an integer selected from 2, 3 and 4,
(j) phenyl, unsubstituted, mono- or poly-substituted with a substituent selected from the group consisting of halo, —$C_{1-3}$alkyl, and —$COOR^3$,
(k) pyridyl, unsubstituted, mono- or poly-substituted with a substituent selected from the group consisting of halo, —$C_{1-3}$alkyl, and —$COOR^3$,
(l) pyrimidinyl, unsubstituted, mono- or poly-substituted with a substituent selected from the group consisting of halo, —$C_{1-3}$alkyl, and —$COOR^3$,
(m) pyrazinyl, unsubstituted, mono- or poly-substituted with a substituent selected from the group consisting of halo, —$C_{1-3}$alkyl, and —$COOR^3$, and
(n) thiazolyl, unsubstituted, mono- or poly-substituted with a substituent selected from the group consisting of halo, —$C_{1-3}$alkyl, and —$COOR^3$;

$R^7$ is independently selected at each occurrence from the group consisting of:
(a) =O,
(b) —$C_{1-6}$alkyl-phenyl, unsubstituted, mono- or poly-substituted with a substituent selected from the group consisting of halo, —CN, —$COOR^3$, —$COR^3$, and —OH,
(c) —$C_{1-6}$alkyl, unsubstituted, mono- or poly-substituted with a substituent selected from the group consisting of halo, —OH, —$COOR^3$, tetrazole and —CN,
(d) —$C_{3-6}$cycloalkyl,
(e) —$C_{3-6}$spiroalkyl,
(f) —$COOR^3$,
(g) halo,
(h) —$NR^3R^4$,
(i) phenyl, unsubstituted, mono- or poly-substituted with a substituent selected from the group consisting of halo, —$COOR^3$ and —$C_{1-4}$alkyl,
(j) pyridyl, unsubstituted, mono- or poly-substituted with a substituent selected from the group consisting of halo, —$C_{1-3}$alkyl, and —$COOR^3$,
(k) pyrimidinyl, unsubstituted, mono- or poly-substituted with a substituent selected from the group consisting of halo, —$C_3$alkyl, and —$COOR^3$, and
(l) pyrazinyl, unsubstituted, mono- or poly-substituted with a substituent selected from the group consisting of halo, —$C_3$alkyl, and —$COOR^3$; and Z is selected from the group consisting of:
(a) —$C_{1-6}$alkyl-,
(b) —$C_{1-6}$alkyl-O—,
(c) —$C_{3-6}$cycloalkyl-, and
(d) —$C_{3-6}$cycloalkyl-O—.

In one embodiment of the present invention are those compounds of Formula I wherein $R^1$ is selected from the group consisting of:

(a) —$CF_3$,
(b) —$CH_2C(CH_3)_3$, and
(c) phenyl, unsubstituted, mono- or poly-substituted with halo.

In a class of this embodiment are those compounds of Formula I wherein $R^1$ is selected from the group consisting of:

(a) —$CF_3$, and
(b) phenyl, unsubstituted, mono- or poly-substituted with halo.

In a subclass of this embodiment are those compounds of Formula I wherein $R^1$ is —$CF_3$.

In a second embodiment of the present invention are those compounds of Formula I wherein $R^2$ is selected from the group consisting of:

(a) —$C_{1-6}$alkyl, and
(b) —$COR^3$.

In a class of this embodiment are those compounds of Formula I wherein $R^2$ is —$C_{1-6}$alkyl.

In sub-class of this class are those compounds of Formula I wherein $R^2$ is n-propyl.

In third embodiment of this invention are those compounds of Formula I wherein Y is joined together with the nitrogen and the carbonyl carbon shown in Formula I to which Y is respectively attached, to form a heterocyclic ring selected from:

(a) a 5-membered heterocyclic ring selected from the group consisting of:

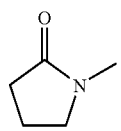
(i)

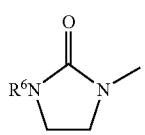
(ii)

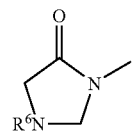
(iii)

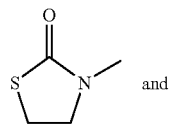
(iv)

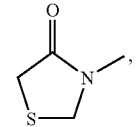
(v)

(b) a 6-membered heterocyclic ring selected from the group consisting of:

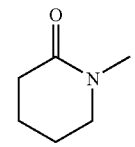
(i)

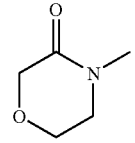
(ii)

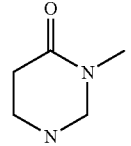
(iii)

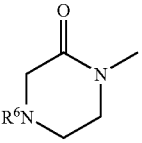
(iv)

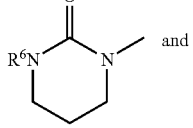
(v)
and

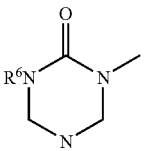
(vi)

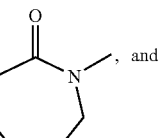
(c)
, and

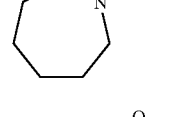
(d)

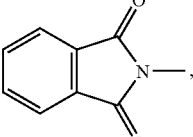

wherein each carbon atom in the heterocyclic ring, formed when Y is joined together with the nitrogen and the carbonyl carbon shown in Formula I, is independently unsubstituted, mono- or di-substituted with a substituent independently selected at each occurrence from $R^7$.

In a class of the third embodiment of this invention are those compounds of Formula I wherein Y is joined together with the nitrogen and the carbonyl carbon shown in Formula I to which Y is respectively attached, to form a heterocyclic ring selected from:

(a) a 5-membered heterocyclic ring selected from the group consisting of:

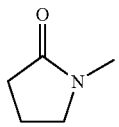
(i)

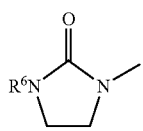
(ii)

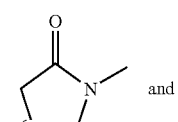
and
(iii)

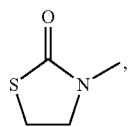
(iv)

(b) a 6-membered heterocyclic ring selected from the group consisting of:

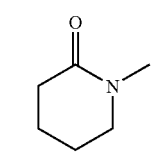
(i)

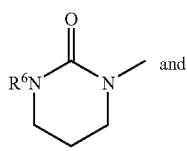
and
(ii)

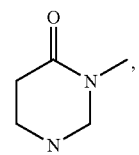
(iii)

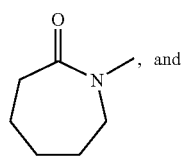
, and
(c)

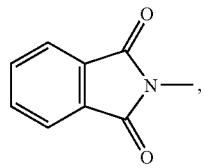
(d)

wherein each carbon atom in the heterocyclic ring, formed when Y is joined together with the nitrogen and the carbonyl carbon shown in Formula I, is independently unsubstituted, mono- or di-substituted with a substituent independently selected at each occurrence from $R^7$.

In a subclass of this class are those compounds of Formula I wherein Y is joined together with the nitrogen and the carbonyl carbon shown in Formula I to which Y is respectively attached, to form a heterocyclic ring selected from:

(a) a 5-membered heterocyclic ring selected from the group consisting of:

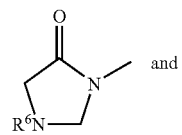
and
(i)

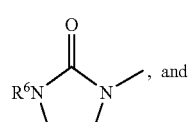
, and
(ii)

(b) a 6-membered heterocyclic ring selected from the group consisting of:

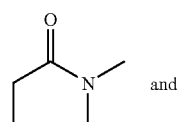
and
(i)

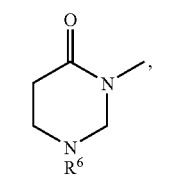
,
(ii)

wherein each carbon atom in the heterocyclic ring, formed when Y is joined together with the nitrogen and the carbonyl carbon shown in Formula I, is independently unsubstituted, mono- or di-substituted with a substituent independently selected at each occurrence from $R^7$.

In a fourth embodiment of this invention are those compounds of Formula I wherein $R^6$ is independently selected at each occurrence from the group consisting of:

(a) —H,
(b) —C$_{1-6}$alkyl, unsubstituted, mono- or poly-substituted with a substituent selected from the group consisting of halo, —OH, —NR$^3$R$^4$, —OR$^3$, —COOR$^3$, and —CN,
(c) —C$_{1-6}$alkyl-phenyl, unsubstituted, mono- or poly-substituted with a substituent selected from the group consisting of halo, —C$_{1-3}$alkyl, and —COOR$^3$,
(d) —C(O)—(CH$_2$)$_p$—COOR$^3$, wherein p is an integer selected from 2, 3 and 4,
(e) phenyl, unsubstituted, mono- or poly-substituted with a substituent selected from the group consisting of halo, —C$_{1-3}$alkyl, and —COOR$^3$,
(f) pyridyl, unsubstituted, mono- or poly-substituted with a substituent selected from the group consisting of halo, —C$_{1-3}$alkyl, and —COOR$^3$, and
(g) pyrimidinyl, unsubstituted, mono- or poly-substituted with a substituent selected from the group consisting of halo, —C$_{1-3}$alkyl, and —COOR$^3$.

In a fifth embodiment of this invention are those compounds of Formula I wherein R$^7$ is independently selected at each occurrence from the group consisting of:
(a) =O,
(b) —CH$_2$-phenyl, unsubstituted, mono- or poly-substituted with a substituent selected from the group consisting of halo, —CN, —COOR$^3$, —COR$^3$ and —OH,
(c) —C$_{1-6}$alkyl, unsubstituted, mono- or poly-substituted with a substituent selected from the group consisting of halo, —OH, —COOR$^3$, tetrazole and —CN,
(d) halo,
(e) —NH$_2$,
(f) phenyl, unsubstituted, mono- or poly-substituted with a substituent selected from the group consisting of halo, —COOR$^3$ and —C$_{1-4}$alkyl,
(g) pyridyl, unsubstituted, mono- or poly-substituted with a substituent selected from the group consisting of halo, —C$_{1-3}$alkyl, and —COOR$^3$,
(h) pyrimidinyl, unsubstituted, mono- or poly-substituted with a substituent selected from the group consisting of halo, —C$_{1-3}$alkyl, and —COOR$^3$, and
(i) pyrazinyl, unsubstituted, mono- or poly-substituted with a substituent selected from the group consisting of halo, —C$_{1-3}$alkyl, and —COOR$^3$.

In a class of the fifth embodiment are those compounds of Formula I wherein R$^7$ is independently selected at each occurrence from the group consisting of:
(a) =O,
(b) —CH$_2$-phenyl, unsubstituted, mono- or poly-substituted with a substituent selected from the group consisting of halo, —CN, —COOR$^3$, —COR$^3$, and —OH,
(c) —C$_{1-6}$alkyl, unsubstituted, mono- or poly-substituted with a substituent selected from the group consisting of halo, —OH, —COOR$^3$, tetrazole and —CN,
(d) halo,
(e) —NH$_2$,
(f) phenyl, unsubstituted, mono- or poly-substituted with a substituent selected from the group consisting of halo, —COOR$^3$ and —C$_{1-4}$alkyl, and
(g) pyridyl, unsubstituted, mono- or poly-substituted with a substituent selected from the group consisting of halo, —C$_{1-3}$alkyl, and —COOR$^3$.

In a sixth embodiment of the present invention are compounds of Formula I wherein Z is —C$_{2-4}$alkyl-O—.

In one class of the sixth embodiment are those compounds of Formula I wherein R$^1$ is selected from the group consisting of —CF$_3$, —CH$_2$C(CH$_3$)$_3$, and phenyl unsubstituted, mono- or poly-substituted with halo; R$^2$ is selected from the group consisting of —C$_{1-6}$alkyl and —COR$^3$; and R$^3$, R$^4$ and R$^5$ are independently selected at each occurrence from the group consisting of —H, phenyl, —CH$_2$-phenyl, and —C$_{1-6}$alkyl. Within this class, R$^2$ is particularly —C$_{1-6}$alkyl, and more particularly R$^2$ is n-propyl.

In sub-class (i) of this class of the sixth embodiment are compounds wherein R$^2$ is n-propyl, and Y is joined together with the nitrogen and the carbonyl carbon shown in Formula I to which Y is respectively attached, to form a heterocyclic ring selected from:
(a) a 5-membered heterocyclic ring selected from the group consisting of:

(i)

(ii)

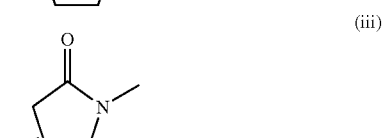

(iii)

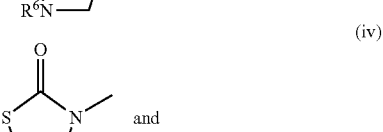

and (iv)

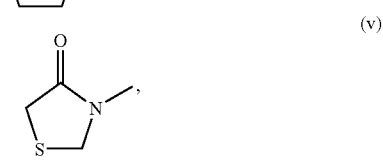

(v)

(b) a 6-membered heterocyclic ring selected from the group consisting of:

(i)

(ii)

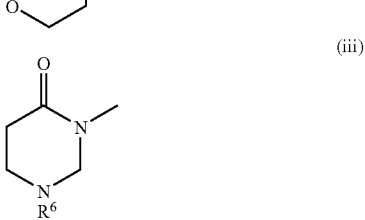

(iii)

-continued

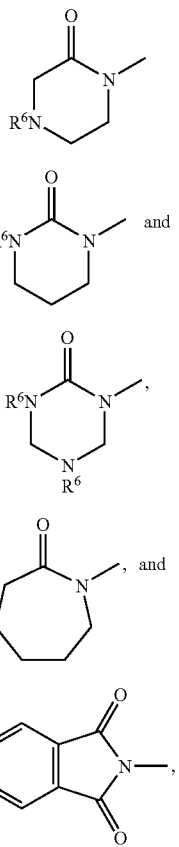

(iv)

(v) and (vi)

(c) and (d)

wherein each carbon atom in the heterocyclic ring, formed when Y is joined together with the nitrogen and the carbonyl carbon shown in Formula I, is independently unsubstituted, mono- or di-substituted with a substituent independently selected at each occurrence from R⁷.

Particularly in sub-class (i) of this class are compounds of Formula I wherein R⁶ is independently selected at each occurrence from the group consisting of:
 (a) —H,
 (b) —C$_{1-6}$alkyl, unsubstituted, mono- or poly-substituted with a substituent selected from the group consisting of halo, —OH, —NR³R⁴, —OR³, —COOR³, and —CN,
 (c) —C$_{1-6}$alkyl-phenyl, unsubstituted, mono- or poly-substituted with a substituent selected from the group consisting of halo, —C$_{1-3}$alkyl, and —COOR³,
 (d) —C(O)—(CH$_2$)$_p$—COOR³, wherein p is an integer selected from 2, 3 and 4,
 (e) phenyl, unsubstituted, mono- or poly-substituted with a substituent selected from the group consisting of halo, —C$_{1-3}$alkyl, and —COOR³,
 (f) pyridyl, unsubstituted, mono- or poly-substituted with a substituent selected from the group consisting of halo, —C$_{1-3}$alkyl, and —COOR³, and
 (g) pyrimidinyl, unsubstituted, mono- or poly-substituted with a substituent selected from the group consisting of halo, —C$_{1-3}$alkyl, and —COOR³.

More particularly, in sub-class (i) of this class are compounds wherein R⁷ is independently selected at each occurrence from the group consisting of:
 (a) =O,
 (b) —CH$_2$-phenyl, unsubstituted, mono- or poly-substituted with a substituent selected from the group consisting of halo, —CN, —COOR³, —COR³ and —OH,
 (c) —C$_{1-6}$alkyl, unsubstituted, mono- or poly-substituted with a substituent selected from the group consisting of halo, —OH, —COOR³, tetrazole and —CN,
 (d) halo,
 (e) —NH$_2$,
 (f) phenyl, unsubstituted, mono- or poly-substituted with a substituent selected from the group consisting of halo, —COOR³, and —C$_{1-4}$alkyl, and
 (g) pyridyl, unsubstituted, mono- or poly-substituted with a substituent selected from the group consisting of halo, —C$_{1-3}$alkyl, and —COOR³.

In sub-class (ii) of the this class of the sixth embodiment are compounds wherein R¹ is selected from the group consisting of —CF$_3$, and phenyl, unsubstituted, mono- or poly-substituted with halo, and R² is n-propyl.

Particularly, in sub-class (ii) of this class are compounds wherein Y is joined together with the nitrogen and the carbonyl carbon shown in Formula I to which Y is respectively attached, to form a heterocyclic ring selected from:
 (a) a 5-membered heterocyclic ring selected from the group consisting of:

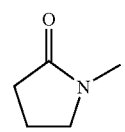

(i)

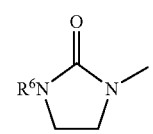

(ii)

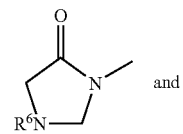

(iii) and

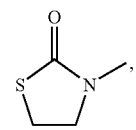

(iv)

(b) a 6-membered heterocyclic ring selected from the group consisting of:

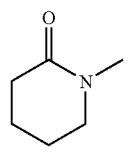

(i)

-continued

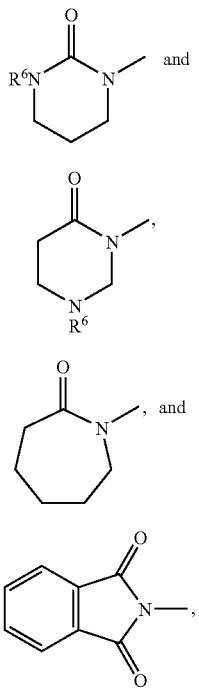

wherein each carbon atom in the heterocyclic ring, formed when Y is joined together with the nitrogen and the carbonyl carbon shown in Formula I, is independently unsubstituted, mono- or di-substituted with a substituent independently selected at each occurrence from $R^7$.

Specific compounds within sub-class (ii) of this class are:
(1) 1-(3-{[7-propyl-3-(trifluoromethyl)-1,2-benzisoxazol-6-yl]oxy}propyl)imidazolidin-2-one,
(2) 1-(3-{[7-propyl-3-(trifluoromethyl)-1,2-benzisoxazol-6-yl]oxy}propyl)pyrrolidine-2,5-dione,
(3) 3-(3-{[7-propyl-3-(trifluoromethyl)-1,2-benzisoxazol-6-yl]oxy}propyl)thiazolidine-2,4-dione,
(4) 3-(3-{[7-propyl-3-(trifluoromethyl)-1,2-benzisoxazol-6-yl]oxy}propyl)imidazolidine-2,4-dione,
(5) 1-methyl-3-(3-{[7-propyl-3-(trifluoromethyl)-1,2-benzisoxazol-6-yl]oxy}propyl)imidazolidine-2,4-dione,
(6) 5,5-dimethyl-3-(3-{[7-propyl-3-(trifluoromethyl)-1,2-benzisoxazol-6-yl]oxy}propyl)imidazolidine-2,4-dione,
(7) 1-(2-pyridyl)-3-(3-{[7-propyl-3-(trifluoromethyl)-1,2-benzisoxazol-6-yl]oxy}propyl)imidazolidine-2,4-dione,
(8) 3-(3-{[7-propyl-3-(trifluoromethyl)-1,2-benzisoxazol-6-yl]oxy}propyl)-1-pyrazin-2-ylimidazolidine-2,4-dione,
(9) rac-5-methyl-5-phenyl-3-(3-{[7-propyl-3-(trifluoromethyl)-1,2-benzisoxazol-6-yl]oxy}propyl)imidazolidine-2,4-dione,
(10) rac-5-methyl-5-phenyl-3-(3-{[7-propyl-3-(trifluoromethyl)-1,2-benzisoxazol-6-yl]oxy}butyl)imidazolidine-2,4-dione,
(11) rac-5-methyl-5-phenyl-3-(3-{[7-propyl-3-(phenyl)-1,2-benzisoxazol-6-yl]oxy}propyl)imidazolidine-2,4-dione,
(12) rac-5-methyl-5-(3-carboxyphenyl)-3-(3-{[7-propyl-3-(trifluoromethyl)-1,2-benzisoxazol-6-yl]oxy}propyl)imidazolidine-2,4-dione,
(13) rac-5-methyl-5-(2-pyridyl)-3-(3-{[7-propyl-3-(trifluoromethyl)-1,2-benzisoxazol-6-yl]oxy}propyl)imidazolidine-2,4-dione,
(14) rac-3-[2,5-dioxo-4-phenyl-1-(3-{[7-propyl-3-(trifluoromethyl)-1,2-benzisoxazol-6-yl]oxy}propyl)imidazolidin-4-yl]propanoic acid,
(15) 2-[2-oxo-3-(3-{[7-propyl-3-(trifluoromethyl)-1,2-benzisoxazol-6-yl]oxy}propyl)imidazolidin-1-yl]propanoic acid,
(16) 1-(3-{[7-propyl-3-(trifluoromethyl)-1,2-benzisoxazol-6-yl]oxy}propyl)piperidin-2-one,
(17) 1-(3-{[7-propyl-3-(trifluoromethyl)-1,2-benzisoxazol-6-yl]oxy}propyl)piperidin-2,6-dione,
(18) 1-(3-{[7-propyl-3-(phenyl)-1,2-benzisoxazol-6-yl]oxy}propyl)piperidin-2,5-dione,
(19) 3-(3-{[7-propyl-3-(phenyl)-1,2-benzisoxazol-6-yl]oxy}propyl)-dihydropyrimidine-2,4(1H,3H)-dione,
(20) 6-phenyl-3-(3-{[7-propyl-3-(trifluoromethyl)-1,2-benzisoxazol-6-yl]oxy}propyl)dihydropyrimidine-2,4(1H,3H)-dione,
(21) 1-phenyl-3-(3-{[7-propyl-3-(trifluoromethyl)-1,2-benzisoxazol-6-yl]oxy}propyl)dihydropyrimidine-2,4(1H,3H)-dione,
(22) 3-(3-{[7-propyl-3-(trifluoromethyl)-1,2-benzisoxazol-6-yl]oxy}propyl)-1-pyridin-2-yldihydropyrimidine-2,4(1H,3H)-dione,
(23) 3-(3-{[7-propyl-3-(trifluoromethyl)-1,2-benzisoxazol-6-yl]oxy}propyl)-5,6-dihydro-2H-1,2'-bipyrimidine-2,4(3H)-dione, and
(24) 1-(3-{[7-propyl-3-(trifluoromethyl)-1,2-benzisoxazol-6-yl]oxy}propyl)azepan-2-one, and pharmaceutically acceptable salts, esters and tautomers thereof.

In sub-class (iii) of this class of the sixth embodiment are compounds wherein $R^1$ is —$CF_3$ and $R^2$ is n-propyl.

Particularly, in sub-class (iii) of this class are compounds wherein Y is joined together with the nitrogen and the carbonyl carbon shown in Formula I to which Y is respectively attached, to form a heterocyclic ring selected from:
(a) a 5-membered heterocyclic ring selected from the group consisting of:

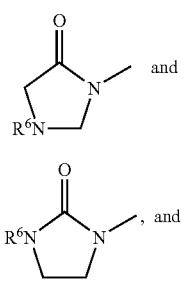

(b) a 6-membered heterocyclic ring selected from the group consisting of:

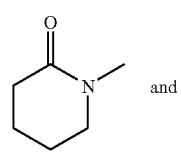

-continued

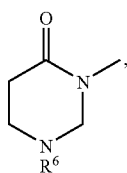

(ii)

wherein each carbon atom in the heterocyclic ring, formed when Y is joined together with the nitrogen and the carbonyl carbon shown in Formula I, is independently unsubstituted, mono- or di-substituted with a substituent selected at each occurrence from $R^7$.

Specific compounds within sub-class (iii) of this class are:
(1) 1-(3-{[7-propyl-3-(trifluoromethyl)-1,2-benzisoxazol-6-yl]oxy}propyl)imidazolidin-2-one,
(2) 1-(3-{[7-propyl-3-(trifluoromethyl)-1,2-benzisoxazol-6-yl]oxy}propyl)pyrrolidine-2,5-dione,
(3) 3-(3-{[7-propyl-3-(trifluoromethyl)-1,2-benzisoxazol-6-yl]oxy}propyl)thiazolidine-2,4-dione,
(4) 3-(3-{[7-propyl-3-(trifluoromethyl)-1,2-benzisoxazol-6-yl]oxy}propyl)imidazolidine-2,4-dione,
(5) 1-methyl-3-(3-{[7-propyl-3-(trifluoromethyl)-1,2-benzisoxazol-6-yl]oxy}propyl)imidazolidine-2,4-dione,
(6) 5,5-dimethyl-3-(3-{[7-propyl-3-(trifluoromethyl)-1,2-benzisoxazol-6-yl]oxy}propyl)imidazolidine-2,4-dione,
(7) 1-(2-pyridyl)-3-(3-{[7-propyl-3-(trifluoromethyl)-1,2-benzisoxazol-6-yl]oxy}propyl)imidazolidine-2,4-dione,
(8) 3-(3-{[7-propyl-3-(trifluoromethyl)-1,2-benzisoxazol-6-yl]oxy}propyl)-1-pyrazin-2-ylimidazolidine-2,4-dione,
(9) rac-5-methyl-5-phenyl-3-(3-{[7-propyl-3-(trifluoromethyl)-1,2-benzisoxazol-6-yl]oxy}propyl)imidazolidine-2,4-dione,
(10) rac-5-methyl-5-phenyl-3-(3-{[7-propyl-3-(trifluoromethyl)-1,2-benzisoxazol-6-yl]oxy}butyl)imidazolidine-2,4-dione,
(11) rac-5-methyl-5-(3-carboxyphenyl)-3-(3-{[7-propyl-3-(trifluoromethyl)-1,2-benzisoxazol-6-yl]oxy}propyl)imidazolidine-2,4-dione,
(12) rac-5-methyl-5-(2-pyridyl)-3-(3-{[7-propyl-3-(trifluoromethyl)-1,2-benzisoxazol-6-yl]oxy}propyl)imidazolidine-2,4-dione,
(13) rac-3-[2,5-dioxo-4-phenyl-1-(3-{[7-propyl-3-(trifluoromethyl)-1,2-benzisoxazol-6-yl]oxy}propyl)imidazolidin-4-yl]propanoic acid,
(14) 2-[2-oxo-3-(3-{[7-propyl-3-(trifluoromethyl)-1,2-benzisoxazol-6-yl]oxy}propyl)imidazolidin-1-yl]propanoic acid,
(15) 1-(3-{[7-propyl-3-(trifluoromethyl)-1,2-benzisoxazol-6-yl]oxy}propyl)piperidin-2-one,
(16) 1-(3-{[7-propyl-3-(trifluoromethyl)-1,2-benzisoxazol-6-yl]oxy}propyl)piperidin-2,6-dione,
(17) 1-[cis-2-{[7-propyl-3-(trifluoromethyl)-1,2-benzisoxazol-6-yl]oxy}cyclohexyl)methyl]dihydropyrimidine-2,4(1H,3H)-dione,
(18) 6-phenyl-3-(3-{[7-propyl-3-(trifluoromethyl)-1,2-benzisoxazol-6-yl]oxy}propyl)dihydropyrimidine-2,4(1H,3H)dione,
(19) 1-phenyl-3-(3-{[7-propyl-3-(trifluoromethyl)-1,2-benzisoxazol-6-yl]oxy}propyl)dihydropyrimidine-2,4(1H,3H)-dione,
(20) 3-(3-{[7-propyl-3-(trifluoromethyl)-1,2-benzisoxazol-6-yl]oxy}propyl)-1-pyridin-2-yldihydropyrimidine-2,4(1H,3H)-dione,
(21) 3-(3-{[7-propyl-3-(trifluoromethyl)-1,2-benzisoxazol-6-yl]oxy}propyl)-5,6-dihydro-2H-1,2'-bipyrimidine-2,4(3H)-dione, and
(22) 1-(3-{[7-propyl-3-(trifluoromethyl)-1,2-benzisoxazol-6-yl]oxy}propyl)azepan-2-one, and pharmaceutically acceptable salts, esters and tautomers thereof.

In an seventh embodiment of the present invention are those compounds of Formula I wherein Z is —$C_{3-6}$cycloalkyl-O—.

Specific compounds within this embodiment are:
(1) 1-[cis-2-{[7-propyl-3-(trifluoromethyl)-1,2-benzisoxazol-6-yl]oxy}cyclohexyl)methyl]dihydropyrimidine-2,4(1H,3H)-dione, and
(2) 1-[trans-2-{[7-propyl-3-(trifluoromethyl)-1,2-benzisoxazol-6-yl]oxy}cyclopentyl)methyl]dihydropyrimidine-2,4(1H,3H)-dione, and pharmaceutically acceptable salts, esters and tautomers thereof.

In a eighth embodiment of the present invention are those compounds of Formula I wherein Z is —$C_{4-6}$alkyl-.

Specific compounds within this embodiment are:
1-{4-[7-propyl-3-(trifluoromethyl)-1,2-benzisoxazol-6-yl]butyl}dihydropyrimidine-2,4(1H,3H)-dione, and pharmaceutically acceptable salts, esters and tautomers thereof.

Another aspect of the present invention, which applies to all of the embodiments of this invention, provides that when $R_1$ is —$CF_3$, $R_2$ is n-propyl, and Z is n-propyloxy, the 6-membered heterocyclic ring is not unsubstituted 5,6-dihydrouracil, as shown immediately below:

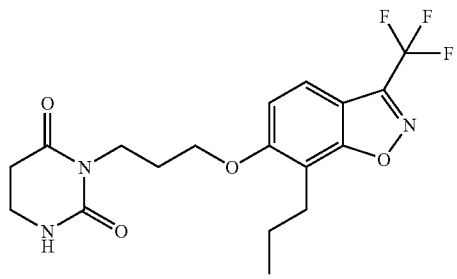

Particular novel compounds of structural Formula I which may be employed in the methods, uses and compositions of the present invention, include:
(1) 1-(3-{[7-propyl-3-(neopentyl)-1,2-benzisoxazol-6-yl]oxy}propyl)pyrrolidine-2,5-dione,
(2) 1-(3-{[7-propyl-3-(trifluoromethyl)-1,2-benzisoxazol-6-yl]oxy}propyl)pyrrolidine-2,5-dione,
(3) 2-(3-{[7-propyl-3-(trifluoromethyl)-1,2-benzisoxazol-6-yl]oxy}propyl)-1H-isoindole-1,3 (2H)-dione,
(4) 3,3-dimethyl-1-(3-{[7-propyl-3-(trifluoromethyl)-1,2-benzisoxazol-6-yl]oxy}propyl)pyrrolidine-2,5-dione,
(5) 3-methyl-3-phenyl-1-(3-{[7-propyl-3-(trifluoromethyl)-1,2-benzisoxazol-6-yl]oxy}propyl)pyrrolidine-2,5-dione,
(6) 3-(3-{[7-propyl-3-(neopentyl)-1,2-benzisoxazol-6-yl]oxy}propyl)thiazolidine-2,4-dione,
(7) 3-(3-{[7-propyl-3-(trifluoromethyl)-1,2-benzisoxazol-6-yl]oxy}propyl)thiazolidine-2,4-dione, (8) 5,5-dimethyl-3-(3-{[7-propyl-3-(neopentyl)-1,2-benzisoxazol-6-yl]oxy}propyl)thiazolidine-2,4-dione,
(9) [2,4-dioxo-3-(3-{[7-propyl-3-(neopentyl)-1,2-benzisoxazol-6-yl]oxy}propyl)-1,3-thiazolidin-5-yl]acetic acid,
(10) 3-(3-{[7-propyl-3-(neopentyl)-1,2-benzisoxazol-6-yl]oxy}propyl)imidazolidine-2,4-dione,
(11) 3-(3-{[7-propyl-3-(trifluoromethyl)-1,2-benzisoxazol-6-yl]oxy}propyl)imidazolidine-2,4-dione,
(12) 1-methyl-3-(3-{[7-propyl-3-(trifluoromethyl)-1,2-benzisoxazol-6-yl]oxy}propyl)imidazolidine-2,4-dione,
(13) 5(R)-methyl-3-(3-{[7-propyl-3-(trifluoromethyl)-1,2-benzisoxazol-6-yl]oxy}propyl)imidazolidine-2,4-dione,
(14) 5,5-dimethyl-3-(3-{[7-propyl-3-(trifluoromethyl)-1,2-benzisoxazol-6-yl]oxy}propyl)imidazolidine-2,4-dione,
(15) 1-(2-pyridyl)-3-(3-{[7-propyl-3-(trifluoromethyl)-1,2-benzisoxazol-6-yl]oxy}propyl)imidazolidine-2,4-dione,
(16) 5-methyl-5-phenyl-3-(3-{[7-propyl-3-(trifluoromethyl)-1,2-benzisoxazol-6-yl]oxy}propyl)imidazolidine-2,4-dione,
(17) 5-methyl-5-phenyl-3-(3-{[7-propyl-3-(neopentyl)-1,2-benzisoxazol-6-yl]oxy}propyl)imidazolidine-2,4-dione,
(18) 5-methyl-5-phenyl-3-(3-{[7-propyl-3-(phenyl)-1,2-benzisoxazol-6-yl]oxy}propyl)imidazolidine-2,4-dione,
(19) 5-methyl-5-phenyl-3-(3-{[7-propyl-3-(trifluoromethyl)-1,2-benzisoxazol-6-yl]oxy}butyl)imidazolidine-2,4-dione,
(20) 5-methyl-5-(3-carboxyphenyl)-3-(3-{[7-propyl-3-(trifluoromethyl)-1,2-benzisoxazol-6-yl]oxy}propyl)imidazolidine-2,4-dione,
(21) 5-methyl-5-(4-pyridyl)-3-(3-{[7-propyl-3-(trifluoromethyl)-1,2-benzisoxazol-6-yl]oxy}propyl)imidazolidine-2,4-dione,
(22) 5-methyl-5-(3-pyridyl)-3-(3-{[7-propyl-3-(trifluoromethyl)-1,2-benzisoxazol-6-yl]oxy}propyl)imidazolidine-2,4-dione,
(23) 5-methyl-5-(2-pyridyl)-3-(3-{[7-propyl-3-(trifluoromethyl)-1,2-benzisoxazol-6-yl]oxy}propyl)imidazolidine-2,4-dione,
(24) 3-(3-{[7-propyl-3-(trifluoromethyl)-1,2-benzisoxazol-6-yl]oxy}propyl)-1-pyrimidin-2-ylimidazolidine-2,4-dione,
(25) 3-(3-{[7-propyl-3-(trifluoromethyl)-1,2-benzisoxazol-6-yl]oxy}propyl)-1-pyrazin-2-ylimidazolidine-2,4-dione,
(26) 3-[2,5-dioxo-4-phenyl-1-(3-{[7-propyl-3-(trifluoromethyl)-1,2-benzisoxazol-6-yl]oxy}propyl)imidazolidin-4-yl]propanoic acid,
(27) 4-[5,5-dimethyl-2,4-dioxo-3-(3-{[7-propyl-3-(trifluoromethyl)-1,2-benzisoxazol-6-yl]oxy}propyl)imidazolidin-1-yl]butanoic acid,
(28) 4-[5,5-methyl-2,4-dioxo-3-(3-{[7-propyl-3-(trifluoromethyl)-1,2-benzisoxazol-6-yl]oxy}propyl)imidazolidin-1-yl]pentanoic acid,
(29) 1-(3-{[7-propyl-3-(trifluoromethyl)-1,2-benzisoxazol-6-yl]oxy}propyl)imidazolidin-2-one,
(30) methyl 2-[2-oxo-3-(3-{[7-propyl-3-(trifluoromethyl)-1,2-benzisoxazol-6-yl]oxy}propyl)imidazolidin-1-yl]propanoate,
(31) 2-[2-oxo-3-(3-{[7-propyl-3-(trifluoromethyl)-1,2-benzisoxazol-6-yl]oxy}propyl)imidazolidin-1-yl]propanoic acid,
(32) 1-(3-{[7-propyl-3-(trifluoromethyl)-1,2-benzisoxazol-6-yl]oxy}propyl)imidazolidine-2,4-dione,
(33) 5,5-dimethyl-1-(3-{[7-propyl-3-(trifluoromethyl)-1,2-benzisoxazol-6-yl]oxy}propyl)imidazolidine-2,4-dione,
(34) 1-[cis-2-{[7-propyl-3-(trifluoromethyl)-1,2-benzisoxazol-6-yl]oxy}cyclohexyl]methyl]dihydropyrimidine-2,4(1H,3H)-dione,
(35) 1-[trans-2-{[7-propyl-3-(trifluoromethyl)-1,2-benzisoxazol-6-yl]oxy}cyclopentyl)methyl]dihydropyrimidine-2,4(1H,3H)-dione,
(36) 1-{4-[7-propyl-3-(trifluoromethyl)-1,2-benzisoxazol-6-yl]butyl}dihydropyrimidine-2,4(1H,3H)-dione,
(37) 5-phenyl-3-(3-{[7-propyl-3-(trifluoromethyl)-1,2-benzisoxazol-6-yl]oxy}propyl)dihydropyrimidine-2,4(1H,3H)-7-dione,
(38) 6-phenyl-3-(3-{[7-propyl-3-(trifluoromethyl)-1,2-benzisoxazol-6-yl]oxy}propyl)dihydropyrimidine-2,4(1H,3H)-dione,
(39) 5-Methyl-3-(3-{[7-propyl-3-(trifluoromethyl)-1,2-benzisoxazol-6-yl]oxy}propyl)dihydropyrimidine-2,4(1H,3H)-dione,
(40) 1,5-Dimethyl-3-(3-{[7-propyl-3-(trifluoromethyl)-1,2-benzisoxazol-6-yl]oxy}propyl)dihydropyrimidine-2,4(1H,3H)-dione,
(41) 1-phenyl-3-(3-{[7-propyl-3-(trifluoromethyl)-1,2-benzisoxazol-6-yl]oxy}propyl)dihydropyrimidine-2,4(1H,3H)-dione,
(42) 3-(3-{[7-propyl-3-(trifluoromethyl)-1,2-benzisoxazol-6-yl]oxy}propyl)-1-pyridin-2-yldihydropyrimidine-2,4(1H,3H)-dione,
(43) 3-(3-{[7-propyl-3-(trifluoromethyl)-1,2-benzisoxazol-6-yl]oxy}propyl)-5,6-dihydro-2H-1,2'-bipyrimidine-2,4(3H)-dione,
(44) 3-(3-{[7-propyl-3-(trifluoromethyl)-1,2-benzisoxazol-6-yl]oxy}propyl)-5,6-dihydro-2H-1,5'-bipyrimidine-2,4(3H)-dione,
(45) 1-(3-{[7-propyl-3-(neopentyl)-1,2-benzisoxazol-6-yl]oxy}propyl)piperidin-2-one,
(46) 1-(3-{[7-propyl-3-(trifluoromethyl)-1,2-benzisoxazol-6-yl]oxy}propyl)piperidin-2-one,
(47) 1-(3-{[7-propyl-3-(trifluoromethyl)-1,2-benzisoxazol-6-yl]oxy}propyl)piperidin-2,6-dione,
(48) 1-(3-{[7-propyl-3-(phenyl)-1,2-benzisoxazol-6-yl]oxy}propyl)piperidin-2,5-dione,
(49) 4-(3-{[7-propyl-3-(trifluoromethyl)-1,2-benzisoxazol-6-yl]oxy}propyl)morpholine-3,5-dione,
(50) 1-(3-{[7-propyl-3-(trifluoromethyl)-1,2-benzisoxazol-6-yl]oxy}propyl)piperazine-2,5-dione,
(51) 4-(3-{[7-propyl-3-(trifluoromethyl)-1,2-benzisoxazol-6-yl]oxy}propyl)piperazine-2-one,
(52) 3-(3-{[7-propyl-3-(trifluoromethyl)-1,2-benzisoxazol-6-yl]oxy}propyl)-1,3,5-triazinane-2,4-dione,
(53) 3-(3-{[7-propyl-3-(phenyl)-1,2-benzisoxazol-6-yl]oxy}propyl)dihydropyrimidine-2,4(1H,3H)-dione,
(54) 6-methyl-3-(3-{[7-propyl-3-(trifluoromethyl)-1,2-benzisoxazol-6-yl]oxy}propyl)dihydropyrimidine-2,4(1H,3H)-dione, and
(55) (1) 1-(3-{[7-propyl-3-(trifluoromethyl)-1,2-benzisoxazol-6-yl]oxy}propyl)imidazolidin-2-one, and pharmaceutically acceptable salts, esters and tautomers thereof.

One subclass of compounds of the present invention includes compounds wherein $R^1$ is —$CF_3$ or phenyl, and $R^2$ is n-propyl. Particular compounds of this subclass include:
(1) 11-(3-{[7-propyl-3-(trifluoromethyl)-1,2-benzisoxazol-6-yl]oxy}propyl)imidazolidin-2-one,
(2) 1-(3-{[7-propyl-3-(trifluoromethyl)-1,2-benzisoxazol-6-yl]oxy}propyl)pyrrolidine-2,5-dione,
(3) 3-(3-{[7-propyl-3-(trifluoromethyl)-1,2-benzisoxazol-6-yl]oxy}propyl)thiazolidine-2,4-dione,
(4) 3-(3-{[7-propyl-3-(trifluoromethyl)-1,2-benzisoxazol-6-yl]oxy}propyl)imidazolidine-2,4-dione, (5) 1-Methyl-3-(3-{[7-propyl-3-(trifluoromethyl)-1,2-benzisoxazol-6-yl]oxy}propyl)imidazolidine-2,4-dione,
(6) 5,5-dimethyl-3-(3-{[7-propyl-3-(trifluoromethyl)-1,2-benzisoxazol-6-yl]oxy}propyl)imidazolidine-2,4-dione,
(7) 1-Phenyl-3-(3-{[7-propyl-3-(trifluoromethyl)-1,2-benzisoxazol-6-yl]oxy}propyl)imidazolidine-2,4-dione,
(8) 1-(2-pyridyl)-3-(3-{[7-propyl-3-(trifluoromethyl)-1,2-benzisoxazol-6-yl]oxy}propyl)imidazolidine-2,4-dione,
(9) 5-Phenyl-5-methyl-3-(3-{[7-propyl-3-(trifluoromethyl)-1,2-benzisoxazol-6-yl]oxy}propyl)imidazolidine-2,4-dione,
(10) 5-Phenyl-5-methyl-3-(3-{[7-propyl-3-(trifluoromethyl)-1,2-benzisoxazol-6-yl]oxy}butyl)imidazolidine-2,4-dione,
(11) 5-Phenyl-5-methyl-3-(3-{[7-propyl-3-(phenyl)-1,2-benzisoxazol-6-yl]oxy}propyl)imidazolidine-2,4-dione,
(12) 5-(3-carboxyphenyl)-5-methyl-3-(3-{[7-propyl-3-(trifluoromethyl)-1,2-benzisoxazol-6-yl]oxy}propyl)imidazolidine-2,4-dione,
(13) 5-(2-Pyridyl)-5-methyl-3-(3-{[7-propyl-3-(trifluoromethyl)-1,2-benzisoxazol-6-yl]oxy}propyl)imidazolidine-2,4-dione,
(14) 5-Phenyl-5-(3-propionyl)-3-(3-{[7-propyl-3-(trifluoromethyl)-1,2-benzisoxazol-6-yl]oxy}propyl)imidazolidine-2,4-dione,
(15) 2-[2-oxo-3-(3-{[7-propyl-3-(trifluoromethyl)-1,2-benzisoxazol-6-yl]oxy}propyl)imidazolidin-1-yl]propanoic acid,
(16) 1-(3-{[7-propyl-3-(trifluoromethyl)-1,2-benzisoxazol-6-yl]oxy}propyl)piperidin-2-one,
(17) 1-(3-{[7-propyl-3-(trifluoromethyl)-1,2-benzisoxazol-6-yl]oxy}propyl)piperidin-2,6-dione,
(18) 1-(3-{[7-propyl-3-(phenyl)-1,2-benzisoxazol-6-yl]oxy}propyl)piperidin-2,5-dione,
(19) 1-[cis-2-{[7-propyl-3-(trifluoromethyl)-1,2-benzisoxazol-6-yl]oxy}cyclohexyl)methyl]dihydropyrimidine-2,4(1H,3H)-dione,
(20) 3-(3-{[7-propyl-3-(phenyl)-1,2-benzisoxazol-6-yl]oxy}propyl)-dihydropyrimidine-2,4(1H,3H)-dione,
(21) 6-phenyl-3-(3-{[7-propyl-3-(trifluoromethyl)-1,2-benzisoxazol-6-yl]oxy}propyl)dihydropyrimidine-2,4(1H,3H)-dione,
(22) 1-phenyl-3-(3-{[7-propyl-3-(trifluoromethyl)-1,2-benzisoxazol-6-yl]oxy}propyl)dihydropyrimidine-2,4(1H,3H)-dione,
(23) 3-(3-{[7-propyl-3-(trifluoromethyl)-1,2-benzisoxazol-6-yl]oxy}propyl)-1-pyridin-2-yldihydropyrimidine-2,4(1H,3H)-dione,
(24) 3-(3-{[7-propyl-3-(trifluoromethyl)-1,2-benzisoxazol-6-yl]oxy}propyl)-5,6-dihydro-2H-1,2'-bipyrimidine-2,4(3H)-dione, and
(25) 1-(3-{[7-propyl-3-(trifluoromethyl)-1,2-benzisoxazol-6-yl]oxy}propyl)azepan-2-one, and pharmaceutically acceptable salts, esters and tautomers thereof.

As used herein "alkyl" is intended to include both branched- and straight-chain saturated aliphatic hydrocarbon groups having the specified number of carbon atoms. Examples of alkyl groups include, but are not limited to, methyl (Me), ethyl (Et), n-propyl (Pr), n-butyl (Bu), n-pentyl, n-hexyl, and the isomers thereof such as isopropyl (i-Pr), isobutyl (i-Bu), secbutyl (s-Bu), tertbutyl (t-Bu), isopentyl, isohexyl and the like.

The term "$C_{2-6}$alkenyl" as used herein, refers to a straight or branched 2–6 carbon chain with at least one carbon-carbon double bond. Examples of alkenyl include, but are not limited to, vinyl, allyl, isopropenyl, pentenyl, hexenyl, heptenyl, 1-propenyl, 2-butenyl, 2-methyl-2-butenyl, and the like.

"$C_{3-6}$cycloalkyl" means a monocyclic saturated carbocyclic ring, having from 3 to 6 carbon atoms, wherein one carbocyclic ring carbon is the point of attachment. Examples of cycloalkyl include, but are not limited to, cyclopropyl, cyclobutyl, cyclopentyl, cyclohexyl, and the like.

"$C_{3-6}$spiroalkyl" means a monocyclic saturated cycloalkyl ring, having from 3 to 6 carbon atoms, wherein the spiro union is formed by a single carbon atom which is the only common carbon atom of two cycloalkyl rings. An example of a $C_3$ spiroalkyl substituent is equivalent to

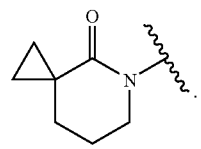

"$C_{3-6}$cycloheteroalkyl" means a monocyclic saturated ring containing at least one heteroatom selected from N, S and O, each of said ring having from 3 to 6 atoms in which the point of attachment may be carbon or nitrogen. Examples of "cycloheteroalkyl" include, but are not limited to, pyrrolidinyl, piperidinyl, piperazinyl, imidazolidinyl, tetrahydrofuranyl, morpholinyl, and the like.

The terms "halo" or "halogen" are meant to include fluoro, chloro, bromo and iodo, unless otherwise noted. Fluoro is preferred.

Herein, the term "pharmaceutically acceptable salts" shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine, morpholine, 2,4,4-trimethyl-2-pentamine and tris(hydroxymethyl)aminomethane. Pharmaceutically acceptable esters at the carboxylic acid group can be made by treating a dihydroxy open acid statin with an alcohol. Examples of pharmaceutically acceptable esters include, but are not limited to, —$C_{1-4}$alkyl and —$C_{1-4}$alkyl substituted with phenyl-, dimethylamino-, and acetylamino. "$C_{1-4}$alkyl" herein includes straight or branched aliphatic chains containing from 1 to 4 carbon atoms, for example methyl, ethyl, n-propyl, n-butyl, iso-propyl, sec-butyl and tert-butyl.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

Under standard nomenclature used throughout this disclosure, the terminal portion of the designated side chain is described first, followed by the adjacent functionality toward the point of attachment. For example, a $C_{1-5}$alkylcarbonylamino $C_{1-6}$alkyl substituent is equivalent to

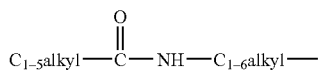

When referring to moieties which may optionally be substituted herein, e.g., alkyl groups, cycloalkyl groups, phenyl groups, heterocycloalkyl groups, and the like, the phrases used herein "unsubstituted, mono- or di-substituted with a substituent independently selected at each occurrence" and "unsubstituted, mono- or poly-substituted with a substituent selected from" are intended to mean that the total number of substituents on the moiety overall may be zero, one or more than one, and that each carbon and nitrogen atom available for substitution in the given moiety may independently be unsubstituted or mono- or poly-substituted, with one or more substituents that are the same or different at each occurrence and which result in the creation of a stable structure. The term "poly-substituted" is intended to mean two or more substituents, e.g. di-, tri-, tetra-, penta-substitution and higher as appropriate.

In choosing compounds of the present invention, one of ordinary skill in the art will recognize that the various substituents, i.e. $R^1$, $R^2$, etc., are to be chosen in conformity with well-known principles of chemical structure connectivity and stability. When any variable (e.g., $R^1$, $R^2$, etc.) occurs more than one time in any constituent or in formula I, its definition on each occurrence is independent of its definition at every other occurrence. Also, combinations of substituents and/or variables are permissible only if such combinations result in stable compounds.

Compounds of Formula I may contain one or more asymmetric centers and can thus occur as racemates and racemic mixtures, single enantiomers, enantiomeric mixtures, diastereomeric mixtures and individual diastereomers. The present invention is meant to comprehend all such isomeric forms of the compounds of Formula I. All such isomeric forms of the compounds of Formula I are included within the scope of this invention.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers of the compounds of Formula I, as well as mixtures thereof, are included in the scope of this invention. By way of illustration, tautomers included in this definition include, but are not limited to:

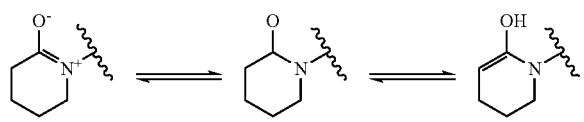

The term "rac" means racemic mixture, which is defined as a mixture comprised of equal amounts of enantiomers. If desired, racemic mixtures of compounds of Formula I may be separated by the coupling of a racemic mixture of the compounds of Formula I to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage and removal of the added chiral residue. The racemic mixture of the compounds of Formula I can also be separated directly by chromatographic methods utilizing chiral stationary phases, which methods are well known in the art.

Alternatively, any enantiomer of a compound of the general Formula I may be obtained by stereoselective synthesis using optically pure starting materials or reagents of known configuration. Such methods are well known in the art.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

Some abbreviations used herein are as follows: Ac is acetyl [$CH_3C(O)$—]; PG is protecting group; LG is leaving group; $Ac_2O$ is acetic anhydride; 9-BBN is 9-borabicyclo[3.3.1]nonane; $Pd(dba)_2$ is tris(dibenzylideneacetone)dipalladium, PdCl2dppf is dichlorobis-(triphenylphosphene) palladium, Ph is phenyl; PhMe is toluene; $PPh_3$ is triphenylphosphine; Bn is benzyl; Me is methyl, Et is ethyl, EtOH is ethanol, EtOAc is ethyl acetate, $Et_3N$ is triethylamine, tBu is tert-butyl, PMB is para-methoxybenzyl; DMF is N,N-dimethylformamide; DMSO is dimethyl sulfoxide; DIAD is diisopropylazodicarboxylate; $Tf_2O$ is triflic anhydride, Tf is triflate, TBAF is tetrabutyl ammonium fluoride; THF is tetrahydrofuran; TMS is trimethylsilyl; TBS is tert-butyldimethylsilyl; HOBt is 1-hydroxybenzotriazole; EDAC (or EDC) is 1-ethyl-3-[3-(dimethylamino)propyl]-carbodiimide HCl; HCl is hydrochloric acid; NaHMDS is sodium hexamethyldisiliazide; DIBAL is diisobutylaluminum hydride; TPAP is tetrapropylammonium perruthenate; NMO is N-methylmorpholine N oxide; MsCl methanesulfonyl chloride; HPLC is high performance liquid chromatography; NaOAc is sodium acetate; NaOtBu is sodium tert-butoxide, TLC is thin layer chromatography; RT is room temperature; N is normal; mmol is millimole; M is molar; TFA is trifluoroacetic acid.

General Schemes

The compounds of this invention can be prepared employing the following general procedures. Benzisoxazole intermediates may be prepared from commercially available or readily accessible resorcinols as shown in Scheme 1 or alternate synthetic pathways as reported in the literature. See for example: Shutske, G. M. et al. *J. Med. Chem.*, 25 (1), 36, (1982); Poissonnet, G. *Synth. Commun.*, 27 (22), 3839–3846, (1997); Crabbe, P. Villarino, A. Muchowski, J. M. *J. Chem. Soc., Perkin Trans* 1, 1973, 2220.

SCHEME 1

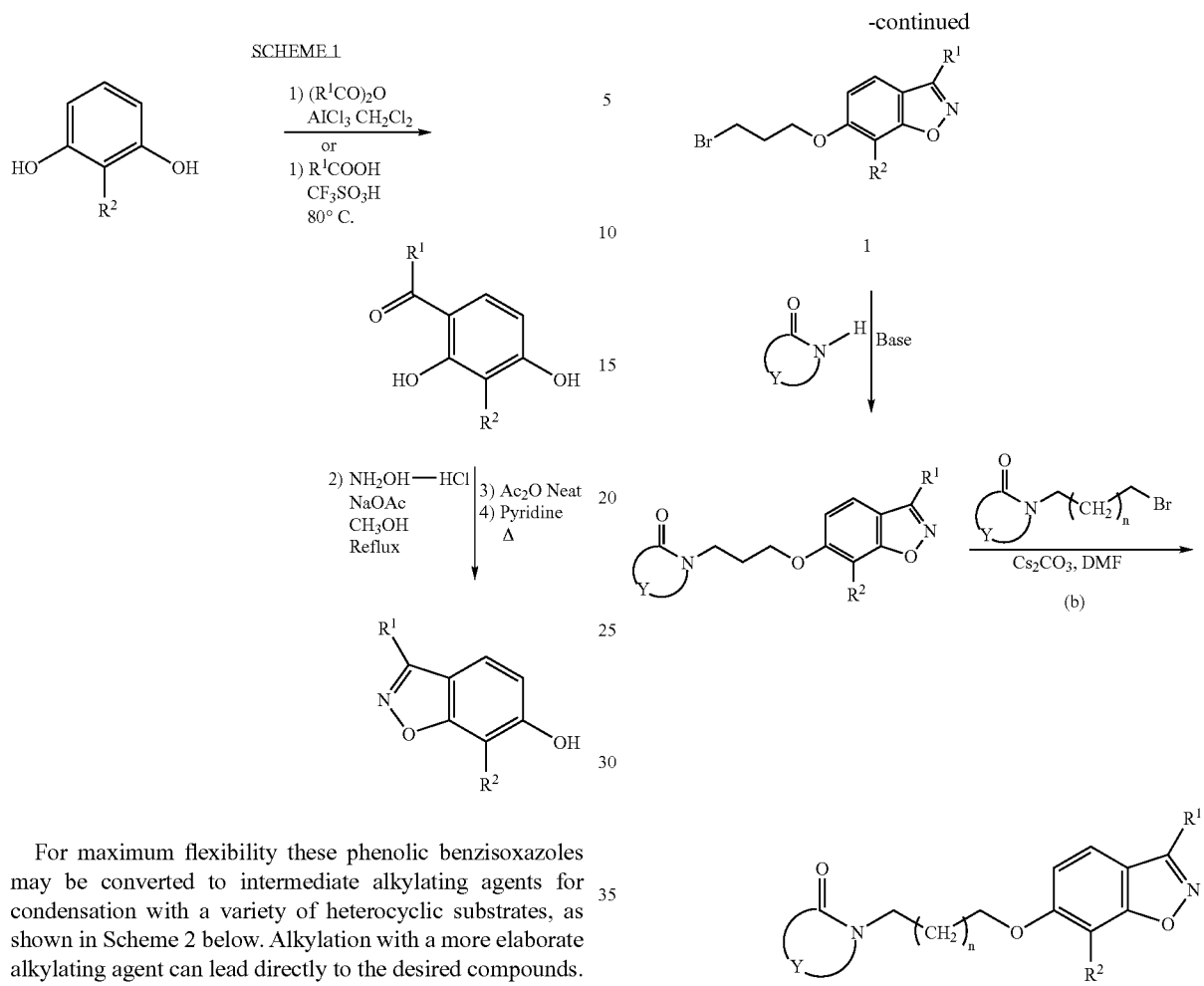

For maximum flexibility these phenolic benzisoxazoles may be converted to intermediate alkylating agents for condensation with a variety of heterocyclic substrates, as shown in Scheme 2 below. Alkylation with a more elaborate alkylating agent can lead directly to the desired compounds.

SCHEME 2

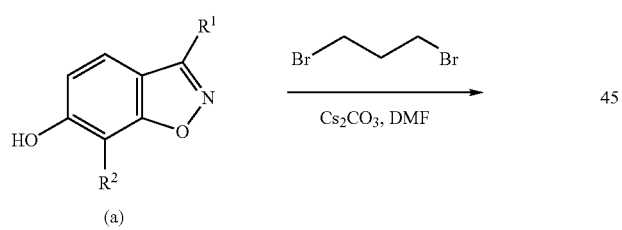

As an alternative approach, or for use where the bromide or halide intermediates might be difficult to access, many variations of the Mitsunobu coupling can also be used to construct these compounds as indicated in Scheme 3 below.

SCHEME 3

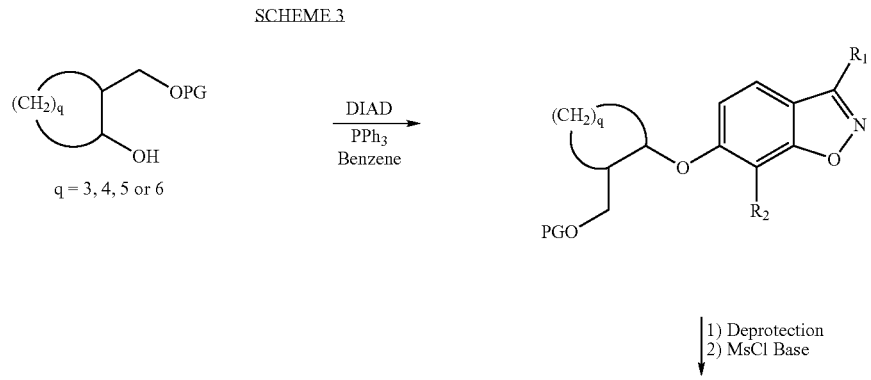

1) Deprotection
2) MsCl Base

27

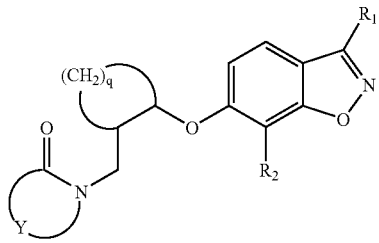

-continued

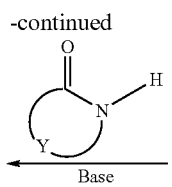

28

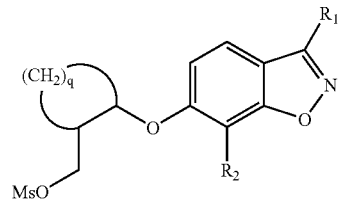

In many of the current examples, the heterocyclic partner will be commercially available or accessible by well known methods. Several examples derive from substituted hydantoins and dihydropyrimidinediones. In addition to the various published routes to these intermediates, the general procedures of Schemes 4 and 5 have been found to give access to the desired intermediate heteroaryls. In Scheme 4, R' and R" are alkyl or aryl substituents as desired, and the ester residue R''' can also be alkyl or aryl as desired.

The desired heterocyclic fragments are prepared as shown in Schemes 4 and 5 below. Depending on the exact example chosen, the heterocyclic intermediate is then converted to the desired final product as shown in schemes 2 and 3.

SCHEME 4

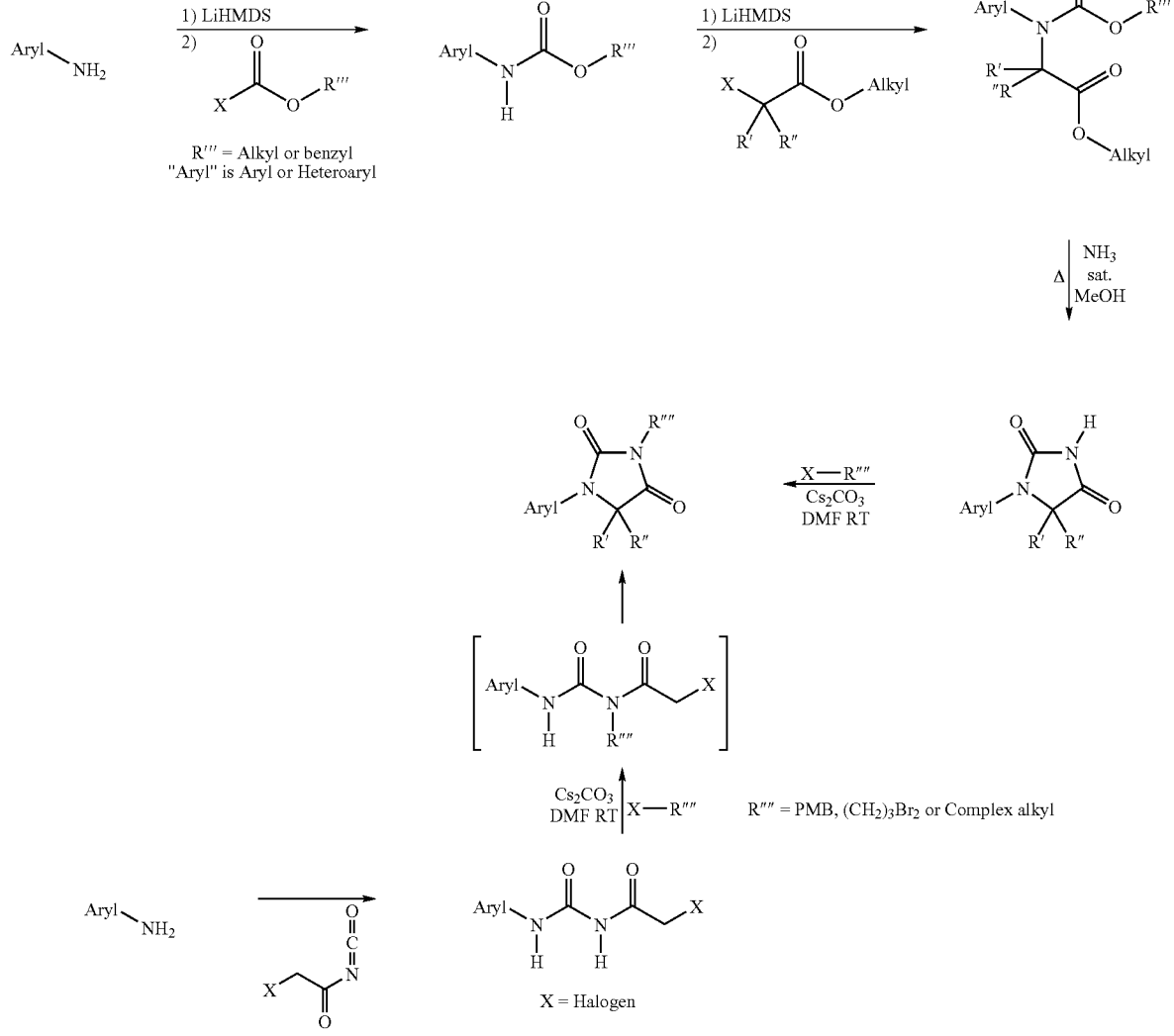

Many of the N-aryl and N-heteroaryl analogs claimed here are accessible through palladium(0) mediated couplings of nitrogen heterocycles with an aryl or heteroaryl halide partner as typified by Scheme 5. R' in Scheme 5 can be a protecting group, a partially or a completely elaborated fragment of the desired target.

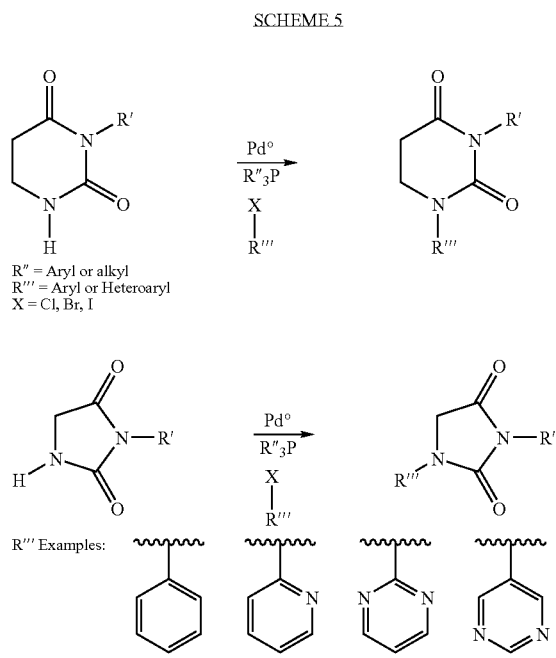

The instant invention provides methods for treating lipid disorders, particularly for treating below-desired plasma HDL cholesterol levels, as well as for treating and/or reducing the risk for diseases and conditions affected by LXR activity, comprising administering a therapeutically effective amount of a compound of Formula I to a person in need of such treatment. Any patient having a depressed plasma HDL cholesterol level, or desiring to increase their HDL cholesterol level may use this treatment. Particularly suitable patients in need of such treatment are those whose plasma HDL cholesterol level is depressed, i.e., below the clinically desirable level. Currently, the clinically desirable HDL cholesterol level is considered to be about 40 mg/dl or higher in men and about 50 mg/dl or higher in women.

The method of this invention also serves to prevent lipid accumulation in, or remove lipids from, tissue deposits such as atherosclerotic plaques or xanthomas in a patient with atherosclerotic disease manifest by clinical signs such as angina, claudication, bruits, one that has suffered a myocardial infarction or transient ischemic attack, or one diagnosed by angiography, sonography or MRI.

Further provided are methods for preventing or reducing the risk of developing atherosclerosis, as well as for halting or slowing the progression of atherosclerotic disease once it has become clinically evident, comprising the administration of a prophylactically or therapeutically effective amount, as appropriate, of a compound of Formula I to a mammal, including a human, who is at risk of developing atherosclerosis or who already has atherosclerotic disease.

Atherosclerosis encompasses vascular diseases and conditions that are recognized and understood by physicians practicing in the relevant fields of medicine. Atherosclerotic cardiovascular disease including restenosis following revascularization procedures, coronary heart disease (also known as coronary artery disease or ischemic heart disease), cerebrovascular disease including multi-infarct dementia, and peripheral vessel disease including erectile dysfunction are all clinical manifestations of atherosclerosis and are therefore encompassed by the terms "atherosclerosis" and "atherosclerotic disease."

A compound of Formula I may be administered to prevent or reduce the risk of occurrence, or recurrence where the potential exists, of a coronary heart disease event, a cerebrovascular event, and/or intermittent claudication. Coronary heart disease (CHD) events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists.

Accordingly, the instant invention also provides a method for preventing or reducing the risk of a first or subsequent occurrence of an atherosclerotic disease event comprising the administration of a prophylactically effective amount of a compound of Formula I to a patient at risk for such an event. The patient may or may not have atherosclerotic disease at the time of administration, or may be at risk for developing it.

Persons to be treated with the instant therapy include those with dyslipidemic conditions including depressed or below-desirable plasma levels of HDL cholesterol, as well as those at risk of developing atherosclerotic disease and of having an atherosclerotic disease event. Standard atherosclerotic disease risk factors are known to the average physician practicing in the relevant fields of medicine. Such known risk factors include but are not limited to hypertension, smoking, diabetes, low levels of high density lipoprotein cholesterol, and a family history of atherosclerotic cardiovascular disease. Published guidelines for determining those who are at risk of developing atherosclerotic disease can be found in: Executive Summary of the Third Report of the National Cholesterol Education Program (NCEP) Expert Panel on Detection, Evaluation, and Treatment of High Blood Cholesterol in Adults (Adult Treatment Panel III), JAMA, 2001; 285 pp. 2486–2497. People who are identified as having one or more of the above-noted risk factors are intended to be included in the group of people considered at risk for developing atherosclerotic disease. People identified as having one or more of the above-noted risk factors, as well as people who already have atherosclerosis, are intended to be included within the group of people considered to be at risk for having an atherosclerotic disease event.

The term "patient" includes mammals, especially humans, who use the instant active agents for the prevention or treatment of a medical condition. Administering of the drug to the patient includes both self-administration and administration to the patient by another person. The patient may be in need of treatment for an existing disease or medical condition, or may desire prophylactic treatment to prevent or reduce the risk for diseases and medical conditions affected by reverse cholesterol transport.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician. The term "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. Particularly, the dosage amount of a compound of Formula I that a patient receives can be selected so as to achieve the amount of lipid level modification desired, particularly to achieve a desired level of HDL cholesterol. The dosage a patient receives may also be titrated over time in order to reach a target lipid profile. The dosage regimen utilizing a compound of Formula I is selected in accordance with a variety of factors including type, species, age, weight, sex and medical condition of the patient; the severity of the condition to be treated; the potency of the compound chosen to be administered; drug combinations; the route of administration; and the renal and hepatic function of the patient. A consideration of these factors is well within the purview of the ordinarily skilled clinician for the purpose of determining the therapeutically effective or prophylactically effective dosage amount needed to prevent, counter, or arrest the progress of the condition.

An effective amount of compound for use in the method of this invention is about 0.01 mg/kg to about 30 mg/kg of body weight per day, or about 0.7 mg to about 2100 mg per patient in single or divided doses per day. More particularly, an amount of about 7 mg to about 1050 mg per patient in single or divided doses per day can be administered. However, dosage amounts will vary depending on factors as noted above, including the potency of the particular compound. Although the active drug of the present invention may be administered in divided doses, for example from one to four times daily, a single daily dose of the active drug is preferred.

The active drug employed in the instant therapy can be administered in such oral forms as tablets, capsules, pills, powders, granules, elixirs, tinctures, suspensions, syrups, and emulsions. Oral formulations are preferred.

Administration of the active drug can be via any pharmaceutically acceptable route and in any pharmaceutically acceptable dosage form. This includes the use of oral conventional rapid-release, time controlled-release and delayed-release (such as enteric coated) pharmaceutical dosage forms. Additional suitable pharmaceutical compositions for use with the present invention are known to those of ordinary skill in the pharmaceutical arts; for example, see Remington's Pharmaceutical Sciences, Mack Publishing Co., Easton, Pa.

In the methods of the present invention, the active drug is typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with a non-toxic, pharmaceutically acceptable, inert carrier such as lactose, starch, sucrose, glucose, modified sugars, modified starches, methyl cellulose and its derivatives, dicalcium phosphate, calcium sulfate, mannitol, sorbitol and other reducing and non-reducing sugars, magnesium stearate, steric acid, sodium stearyl fumarate, glyceryl behenate, calcium stearate and the like. For oral administration in liquid form, the drug components can be combined with non-toxic, pharmaceutically acceptable inert carrier such as ethanol, glycerol, water and the like. Moreover, when desired or necessary, suitable binders, lubricants, disintegrating agents and coloring and flavoring agents can also be incorporated into the mixture. Stabilizing agents such as antioxidants, for example butylated hydroxyanisole (BHA), 2,6-di-tert-butyl-4-methylphenol (BHT), propyl gallate, sodium ascorbate, citric acid, calcium metabisulphite, hydroquinone, and 7-hydroxycoumarin, can also be added to stabilize the dosage forms. Other suitable components include gelatin, sweeteners, natural and synthetic gums such as acacia, tragacanth or alginates, carboxymethylcellulose, polyethylene glycol, waxes and the like.

The active drug can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Active drug may also be delivered by the use of monoclonal antibodies as individual carriers to which the compound molecules are coupled. Active drug may also be coupled with soluble polymers as targetable drug carriers. Such polymers can include polyvinyl-pyrrolidone, pyran copolymer, polyhydroxy-propyl-methacrylamide-phenol, polyhydroxy-ethyl-aspartamide-phenol, or polyethyleneoxide-polylysine substituted with palmitoyl residues. Furthermore, active drug may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier.

In a broad embodiment, any suitable additional active agent or agents may be used in combination with the compound of Formula I in a single dosage formulation, or may be administered to the patient in a separate dosage formulation, which allows for concurrent or sequential administration of the active agents. One or more additional active agents may be administered with a compound of Formula I. The additional active agent or agents can be lipid modifying compounds or agents having other pharmaceutical activities, or agents that have both lipid-modifying effects and other pharmaceutical activities. Examples of additional active agents which may be employed include but are not limited to HMG-CoA reductase inhibitors, which include statins in their lactonized or dihydroxy open acid forms and pharmaceutically acceptable salts and esters thereof, including but not limited to lovastatin (see U.S. Pat. No. 4,342,767), simvastatin (see U.S. Pat. No. 4,444,784), dihydroxy open-acid simvastatin, particularly the ammonium or calcium salts thereof, pravastatin, particularly the sodium salt thereof (see U.S. Pat. No. 4,346,227), fluvastatin particularly the sodium salt thereof (see U.S. Pat. No. 5,354,772), atorvastatin, particularly the calcium salt thereof (see U.S. Pat. No. 5,273,995), pitavastatin also referred to as NK-104 (see PCT international publication number WO 97/23200) and rosuvastatin, also known as ZD-4522, (CRESTOR®; see U.S. Pat. No. 5,260,440, and Drugs of the Future, 1999, 24(5), pp. 511–513); HMG-CoA synthase inhibitors; squalene epoxidase inhibitors; squalene synthetase inhibitors (also known as squalene synthase inhibitors), acyl-coenzyme A: cholesterol acyltransferase (ACAT) inhibitors including selective inhibitors of ACAT-1 or ACAT-2 as well as dual inhibitors of ACAT-1 and -2; microsomal triglyceride transfer protein (MPT) inhibitors; niacin; bile acid sequestrants; LDL (low density lipoprotein) receptor inducers; platelet aggregation inhibitors, for example glycoprotein IIb/IIIa fibrinogen receptor antagonists and aspirin; human peroxisome proliferator activated receptor gamma (PPARγ) agonists including the compounds commonly referred to as glitazones for example pioglitazone and rosiglitazone and, including those compounds included within the structural class known as thiazolidine diones as well as those PPARγ agonists outside the thiazolidine dione structural class; PPARα agonists such as clofibrate, fenofibrate including micronized fenofibrate, and gemfibrozil; PPAR dual α/γ agonists; vitamin $B_6$ (also known as pyridoxine) and the pharmaceutically acceptable salts thereof such as the HCl salt; vitamin $B_{12}$ (also known as cyanocobalamin); folic acid or a pharmaceutically acceptable salt or ester thereof such as the sodium salt and the methylglucamine salt; anti-oxidant vitamins such as vitamin C and E and beta carotene; beta-blockers; angiotensin II antagonists such as losartan; angiotensin converting enzyme inhibitors such as enalapril and captopril; calcium channel blockers such as nifedipine and diltiazam; endothelian antagonists; agents that enhance ABCA1 gene expression; FXR ligands including both inhibitors and agonists; bisphosphonate compounds such as alendronate sodium; and cyclooxygenase-2 inhibitors such as rofecoxib and celecoxib.

Still another type of agent that can be used in combination with the compounds of this invention are cholesterol absorption inhibitors. Cholesterol absorption inhibitors block the movement of cholesterol from the intestinal lumen into enterocytes of the small intestinal wall. This blockade is their primary mode of action in reducing serum cholesterol levels. These compounds are distinct from compounds which reduce serum cholesterol levels primarily by mechanisms of action such as acyl coenzyme A—cholesterol-acyl transferase (ACAT) inhibition, inhibition of triglyceride synthesis, MTP inhibition, bile acid sequestration, and transcription modulation such as agonists or antagonists of nuclear hormones. Cholesterol absorption inhibitors are described in U.S. Pat. No. 5,846,966, U.S. Pat. No. 5,631,365, U.S. Pat. No. 5,767,115, U.S. Pat. No. 6,133,001, U.S. Pat. No. 5,886,171, U.S. Pat. No. 5,856,473, U.S. Pat. No. 5,756,470, U.S. Pat. No. 5,739,321, U.S. Pat. No. 5,919,672, WO 00/63703, WO/0060107, WO 00/38725, WO 00/34240, WO 00/20623, WO 97/45406, WO 97/16424, WO 97/16455, and WO 95/08532, the entire contents of all of which are hereby incorporated by reference.

An exemplary cholesterol absorption inhibitor is ezetimibe, also known as SCH-58235, which is 1-(4-fluorophenyl)-3(R)-[3(S)-(4-fluorophenyl)-3-hydroxypropyl)]-4(S)-(4-hydroxyphenyl)-2-azetidinone, described in U.S. Pat. Nos. 5,767,115 and 5,846,966 and shown below as

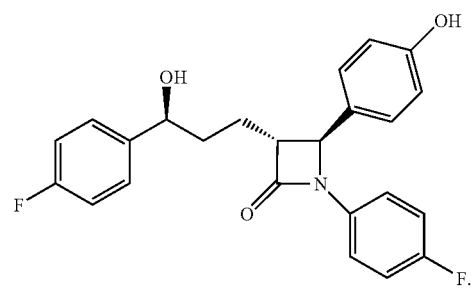

Additional exemplary hydroxy-substituted azetidinone cholesterol absorption inhibitors are specifically described in U.S. Pat. No. 5,767,115, column 39, lines 54–61 and column 40, lines 1–51 (hereby incorporated by reference), represented by the formula

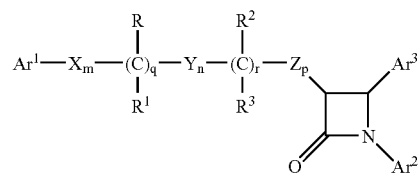

as defined in column 2, lines 20–63 (hereby incorporated by reference). These and other cholesterol absorption inhibitors can be identified according to the assay of hypolipidemic compounds using the hyperlipidemic hamster described in U.S. Pat. No. 5,767,115, column 19, lines 47–65 (hereby incorporated by reference), in which hamsters are fed a controlled cholesterol diet and dosed with test compounds for seven days. Plasma lipid analysis is conducted and data is reported as percent reduction of lipid versus control.

Therapeutically effective amounts of cholesterol absorption inhibitors include dosages of from about 0.01 mg/kg to about 30 mg/kg of body weight per day, preferably about 0.1 mg/kg to about 15 mg/kg. For an average body weight of 70 kg, the dosage level is therefore from about 0.7 mg to about 2100 mg of drug per day, e.g. 10, 20, 40, 100 or 200 mg per day, preferably given as a single daily dose or in divided doses two to six times a day, or in sustained release form. This dosage regimen may be adjusted to provide the optimal therapeutic response when the cholesterol absorption inhibitor is used in combination with a compound of the instant invention.

According to a further aspect of the present invention there is provided the use of a compound of Formula I for the manufacture of a medicament for the treatment, prevention, or reduction in risk of developing a LXR receptor mediated disease. A therapeutically or prophylactically effective amount, as appropriate, of a compound of Formula I can be used for the preparation of a medicament useful for treating lipid disorders, particularly for treating depressed HDL cholesterol levels as well as for treating and/or reducing the risk for diseases and conditions affected by agonism of LXR and affected by reverse cholesterol transport, preventing or reducing the risk of developing atherosclerotic disease, halting or slowing the progression of atherosclerotic disease once it has become clinically manifest, and preventing or reducing the risk of a first or subsequent occurrence of an atherosclerotic disease event. For example, the medicament may be comprised of about 0.7 mg to about 2100 mg of a compound of Formula I, or more particularly about 7 mg to about 1050 mg. The medicament comprised of a compound of Formula I may also be prepared with one or more additional active agents, such as those described supra.

As used herein, the term LXR includes all subtypes of this receptor. The compounds of Formula I are LXR ligands and individually may vary in their selectivity for one or the other of LXRα and LXRβ, or they may have mixed binding affinity for both LXRα and LXRβ. More particularly, the tested compounds included within the scope of this invention have an $IC_{50}$ less than or equal to 2 μM for at least one of either the LXRα or LXRβ receptors employing the LXR radioligand competition scintillation proximity assays described below in the Example section. Preferred tested compounds of Formula I bind to the human LXRα receptor and have an $IC_{50}$ less than or equal to 300 nM for the LXRα receptor.

Compound A is used in the following assays and has the following structural formula:

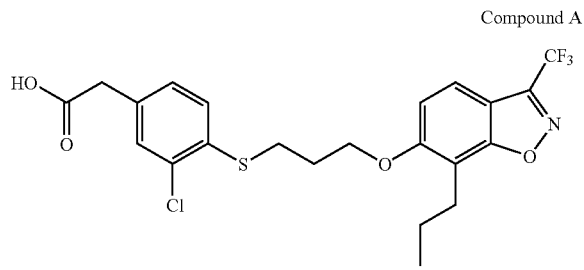

Compound A

Compound A and related compounds are disclosed along with methods for making them in WO97/28137 herein incorporated by reference in its entirety (U.S. Ser. No. 08/791,211, filed Jan. 31, 1997).

The compounds in the following examples were characterized using $^1$H NMR at 400 or 500 MHz field strength, and/or by ESI mass spectroscopy (MS).

EXAMPLE 1

Radioligand Competition Binding Scintillation Proximity Assays

Preparation of Recombinant Human LXRα and LXRβ

Human LXRα and LXRβ were expressed as GST-fusion proteins in *E. coli*. The ligand binding domain cDNAs for human LXRα (amino acids 164–447) and human LXRβ (amino acids 149–455) were subcloned into the pGEX-KT expression vector (Pharmacia). *E. coli* containing the respective plasmids were propagated, induced, and harvested by centrifugation. The re-suspended pellet was broken in a French press and debris was removed by centrifugation. Recombinant human LXR receptors were purified by affinity chromatography on glutathione sepharose and receptor was eluted with glutathione. Glycerol was added to a final concentration of 50% to stabilize the receptor and aliquots were stored at −80° C.

Binding to LXRα:

For each assay, an aliquot of human GST-LXRα receptor was incubated in a final volume of 100 μl SPA buffer (10 mM Tris, pH 7.2, 1 mM EDTA, 10% glycerol, 10 mM Na molybdate, 1 mM dithiothreitol, and 2 μg/ml benzamidine) containing 1.25 mg/ml yttrium silicate protein A coated SPA beads (Amersham Pharmacia Biotech, Inc.), 8.3 μg/ml anti-GST antibody (Amersham Pharmacia Biotech, Inc.), 0.1% non-fat dry milk and 25 nM [$^3$H$_2$]Compound A (13.4 Ci/mmole), ±test compound. After incubation for ~16 h at 15° C. with shaking, the assay plates were counted in a Packard Topcount. In this assay the $K_d$ for Compound A for LXRα is ≈15 nM.

Binding to LXRβ:

For each assay, an aliquot of human GST-LXRβ ligand binding domain receptor was incubated in a final volume of 100 μl SPA buffer (10 mM Tris, pH 7.2, 1 mM EDTA, 10% glycerol, 10 mM Na molybdate, 1 mM dithiothreitol, and 2 μg/ml benzamidine) containing 1.25 mg/ml yttrium silicate protein A coated SPA beads (Amersham Pharmacia Biotech, Inc.), 8.3 μg/ml anti-GST antibody (Amersham Pharmacia Biotech, Inc.) 0.1% non-fat dry milk and 25 nM [$^3$H$_2$]Compound A (13.4 Ci/mmole), ±test compound. After incubation for ~16 h at 15° C. with shaking, the assay plates were counted in a Packard Topcount. In this assay the $K_d$ for Compound A for LXRβ is ~10 nM.

Results:

Representative tested compounds of Formula I are ligands for human LXRα and/or human LXRβ, each having an $IC_{50} \leq 1,800$ nM for at least one of the LXRα receptor or the LXRβ receptor, and preferred tested compounds having an $IC_{50}$ of 300 nM or less for at least one of the LXRα receptor or the LXRβ receptor.

EXAMPLE 2

Transactivation Assay

Plasmids

Expression constructs were prepared by inserting the ligand binding domain (LBD) of human LXRα and LXRβ cDNAs adjacent to the yeast GAL4 transcription factor DNA binding domain (DBD) in the mammalian expression vector pcDNA3 to create pcDNA3-LXRα/GAL4 and pcDNA3-LXRβ/GAL4, respectively. The GAL4-responsive reporter construct, pUAS(5×)-tk-luc, contained 5 copies of the GAL4 response element placed adjacent to the thymidine kinase minimal promoter and the luciferase reporter gene. The transfection control vector, pEGPP-N1, contained the Green Fluorescence Protein (GFP) gene under the regulation of the cytomegalovirus promoter.

Assay

HEK-293 cells were seeded at 40,000 cells/well in 96 well plates in Dulbecco's modified Eagle medium (high glucose) containing 10% charcoal stripped fetal calf serum, 100 units/ml Penicillin G and 100 μg/ml Streptomycin sulfate at 37° C. in a humidified atmosphere of 5% $CO_2$. After 24 h, transfections were performed with Lipofectamine (Gibco-BRL, Gaithersburg, Md.) according to the instructions of the manufacturer. In general, transfection mixes contained 0.002 μg of LXRα/GAL4 or LXRβ/GAL4 chimeric expression vectors, 0.02 μg of reporter vector pUAS(5×)-tk-luc and 0.034 μg of pEGFP-N1 vector as an internal control of transfection efficiency. Compounds were characterized by incubation with transfected cells for 48 h across a range of concentrations. Cell lysates were prepared from washed cells using Cell Lysis Buffer (Promega) according to the manufacturer's directions. Luciferase activity in cell extracts was determined using Luciferase Assay Buffer (Promega) in a ML3000 luminometer (Dynatech Laboratories). GFP expression was determined using the Tecan Spectrofluor Plus at excitation wavelength of 485 nm and emission at 535 nm. Luciferase activity was normalized to GFP expression to account for any variation in efficiency of transfection.

Results with representative tested compounds of Formula I for LXRα transactivation having an $EC_{50}$ of $\leq 5{,}500$ nM for at least one of the LXRα receptor or the LXRβ receptor, and preferred tested compounds having an $EC_{50}$ of 1,000 nM or less for at least one of the LXRα receptor or the LXRβ receptor.

EXAMPLE 3

To assess the relevant biological activity of the LXR agonists, certain compounds were tested for their ability to increase cholesterol efflux from cultured human cells, as described by Sparrow et al., *JBC* volume 277, pages 10021–10027, Mar. 22, 2002. Caco-2 cells, which are of human origin, were obtained from ATCC and grown in Opti-MEM (Gibco #51985-034) containing 10% FCS, non-essential amino acids (Gibco #11140-050), and vitamins (Gibco # 11120-052). Caco-2 cells were plated at 100,000 cells/well in 48-well plates. After four days the cells had reached confluence, and were then labeled with $^3$H-cholesterol by incubation for 24 hours in fresh growth media containing $^3$H-cholesterol (10 μCi/ml). Following labeling with $^3$H-cholesterol, cells were washed and incubated an additional 24 hours in serum-free media containing 1 mg/ml BSA, to allow for equilibration of $^3$H-cholesterol with intracellular cholesterol. Cholesterol efflux was initiated by adding 10 μg/ml apoA-I, with or without compound, in serum-free medium. Compounds were added to cell culture medium from DMSO solutions, and control cells received an equivalent amount of DMSO, never exceeding 0.1%. After 24 hours, media were harvested and cells dissolved in 0.1 M NaOH. Media were briefly centrifuged to remove non-adherent cells, and then aliquots of both the supernatants and the dissolved cells were subjected to liquid scintillation spectrometry to determine radioactivity. Cholesterol efflux is expressed as a percentage, calculated as ($^3$H-cholesterol in medium/($^3$H-cholesterol in medium+$^3$H-cholesterol in cells))×100.

Table 1 shows cholesterol efflux results for the compound made in Example 16. Results are given as mean and SEM of quadruplicate incubations.

TABLE 1

| Compound concentration (nM) | % cholesterol efflux | p value |
|---|---|---|
| 0 | 2.8 ± 0.3 | |
| 1 | 3.2 ± 0.3 | p = NS |
| 10 | 4.0 ± 0.2 | p = 0.01 |
| 100 | 8.8 ± 0.7 | p < 0.001 |
| 1000 | 10.3 ± 0.3 | p < 0.001 |
| 5000 | 6.6 ± 0.4 | p < 0.001 |

Table 2 shows cholesterol efflux results the compound made in Example 25. Results are given as mean and SEM of quadruplicate incubations.

TABLE 2

| Compound concentration (nM) | % cholesterol efflux | p value |
|---|---|---|
| 0 | 3.0 ± 0.1 | |
| 1 | 3.4 ± 0.3 | p = NS |
| 10 | 3.5 ± 0.09 | p = NS |
| 100 | 4.5 ± 0.09 | p < 0.002 |
| 1000 | 4.6 ± 0.09 | p < 0.002 |
| 5000 | 5.2 ± 0.2 | p < 0.002 |

EXAMPLE 4

Step 1: Preparation of 2,4-dihydroxy-3-propyl-1',1',1'-trifluoroacetophenone.

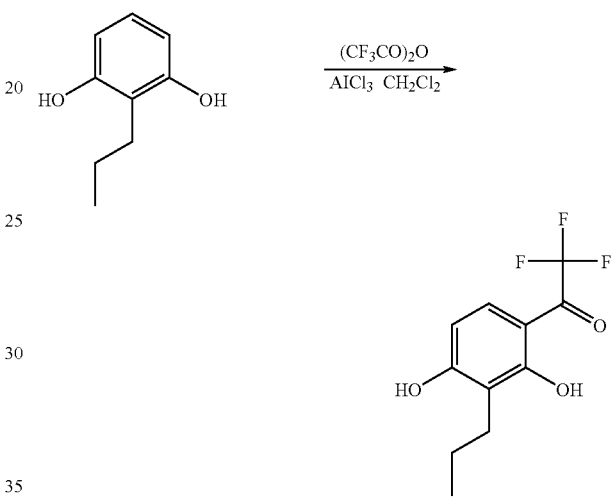

A solution of 2-propylresorcinol (5.0 grams) and trifluoroacetic anhydride (9.6 mL) in 1,2-dichloroethane (30.0 mL) was treated with aluminum chloride (4.38 grams). This mixture was stirred overnight. The reaction mixture was partitioned between methylene chloride and water. The organic phase was dried over sodium sulfate and filtered. The solvent was evaporated and the resulting solid was recrystallized from methylene chloride and cyclohexane (1:1) to give the title compound.

Selected Signals: $^1$H NMR (CDCl$_3$) δ 7.59 (d, 1H), 6.24 (d, 1H), 5.92 (s, 1H), 2.63 (t, 2H), 1.74 (s, 1H), 1.58 (m, 2H), 0.98 (t, 3H).

Step 2: Preparation of 3-trifluoromethyl-7-propyl-6-hydroxybenzisoxazole.

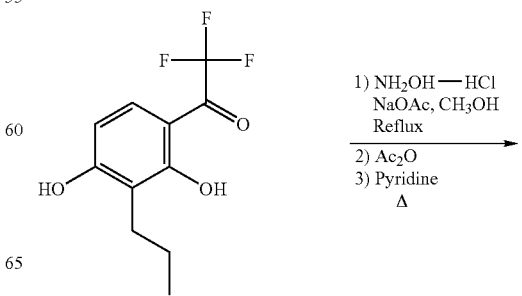

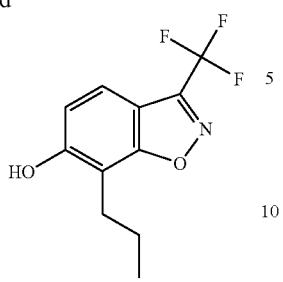

A mixture of 2,4-dihydroxy-3-propyl-1',1',1'-trifluoroacetophenone (2.5 grams), sodium acetate (4.18 grams), hydroxylamine hydrochloride (3.59 grams) and methanol (80 mL) was heated under reflux overnight. The solvent was then evaporated and the resulting solid was partitioned between ethyl acetate and pH 7 buffer. The organic phase was separated and washed with brine. The organic phase was dried over sodium sulfate and the solvent was evaporated to give an oil. The oil was then dissolved in acetic anhydride. The solution was stirred for two hours, then the acetic anhydride was evaporated in vacuo. The residue was partitioned between ethyl acetate and pH 7 buffer and the organic phase was dried over sodium sulfate. The organic phase was evaporated to give an oil. The oil was dissolved in pyridine and refluxed overnight. The solvent was evaporated in vacuo to give an oil which was chromatographed on silica gel using ethyl acetate and hexane (1:4) to give the title compound.

Selected Signals: $^1$H NMR (CDCl$_3$) δ 7.46 (d, 1H), 6.92 (d, 1H), 5.42 (bs, 1H), 2.89 (t, 2H), 1.74 (m, 2H), 0.98 (t, 3H).

EXAMPLE 5

Preparation of 6-hydroxy-3-neopentyl-7-propyl-1,2-benzisoxazole.

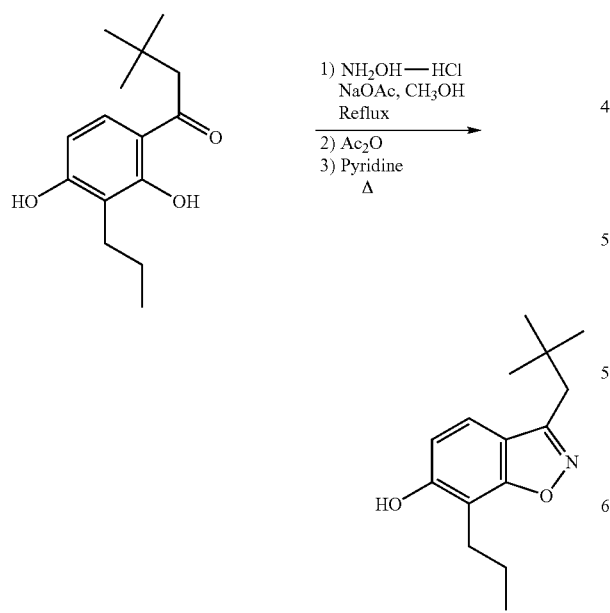

1-(2,4-dihydroxy-3-propylphenyl)-3,3-dimethylbutan-1-one (200 grams, 0.8 mole), prepared as in Example 4 Step 1 from 3,3-dimethylbutanoic acid anhydride, was converted to 6-hydroxy-3-neopentyl-7-propyl-1,2-benzisoxazole, as described in Example 4 Step 2, using hydroxylamine hydrochloride (278 grams, 4 mole) and sodium acetate (320 grams) and refluxing in methanol (2.5 L). A second addition of hydroxylamine hydrochloride (106 grams, 1.5 mole) and sodium acetate (250 grams) was made after 18 hours at reflux followed by further heating under reflux for a total of 36 hours. After isolation of the oxime, as described in Example 4 Step 2, the crude material was purified by crystallization from hexanes. Conversion to the oxime acetate was accomplished by dissolving in acetic anhydride, as described in Example 4 Step 2. Full conversion required 18 hours for this case. Ring closure in pyridine, as in Example 4 Step 2, yielded a dark oil. The crude product was eluted from silica gel with methylene chloride. The resulting oil was crystallized from hexanes:ether to yield the title compound.

Selected Signals: $^1$H NMR (CDCl$_3$) δ 7.33 (d, 1H, J=8.5 Hz), 6.81 (d, 1H, J=8.5 Hz), 5.07 (brd, 1H), 2.89 (collapsed dd, 2H), 1.77 (sect, 2H, J=7.5 Hz), 1.08 (s, 9H), 1.04 (t, 3H, J=7.3 Hz).

EXAMPLE 6

Step 1: Preparation of 2,4-dihydroxy-3-allylbenzophenone.

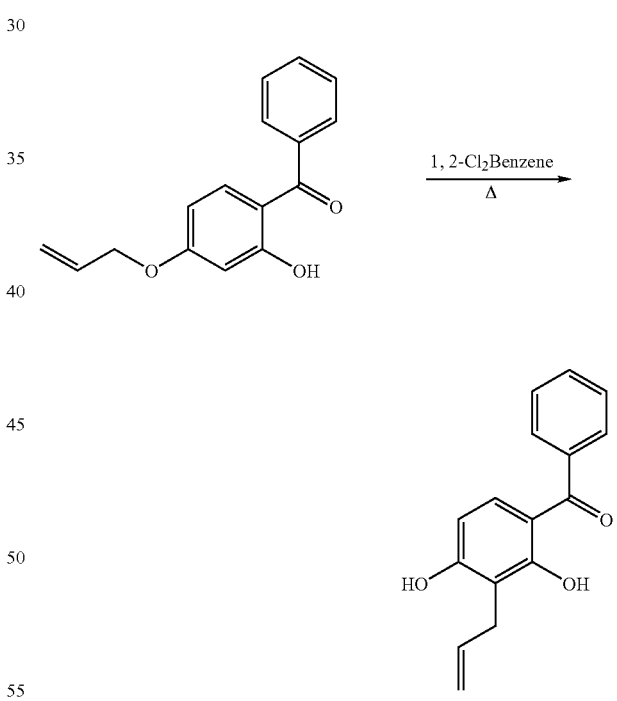

Commercially available 4-allyloxy-2-hydroxybenzophenone (15 grams) was rearranged by heating under reflux in ortho-dichlorobenzene (60 mL) for 26 hours. The product was isolated by dilution of the reaction mixture with 5 volumes hexanes to give the title compound.

Selected Signals: $^1$H NMR (CDCl$_3$); δ 7.62–7.59 (m, 2H), 7.56–7.52 (m, 2H), 7.49–7.44 (m, 2H), 7.40 (d, 1H, J=8.9 Hz), 6.34 (d, 1H, J=8.8 Hz), 6.02 (ddt, 1H, J=17.21, 10.1, 6.2 Hz), 5.72 (s, 1H, phenol OH), 5.14–5.24 (m, 2H), 3.53 (d with fine splitting, 2H, J=6.2 Hz).

Step 2: Preparation of 2,4-dihydroxy-3-propylbenzophenone.

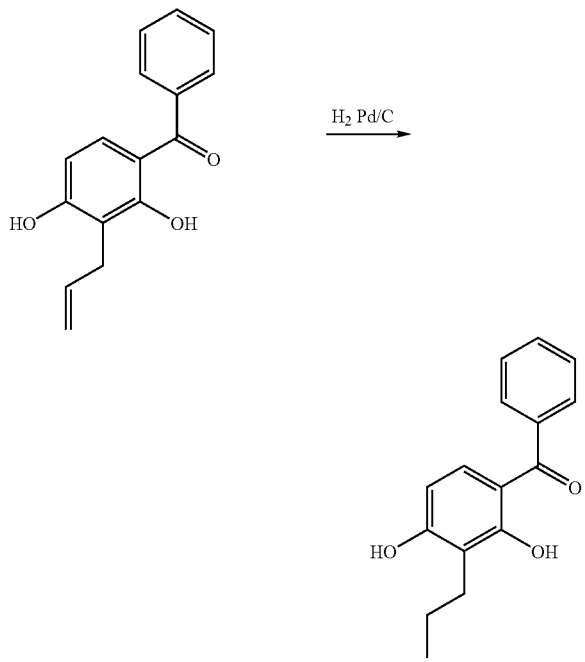

A solution of 2,4-dihydroxy-3-(2-propenyl)benzophenone (3 grams) was reduced under ~1 atmosphere of H₂ in ethyl acetate (100 mL) over 10% Pd/C catalyst (0.3 grams) for 3 hours. The product was purified by crystallization from methanol/water to give the title compound.

Selected Signals: $^1$H NMR (CDCl$_3$); δ 7.61–7.59 (m, 2H), 7.55–7.51 (m, 1H), 7.48–7.44 (m, 2H), 7.33 (d, 1H, J=8.8 Hz), 6.29 (d, 1H, J=8.8 Hz), 5.51 (s, 1H, phenol OH), 2.66 (dd, 2H, J=7.6, 9.3 Hz), 1.61 (sext, 2H, J=7.7 Hz), 0.99 (t, 3H, J=7.3 Hz).

Step 3: Preparation of 6-hydroxy-7-propyl-3-phenylbenzisoxazole.

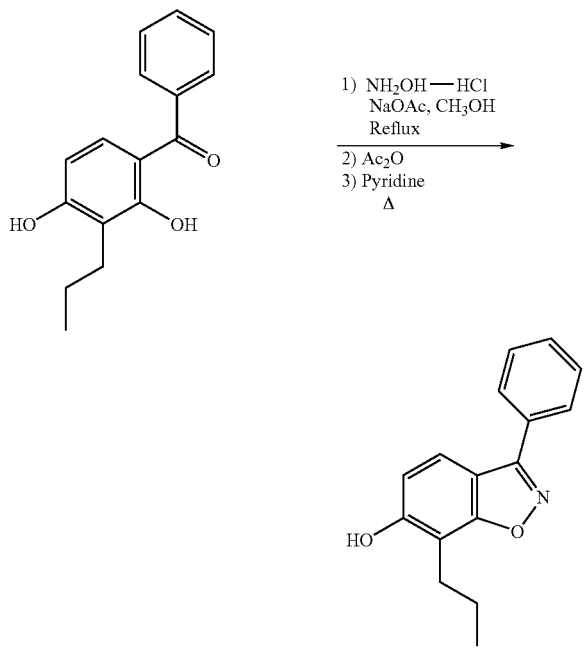

The 2,4-dihydroxy-3-propylbenzophenone (2.5 grams, 9.8 mmol) was converted to the oxime with hydroxylamine hydrochloride (2.7 grams, 39 mmol) and sodium acetate (3.21 grams, 39 mmol), as described in Example 4 Step 2. The oxime was purified by elution from a silica gel column with 97:3 toluene:ethyl acetate. The product oxime was further treated, as in Example 4 Step 2, with acetic anhydride (15 mL) and subsequently heated under reflux in pyridine (15 mL).

The cooled reaction mixture was poured into 2 N hydrochloric acid and ethyl acetate. The aqueous phase was extracted with ethyl acetate and washed with saturated aqueous sodium bicarbonate, followed by saturated aqueous sodium chloride. The ethyl acetate extracts were dried over sodium sulfate and reduced in vacuo. The residue was taken up in refluxing toluene (50 mL) and cooled to RT to give the title compound.

Selected Signals: $^1$H NMR (CDCl$_3$); δ 7.92–7.89 (m, 2H), 7.57 (d, 1H, J=8.5 Hz), 7.55–7.49 (m, 3H), 6.86 (d, 1H, J=8.6 Hz), 5.14 (s, 1H, phenol OH), 2.90 (dd, 2H, J=8.9, 7.6 Hz), 1.76 (sext, 2H, J=7.5 Hz), 1.01 (t, 3H, J=7.3 Hz). MS CI NH$_3$ M+1 254.1.

EXAMPLE 7

Preparation of 7-propyl-3-(trifluoromethyl)-6-(3-bromopropyloxy)-1,2-benzisoxazole.

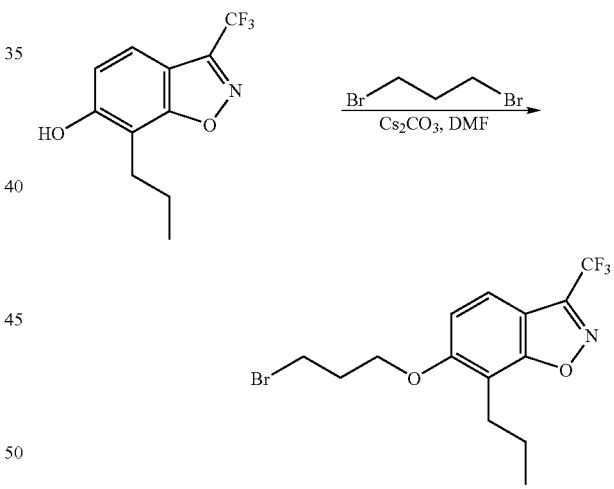

To a DMF solution (50 mL) of 6-hydroxy-7-propyl-3-(trifluoromethyl)-1,2-benzisoxazole as prepared in Example 4 step 2 (5 grams, 20.4 mmol) was added 1,3-dibromopropane (10 mL, 98.5 mmol), followed by cesium carbonate (10 grams, 30.7 mmol). The mixture was stirred at room temperature overnight. After aqueous ether work-up and silica gel chromatography (hexanes: 2.5% ethyl acetate), the title compound was obtained.

Selected Signals: $^1$H NMR (CDCl$_3$); δ 7.59 (d, 2H, J=8.8 Hz), 7.10 (d, 2H, J=8.8 Hz), 4.27 (t, 2H, J=5.8 Hz), 3.66 (t, 2H, J=6.4 Hz), 2.93 (t, 2H, J=7.5 Hz), 2.41 (pent, 2 H, J=6.0 Hz), 1.72 (sext, 2H, J=7.5 Hz), 0.99 (t, 3H, J=7.5 Hz).

EXAMPLE 8

Preparation of 7-propyl-3-(trifluoromethyl)-6-(4-bromobutyloxy)-1,2-benzisoxazole.

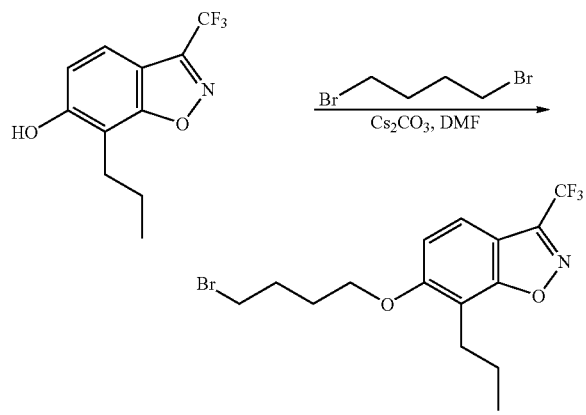

To a DMF solution (50 mL) of 6-hydroxy-7-propyl-3-(trifluoromethyl)-1,2-benzisoxazole as prepared in Example 4 step 2 (6.5 gram, 26.5 mmol) was added 1,4-dibromobutane (16 mL, 133 mmol), followed by cesium carbonate (9.1 grams, 27.8 mmol). The mixture was stirred at room temperature overnight. After aqueous/ether work-up and silica gel chromatography (hexanes: 2.5% ethyl acetate), the title compound was obtained.

Selected Signals: $^1$H NMR (CDCl$_3$); δ 7.54 (d, 1H, J=8.7 Hz), 7.04 (d, 1H, J=8.7 Hz), 4.14 (t, 2H, J=5.9 Hz), 3.52 (t, 2H, J=6.6 Hz), 2.91 (collapsed dd, 2H, J=7.5 Hz), 2.1 (m, 2H), 2.03 (m, 2H), 1.69 (sext, 2H, J=7.5 Hz), 0.966 (t, 3H, J=7.4 Hz). MS ESI M+1 380/382 isotope doublet.

EXAMPLE 9

Preparation of 7-propyl-3-neopentyl-6-(3-bromopropyloxy)-1,2-benzisoxazole.

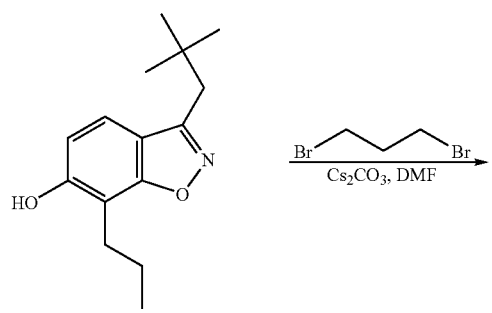

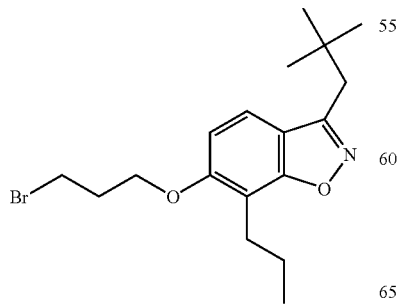

7-propyl-3-neopentyl-6-(3-bromopropyloxy)-1,2-benzisoxazole was prepared from 7-propyl-3-neopentyl-1,2-benzisoxazole as for Example 7 above.

Selected Signals: $^1$H NMR (CDCl$_3$); δ 7.06 (d, 1H, J=8.8 Hz), 6.53 (d, 1H, J=8.5 Hz), 3.61 (t, 2H, J=5.9 Hz), 3.08 (t, 2H, J=6.4 Hz), 2.92 (collapsed dd, 2H, J=7.5 Hz), 2.82 (t, 2H, J=6.3 Hz), 2.64 (s, 2H), 1.70 (m, 2H, J=6.3 Hz), 0.946 (s, 9H), 0.884 (t, 3H, J=7.3 Hz).

EXAMPLE 10

Preparation of 1-(3-{[7-propyl-3-(neopentyl)-1,2-benzisoxazol-6-yl]oxy}propyl)-pyrrolidine-2,5-dione.

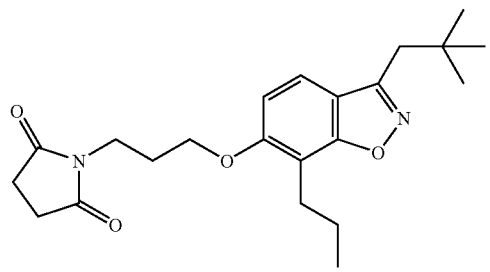

Pyrrolidine-2,5-dione (17 mg, 0.172 mmol) and 7-propyl-3-neopentyl-6-(3-bromopropyloxy)-1,2-benzisoxazole, from Example 9 above, (42 mg, 0.114 mmol) were combined in DMF (7 ml) with Cs$_2$CO$_3$ (56 mg, 0.17 mmol) at room temperature. The mixture was stirred 18 hours. The mixture was diluted with 2 ml H$_2$O and acidified with TFA. The resulting mixture was purified by elution from a RP-18 reversed phase HPLC column with a 90:10 to 0:100 H$_2$O:CH$_3$CN gradient to yield 1-(3-{[7-propyl-3-(neopentyl)-1,2-benzisoxazol-6-yl]oxy}propyl)pyrrolidine-2,5-dione.

Selected Signals: $^1$H NMR (400 MHz; CD$_3$OD) δ 7.51 (d, 1H, J=8.7 Hz), 7.03 (d, 1H, J=8.8 Hz), 4.11 (t, 2H, J=6.0 Hz), 3.74 (t, 2H, J=7.0 Hz), 2.89 (collapsed dd, 2H, J=7.6 Hz), 2.82 (s, 2H), 2.68 (s, 4H), 2.07 (pent, 2H, J=6.8 Hz), 1.70 (sext, 2H, J=7.6 Hz), 1.03 (2, 9H), 0.971 (t, 3H, J=7.3 Hz).

EXAMPLE 11

Preparation of 1-(3-{[7-propyl-3-(trifluoromethyl)-1,2-benzisoxazol-6-yl]oxy}propyl)pyrrolidine-2,5-dione.

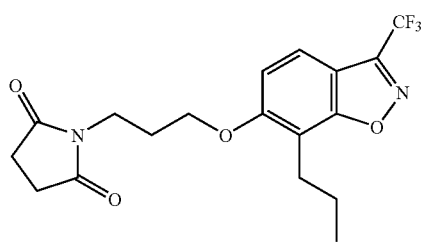

1-(3-{[7-propyl-3-(trifluoromethyl)-1,2-benzisoxazol-6-yl]oxy}propyl)-pyrrolidine-2,5-dione was prepared as for Example 10 from pyrrolidine-2,5-dione and the bromide from Example 7. After aqueous work-up and silica gel chromatography, the title compound was obtained.

Selected Signals: $^1$H NMR (400 MHz; D$_6$-Benzene) δ 7.13 (d, 1H, J obscured), 6.41 (d, 1H, J=8.8 Hz), 3.41 (2 overlapping triplets, 4 H, J=6.4, 6.1 Hz), 2.88 (collapsed dd, 2H), 1.74 (pent, 2H, J=7.2 Hz), 1.69 (sext, 2H, J=7.4 Hz), 1.62 (s, 4H), 0.93 (t, 3H, J=7.4 Hz).

EXAMPLE 12

Preparation of 2-(3-{[7-propyl-3-(trifluoromethyl)-1,2-benzisoxazol-6-yl]oxy}propyl)-1H-isoindole-1,3(2H)-dione.

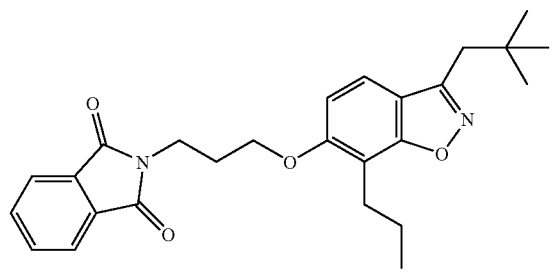

2-(3-{[7-propyl-3-(trifluoromethyl)-1,2-benzisoxazol-6-yl]oxy}propyl)-1H-isoindole-1,3(2H)-dione was prepared as for Example 10 from phthalimide and the bromide from Example 9. After aqueous work-up and silica gel chromatography, the title compound was obtained.

Selected Signals: $^1$H NMR (400 MHz; CD$_3$OD) δ 7.84–7.81 (m, 2H); 7.80–7.77 (m, 2H); 7.50 (d, 1H, J=8.8 Hz); 7.03 (d, 1H, J=8.8 Hz); 4.17 (t, 2H, J=5.6 Hz); 3.94 (t, 2H, 6.6 Hz); 2.81 (s, 2H); 2.74 (t, 2H, J=7.6 Hz); 2.21 (pentet, 2H, J=6.2 Hz); 1.63 (sextet, 2H, J=7.5 Hz); 1.02 (s, 9H); 0.91 (t, 3H, J=7.2 Hz).

EXAMPLE 13

Preparation of 3,3-dimethyl-1-(3-{[7-propyl-3-(trifluoromethyl)-1,2-benzisoxazol-6-yl]oxy}propyl)pyrrolidine-2,5-dione.

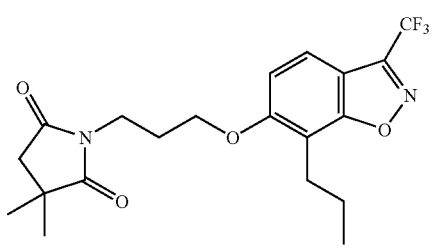

3,3-Dimethyl-1-(3-{[7-propyl-3-(trifluoromethyl)-1,2-benzisoxazol-6-yl]oxy}propyl)pyrrolidine-2,5-dione was prepared as for Example 10 from 3,3-dimethylpyrrolidine-2,5-dione and the bromide from Example 7. After aqueous work-up and silica gel chromatography, the title compound was obtained.

Selected Signals: $^1$H NMR (500 MHz; CDCl$_3$) δ 7.55 (d, 1H, J=9.0 Hz), 7.02 (d, 1H, J=8.5 Hz), 4.09 (t, 2H, J=6.2 Hz), 3.74 (t, 2H, J=7.0 Hz), 2.94 (t, 2H, J=7.5 Hz), 2.56 (s, 2H), 2.14 (pent, 2H, J=6.8 Hz), 1.72 (sext, 2H, J=7.3 Hz), 1.32 (s, 6H), 0.98 (t, 3H, J=7.2 Hz).

EXAMPLE 14

Preparation of 3-methyl-3-phenyl-1-(3-{[7-propyl-3-(trifluoromethyl)-1,2-benzisoxazol-6-yl]oxy}propyl)pyrrolidine-2,5-dione.

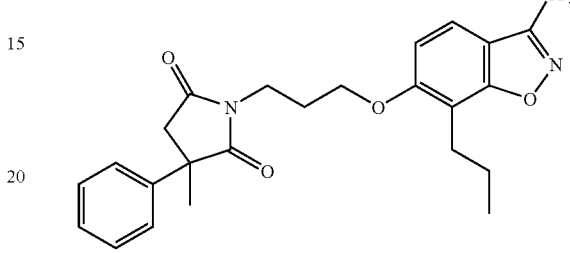

3-Methyl-3-phenyl-1-(3-{[7-propyl-3-(trifluoromethyl)-1,2-benzisoxazol-6-yl]oxy}propyl)pyrrolidine-2,5-dione was prepared as for Example 10 from 3-methyl-3-phenylpyrrolidine-2,5-dione and the bromide from Example 7. After aqueous work-up and silica gel chromatography, the title compound was obtained.

Selected Signals: $^1$H NMR (400 MHz; CDCl$_3$) δ 7.55 (d, 1H, J=8.8 Hz); 7.35–7.27 (m, 5H); 6.99 (d, 1H, J=8.8 Hz); 4.10 (t, 2H, J=6.2); 3.84 (td, 2H, J$_1$=7.3 Hz, J$_2$=1.2 Hz); 3.16 (d, 1H, J=18.4 Hz); 2.94 (t, 2H, J=7.4 Hz); 2.88 (d, 1H, J=18.4 Hz); 2.20 (pentet, 2H, J=6.6 Hz); 1.73 (sextet, 2H, J=7.5 Hz); 1.73 (s, 3H); 0.99 (t, 3H, J=7.4 Hz).

EXAMPLE 15

Preparation of 3-(3-{[7-propyl-3-(neopentyl)-1,2-benzisoxazol-6-yl]oxy}propyl)thiazolidine-2,4-dione.

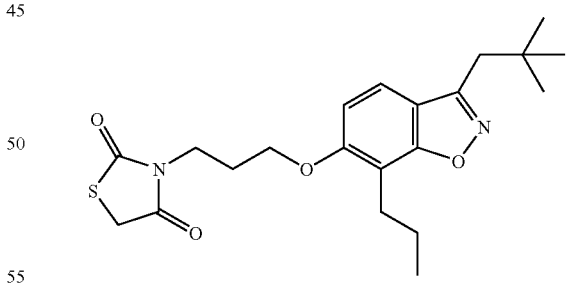

3-(3-{[7-propyl-3-(neopentyl)-1,2-benzisoxazol-6-yl]oxy}propyl)thiazolidine-2,4-dione was prepared as for Example 10 from thiazolidine-2,4-dione and the bromide from Example 9. After aqueous work-up and silica gel chromatography, the title compound was obtained.

Selected Signals: $^1$H NMR (400 MHz; C$_6$D$_6$) δ 7.07 (d, 1H, J=8.4 Hz); 6.54 (d, 1H, J=8.4 Hz); 3.50 (t, 2H, J=5.8 Hz); 3.45 (t, 2H, J=7.2 Hz); 3.02 (t, 2H, J=7.6 Hz); 2.75 (s, 2H); 2.63 (s, 2H); 1.80 (sextet, 2H, J=7.5); 1.70 (pentet, 2H, J=7.0 Hz); 0.99 (t, 3H, J=7.4 Hz); 0.94 (s, 9H).

EXAMPLE 16

Preparation of 3-(3-{[7-propyl-3-(trifluoromethyl)-1,2-benzisoxazol-6-yl]oxy}propyl)thiazolidine-2,4-dione.

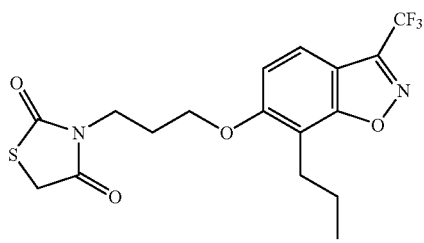

3-(3-{[7-propyl-3-(trifluoromethyl)-1,2-benzisoxazol-6-yl]oxy}propyl)thiazolidine-2,4-dione was prepared as for Example 10 from thiazolidine-2,4-dione and the bromide from Example 7. After aqueous work-up and silica gel chromatography, the title compound was obtained.

Selected Signals: $^1$H NMR (400 MHz; $C_6D_6$) δ 6.34 (d, 1H, J=8.8 Hz); 3.39 (t, 2H, J=7.2 Hz); 3.29 (t, 2H, J=5.8 Hz); 2.86 (t, 2H, J=7.6 Hz); 2.71 (s, 2H); 1.68 (sextet, 2H, J=7.5 Hz); 1.62 (pentet, 2H, J=6.5 Hz); 0.93 (t, 3H, J=7.4 Hz).

EXAMPLE 17

Preparation of 5,5-dimethyl-3-(3-{[7-propyl-3-(neopentyl)-1,2-benzisoxazol-6-yl]oxy}propyl)thiazolidine-2,4-dione.

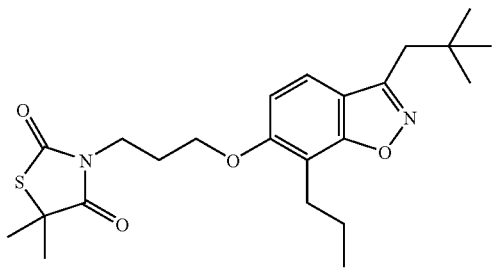

5,5-Dimethyl-3-(3-{[7-propyl-3-(neopentyl)-1,2-benzisoxazol-6-yl]oxy}propyl)thiazolidine-2,4-dione was prepared as for Example 10 from 5,5-dimethylthiazolidine-2,4-dione and the bromide from Example 9. After aqueous work-up and silica gel chromatography, the title compound was obtained.

Selected Signals: $^1$H NMR (400 MHz; $C_6D_6$) δ 7.05 (d, 1H, J=8.4 Hz); 6.54 (d, 1H, 8.8 Hz); 3.57 (t, 2H, J=4.0 Hz); 3.50 (t, 2H, J=6.0 Hz); 3.05 (t, 2H, J=7.6 Hz); 2.62 (s, 2H); 1.83–1.72 (m, 4H); 1.13 (s, 6H); 0.9 (t, 3H, J=7.4 Hz); 0.92 (s, 9H).

EXAMPLE 18

Preparation of [2,4-dioxo-3-(3-{[7-propyl-3-(neopentyl)-1,2-benzisoxazol-6-yl]oxy}propyl)-1,3-thiazolidin-5-yl]acetic acid.

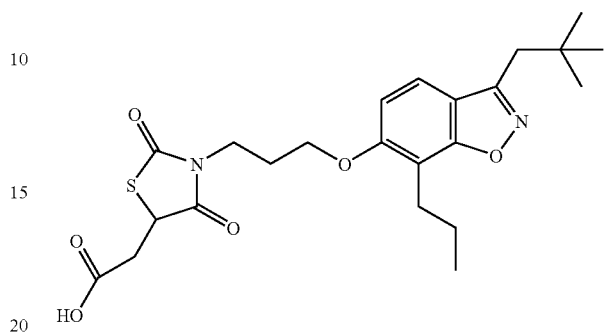

t-Butyl [2,4-dioxo-3-(3-{[7-propyl-3-(neopentyl)-1,2-benzisoxazol-6-yl]oxy}propyl)-1,3-thiazolidin-5-yl]acetate was prepared as for Example 10 from t-butyl 1,3-thiazolidin-5-ylacetate and the bromide from Example 9. Ester cleavage with formic acid followed by evaporation of the solvent and silica gel chromatography yielded the title compound.

Selected Signals: $^1$H NMR (400 MHz; $CD_3OD$) δ 7.52 (d, 1H, J=8.8 Hz); 7.04 (d, 1H, J=8.8 Hz); 4.56 (dd, 1H, $J_1$=7.4 Hz, $J_2$=3.8 Hz); 4.13 (t, 2H, J=5.8 Hz); 3.86 (td, $J_1$=6.9 Hz, $J_2$=2.0 Hz); 3.15 (dd, 1H, $J_1$=17.8 Hz, $J_2$=2.0 Hz); 3.02 (dd, 1H, $J_1$=17.8 Hz, $J_2$=7.6 Hz); 2.89 (t, 2H, 4.9 Hz); 2.82 (s, 2H); 2.13 (pentet, 2H, J=6.4 Hz); 1.69 (sextet, 2H, J=7.5 Hz); 1.03 (s, 9H); 0.97 (t, 3H, J=7.4 Hz).

EXAMPLE 19

Preparation of 3-(3-{[7-propyl-3-(neopentyl)-1,2-benzisoxazol-6-yl]oxy}propyl)imidazolidine-2,4-dione.

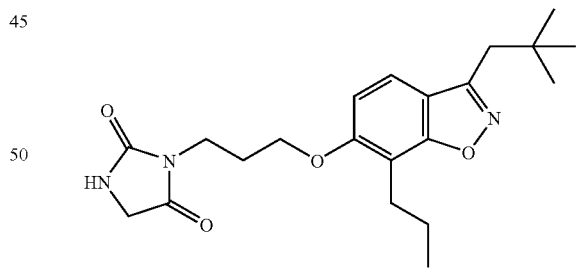

3-(3-{[7-propyl-3-(neopentyl)-1,2-benzisoxazol-6-yl]oxy}propyl)imidazolidine-2,4-dione was prepared as for Example 10 from imidazolidine-2,4-dione and the bromide from Example 9. After aqueous ether work-up and silica gel chromatography, the title compound was obtained.

Selected Signals: $^1$H NMR (400 MHz; $CDCl_3$) δ 7.37 (d, 1H, J=8.8 Hz); 6.90 (d, 2H, J=8.8 Hz); 5.93 (s, 1H); 4.11 (t, 2H, J=6.0 Hz); 3.98 (s, 2H); 3.79 (t, 2H, J=7.0 Hz); 2.90 (t, 2H, J=7.6 Hz); 2.82 (s, 2H); 2.20 (pentet, 2H, J=6.6 Hz); 1.72 (sextet, 2H, J=7.52 Hz); 1.06 (s, 9H); 1.01 (t, 3H, J=7.4 Hz).

EXAMPLE 20

Preparation of 3-(3-{[7-Propyl-3-(trifluoromethyl)-1,2-benzisoxazol-6-yl]oxy}propyl)imidazolidine-2,4-dione.

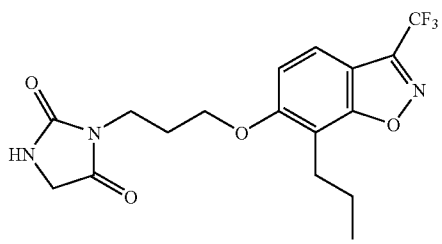

3-(3-{[7-Propyl-3-(trifluoromethyl)-1,2-benzisoxazol-6-yl]oxy}propyl)imidazolidine-2,4-dione was prepared as for Example 10 from imidazolidine-2,4-dione and the bromide from Example 7. After aqueous ether work-up and silica gel chromatography, the title compound was obtained.

Selected Signals: $^1$H NMR (500 MHz; CDCl$_3$) δ 7.58 (d, 1H, J=9.0 Hz); 7.07 (d, 1H, J=9.0 Hz); 5.30 (s, 1H); 4.17 (t, 2H, J=6.0 Hz); 4.01 (s, 2H); 3.82 (t, 2H, J=7.0 Hz); 2.96 (t, 2H, J=7.5 Hz); 2.24 (pent, 2H, J=6.8 Hz); 1.75 (sext, 2H, J=7.5 Hz); 1.01 (t, 3H, J=7.5 Hz).

EXAMPLE 21

Preparation of 1-methyl-3-(3-{[7-propyl-3-(trifluoromethyl)-1,2-benzisoxazol-6-yl]oxy}propyl)imidazolidine-2,4-dione.

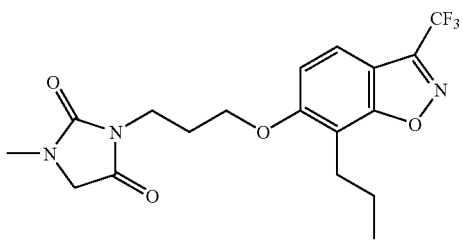

1-Methyl-3-(3-{[7-propyl-3-(trifluoromethyl)-1,2-benzisoxazol-6-yl]oxy}propyl)imidazolidine-2,4-dione was prepared as for Example 10 from 1-methylimidazolidine-2,4-dione and the bromide from Example 7. After aqueous work-up and silica gel chromatography, the title compound was obtained.

Selected Signals: $^1$H NMR (500 MHz; CDCl$_3$) δ 7.55 (d, 1H, J=8.5 Hz), 7.04 (d, 1H, J=9.0 Hz), 4.13 (t, 2H, J=6.0 Hz), 3.87 (s, 2H), 3.76 (t, 2H, J=6.8 Hz), 3.00 (s, 3H), 2.92 (t, 2H, J=7.5 Hz), 2.19 (pent, 2H, J=6.5 Hz), 1.71 (sext, 2H, J=7.5 Hz), 0.98 (t, 3H, J=7.5 Hz).

EXAMPLE 22

Preparation of 5(R)-methyl-3-(3-{[7-propyl-3-(trifluoromethyl)-1,2-benzisoxazol-6-yl]oxy}propyl)imidazolidine-2,4-dione.

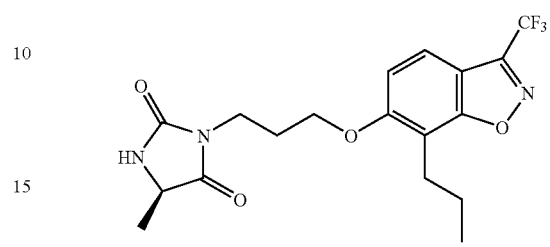

5(R)-Methyl-3-(3-{[7-propyl-3-(trifluoromethyl)-1,2-benzisoxazol-6-yl]oxy}propyl)imidazolidine-2,4-dione was prepared as for Example 10 from 5(R)-methylimidazolidine-2,4-dione and the bromide from Example 7. After aqueous work-up and silica gel chromatography, the title compound was obtained.

Selected Signals: $^1$H NMR (500 MHz; CD$_3$OD) δ 7.63 (d, 1H, J=9.0 Hz), 7.25 (d, 1H, J=9.0 Hz), 4.18 (t, 2H, J=5.8 Hz), 4.09 (q, 1H, J=6.8 Hz), 3.73 (td, J=7.0, 2.2 Hz), 2.95 (t, 2H, J=7.5 Hz), 2.15 (pent, 2H, J=6.0 Hz). 1.73 (sext, 2H, J=7.5 Hz), 1.35 (d, 3H, J=7.0 Hz), 0.98 (t, 3H, J=7.5 Hz).

EXAMPLE 23

Preparation of 5,5-dimethyl-3-(3-{[7-propyl-3-(trifluoromethyl)-1,2-benzisoxazol-6-yl]oxy}propyl)imidazolidine-2,4-dione.

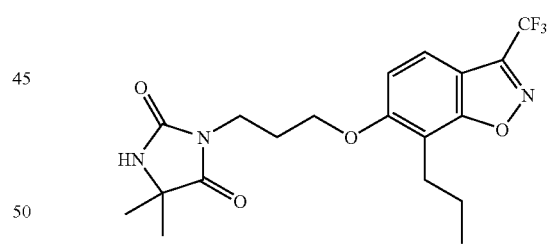

5,5-Dimethyl-3-(3-{[7-propyl-3-(trifluoromethyl)-1,2-benzisoxazol-6-yl]oxy}propyl)imidazolidine-2,4-dione was prepared as for Example 10 from 5,5-dimethylimidazolidine-2,4-dione and the bromide from Example 7. After aqueous work-up and silica gel chromatography, the title compound was obtained.

Selected Signals: $^1$H NMR (500 MHz; CDCl$_3$) δ 7.57 (d, 1H, J=8.5 Hz), 7.06 (d, 1H, J=8.5 Hz), 5.69 (s, 1H), 4.14 (t, 2H, J=6.0 Hz), 3.78 (t, 2H, J=7.0 Hz), 2.97 (t, 2H, J=7.5 Hz), 2.22 (pent, 2H, J=6.5 Hz), 1.75 (sext, 2H, J=7.5 Hz), 1.45 (s, 6H), 1.01 (t, 3H, J=7.2 Hz). MS: m/z=414 (M+H).

EXAMPLE 24

Preparation of 1-(2-pyridyl)-3-(3-{[7-propyl-3-(trifluoromethyl)-1,2-benzisoxazol-6-yl]oxy}propyl)imidazolidine-2,4-dione.

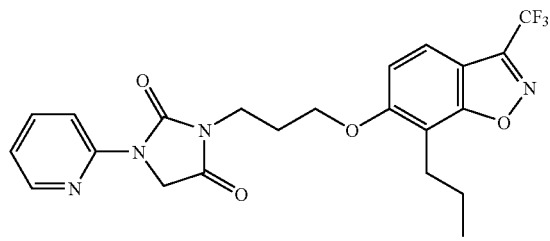

To solution of 2-aminopyridine (5.36 g) in CH$_2$Cl$_2$ (500 mL) at 0° C. was added chloroacetylisocyanate (5.9 mL). After several seconds, a thick white precipitate formed. After 5 minutes, 0.5 mL H$_2$O was added, and the solvent was removed in vacuo to yield of 3-chloroacetyl-1-(2-pyridyl)-urea. To 3-chloroacetyl-1-(2-pyridyl)-urea (1.26 g) in DMF (100 mL) was added Cs$_2$CO$_3$ (4.84 g) and 1,3-dibromopropane (1.2 mL). The mixture was let stand overnight, and then poured into 200 mL H$_2$O. The aqueous phase was extracted with 350 mL. EtOAc, combined organic layers were washed with with brine, and the solvent removed in vacuo to yield an off-white solid. This was slurried in CH$_2$Cl$_2$ and vacuum filtered. The filtrate was adsorbed onto silica gel, and the solvent removed in vacuo to trap product for separation. The product was separated using column chromatography (30% EtOAc in hexanes) to yield 1-(3-bromopropyl)-3-(2-pyridyl)-imidazolidinedione as a white solid.

A mixture of 7-propyl-3-trifluoromethyl-6-hydroxy-1,2-benzisoxazole from Example 7 (417 mg), 1-(3-bromopropyl)-3-(2-pyridyl)-imidazolidinedione (672 mg), and Cs$_2$CO$_3$ (867 mg) in DWF was allowed to react for 24 hours at RT. The mixture was filtered, then separated by preparative HPLC to yield the title compound as a white solid.

Selected Signals: $^1$H NMR (500 MHz; CDCl$_3$) δ 8.32 (dd, 1H, J1=4.5 Hz, 1.0 Hz); 8.20 (d, 1H, J=8.5 Hz); 7.73–7.69 (m, 1H); 7.55 (d, 1H, J=8.5 Hz); 7.07–7.04 (m, 2H); 4.55 (s, 2H); 4.18 (t, 2H, J=6.2 Hz); 3.88 (t, 2H, J=7.0 Hz); 2.91 (t, 2H, J=7.5 Hz); 2.26 (pentet, 2H, J=6.5 Hz); 1.71 (sextet, 2H, J=7.5 Hz); 0.96 (t, 3H, J=7.2 Hz). MS: m/z=463 (M+H).

EXAMPLE 25

Preparation of rac-5-methyl-5-phenyl-3-(3-{[7-propyl-3-(trifluoromethyl)-1,2-benzisoxazol-6-yl]oxy}propyl)imidazolidine-2,4-dione.

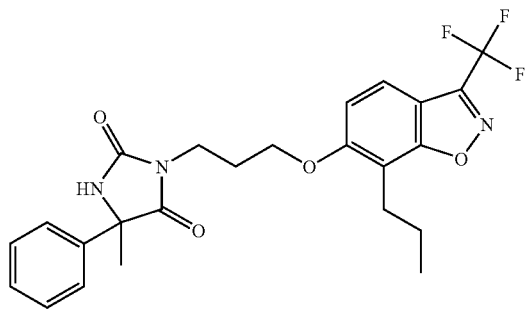

rac-5-Methyl-5-phenyl-3-(3-{[7-propyl-3-(trifluoromethyl)-1,2-benzisoxazol-6-yl]oxy}propyl)imidazolidine-2,4-dione was prepared as for Example 10 from 5-methyl-5-phenylimidazolidine-2,4-dione and the bromide from Example 7. After aqueous work-up and silica gel chromatography, the title compound was obtained.

Selected Signals: $^1$H NMR (400 MHz; CDCl$_3$) δ 7.49 (m, 2H), 7.39 (m, 3H), 6.95 (d, 1H, J=8.8 Hz), 5.97 (brd, 1H), 4.08 (t, 2H, J=6.1 Hz), 3.79 (dt, 2H, J=6.8, 2.5 Hz), 2.92 (t, 2H, J=7.5 Hz), 2.19 (m, 2H), 1.72 (sext, 2H, J=7.5 Hz), 0.975 (t, 3H, J=7.5 Hz).

EXAMPLE 26

Preparation of rac-5-methyl-5-phenyl-3-(3-{[7-propyl-3-(neopentyl)-1,2-benzisoxazol-6-yl]oxy}propyl)imidazolidine-2,4-dione.

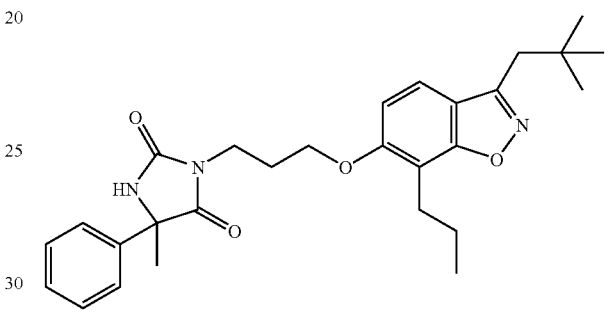

rac-5-Methyl-5-phenyl-3-(3-{[7-propyl-3-(neopentyl)-1,2-benzisoxazol-6-yl]oxy}propyl)imidazolidine-2,4-dione was prepared as for Example 10 from 5-methyl-5-phenylimidazolidine-2,4-dione and the bromide from Example 9. After aqueous work-up and silica gel chromatography, the title compound was obtained.

Selected Signals: $^1$H NMR (400 MHz; CDCl$_3$) δ 7.50–7.48 (m, 2H); 7.41–7.31 (m, 4H); 6.83 (d, 1H, J=8.8); 6.26 (s, 1H); 4.05 (t, 2H, J=6.0 Hz); 3.79 (t, 2H, J=7.0 Hz); 2.88 (t, 2H, J=7.4 Hz); 2.82 (s, 2H); 2.18 (pentet, 2H, J=6.5 Hz); 1.84 (s, 3H); 1.71 (sextet, 2H, J=7.6 Hz); 1.06 (s, 9H); 0.98 (t, 3H, J=7.4 Hz).

EXAMPLE 27

Preparation of rac-5-methyl-5-phenyl-3-(3-{[7-propyl-3-(phenyl)-1,2-benzisoxazol-6-yl]oxy}propyl)imidazolidine-2,4-dione.

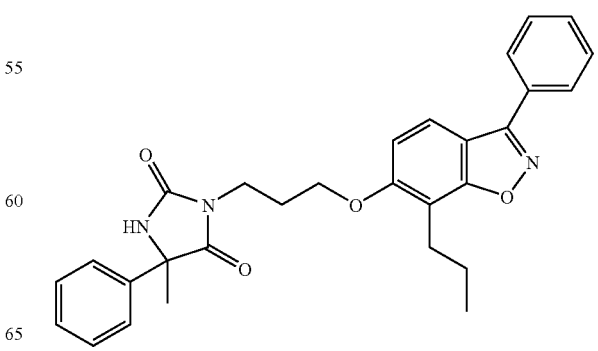

rac-5-Methyl-5-phenyl-3-(3-{[7-propyl-3-(phenyl)-1,2-benzisoxazol-6-yl]oxy}propyl)imidazolidine-2,4-dione was prepared as for Example 10 from 5-methyl-5-phenylimidazolidine-2,4-dione and the appropriate bromide. The bromide, 7-propyl-3-phenyl-6-(3-bromopropyloxy)-1,2-benzisoxazole, was prepared as for Example 7 using the 7-propyl-3-phenyl-6-hydroxy-1,2-benzisoxazole prepared in Example 6.

Selected Signals: $^1$H NMR (400 MHz; CDCl$_3$) δ 7.96–7.93 (m); 7.63 (d, 1H, J=8.8 Hz); 7.59–7.54 (m); 7.52–7.48 (m); 6.91 (d, 1H, J=8.8 Hz); 6.15 (s, 1H); 4.09 (t, 2H, J=6.2 Hz); 3.80 (t, 2H, J=7.2 Hz); 2.94 (t, 2H, J=7.4 Hz); 2.20 (pentet, 2H, J=6.6 Hz); 1.84 (s, 2H); 1.75 (sextet, 2H, J=7.5 Hz); 1.00 (t, 3H, J=7.2 Hz).

EXAMPLE 28

Preparation of rac-5-methyl-5-phenyl-3-(3-{[7-propyl-3-(trifluoromethyl)-1,2-benzisoxazol-6-yl]oxy}butyl)imidazolidine-2,4-dione.

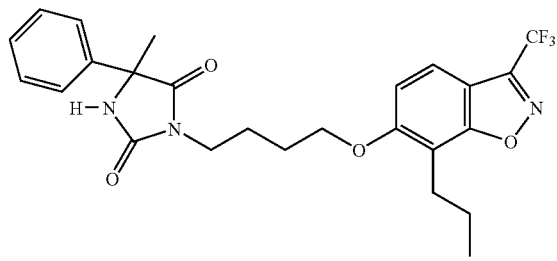

rac-5-Methyl-5-phenyl-3-(3-{[7-propyl-3-(trifluoromethyl)-1,2-benzisoxazol-6-yl]oxy}butyl)imidazolidine-2,4-dione was prepared as for Example 10 from 5-methyl-5-phenylimidazolidine-2,4-dione and the bromide from Example 8. After aqueous work-up and silica gel chromatography (toluene: 10% acetone), the title compound was obtained.

Selected Signals: $^1$H NMR (400 MHz; CDCl$_3$) δ 7.52 (m, 3H), 7.4 (m, 3H), 7.02 (d, 1H, J=9 Hz), 4.11 (t, 2H, J=5.6 Hz), 3.64 (t, 2H, J=6.5 Hz), 2.89 (t, 2H, J=7.5 Hz), 1.86 (s, 3H), 1.68 (sext, 2H, J=7.5 Hz), 0.944 (t, 3H, J=7.5 Hz).

EXAMPLE 29

Preparation of rac-5-methyl-5-(3-carboxyphenyl)-3-(3-{[7-propyl-3-(trifluoromethyl-1,2-benzisoxazol-6-yl]oxy}propyl)imidazolidine-2,4-dione.

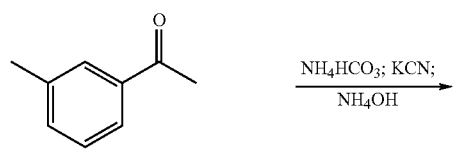

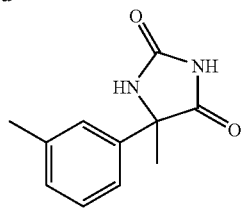

KMnO$_4$; NaOH; 95° C.

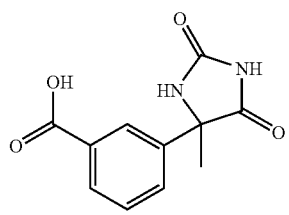

To a solution of 930 mg 3'-methylacetophenone in 5 mL anhydrous ethanol was added 2.04 g NH$_4$HCO$_3$, 542 mg KCN, then 2.1 mL conc. NH$_4$OH. The mixture was stirred at 60° C. overnight. Addition of water and partial solvent removal induced crystallization. The product was vacuum filtered and washed several times with water. The resultant white solid was recrystallized from MeOH to yield 5-methyl-5-(3-methylphenyl)-imidazolidine-2,4-dione as a white solid. A solution of 351 mg of the imidazolidinedione product, 822 mg KMnO$_4$ and 1.44 g NaOH in 20 mL H$_2$O was heated to 95° C. for 2 hours, then allowed to cool to RT. Ethanol (5 mL) was added to decompose the remaining KMnO$_4$, and the mixture filtered, acidified, and left to stand overnight. The fine precipitate that formed was recovered by gravity filtration to yield, after drying in vacuo, 5-methyl-5-(3-carboxyphenyl)-imidizalodine-2,4-dione as an off-white solid.

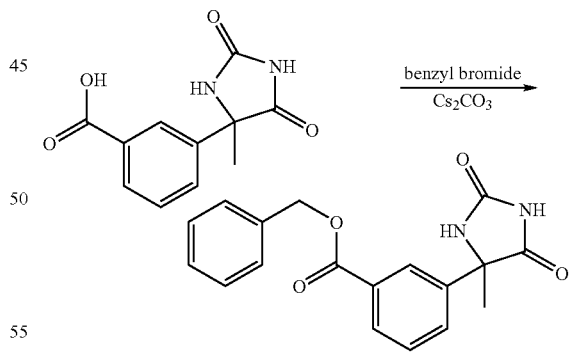

benzyl bromide
Cs$_2$CO$_3$

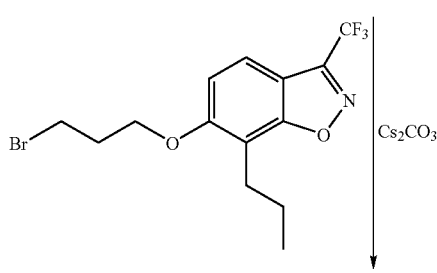

Cs$_2$CO$_3$

-continued

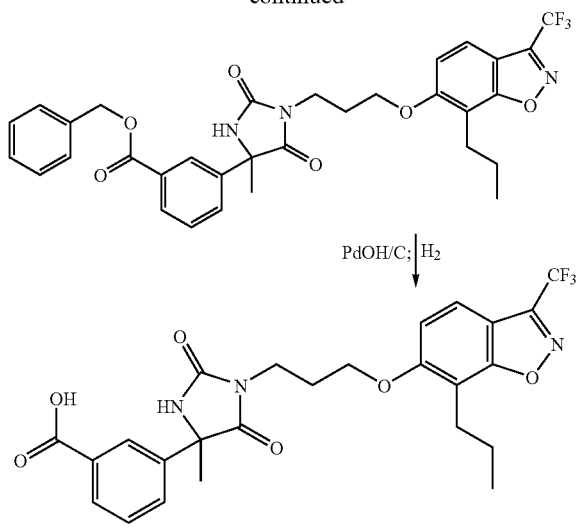

To a solution of 77 mg of 5-methyl-5-(3-carboxyphenyl)-imidizalodine-2,4-dione in 5 mL DMF was added 112 mg Cs$_2$CO$_3$ and 45 μL benzyl bromide. The mixture was left to react overnight, and then 1.0 mL H$_2$O was added, and the soluble components were separated by preparative scale HPLC to afford the benzyl ester of the above acid.

To 23 mg of the ester in 3 mL DMF was added 31.3 mg 7-propyl-3-(trifluoromethyl)-6-(3-bromopropyloxy)-1,2-benzisoxazole, and 38.9 mg Cs$_2$CO$_3$. The mixture was allowed to react overnight, and then 0.4 mL H$_2$O was added. The soluble components were separated by preparative scale HPLC, to yield the benzyl ester of the desired product as a white solid. Reduction of this material in methanol using H$_2$ and PdOH/C was complete within an hour, and after purification by preparative HPLC, the title compound was obtained.

Selected Signals: $^1$H NMR (500 MHz; CD$_3$OD) δ 8.16 (s, 1H), 7.89 (d, 1H, J=8.5 Hz), 7.74 (d, 1H, J=7.5 Hz), 7.54 (d, 1H, J=8.5 Hz), 7.42 (t, 1H, J=8.0 Hz), 7.08 (s, 1H, J=9.0 Hz), 4.14–4.04 (m, 2H), 3.84–3.71 (m, 2H), 2.88 (t, 2H, J=7.5 Hz), 2.19–2.13 (m, 2H), 1.77 (s, 3H), 1.69 (sext, 2H, J=7.3 Hz), 0.96 (t, 3H, J=7.5 Hz). MS: m/z=520 (M+H).

EXAMPLE 30

Preparation of rac-5-methyl-5-(4-pyridyl)-3-(3-{[7-propyl-3-(trifluoromethyl)-1,2-benzisoxazol-6-yl]oxy}propyl)imidazolidine-2,4-dione.

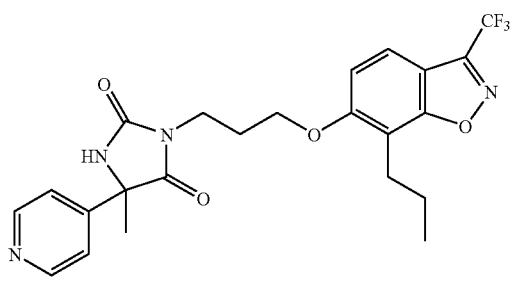

A mixture of 4-acetyl pyridine (3.0 mL), NH$_4$HCO$_3$ (7.73 g), KCN (2.16 g), and concentrated NH$_4$OH (8.2 mL) in EtOH (10.35 mL) was heated to 60° C. overnight under a reflux condenser. The reaction mixture was extracted with ether, then acidified to pH 4.5 with concentrated HCl and extracted with EtOAc. The combined organic extracts from the acidic extraction were dried over Na$_2$SO$_4$. Solvent was removed in vacuo to yield crude 5-methyl-5-(4-pyridyl)-imidazolidinedione as an off-white solid.

A mixture of crude rac-5-methyl-5-(4-pyridyl)-imidazolidinedione (29 mg), 7-propyl-3-trifluoromethyl-6-(3-bromopropyloxy)-1,2-benzisoxazole (27 mg) from Example 7, and Cs$_2$CO$_3$ (71 mg) in DMF (3.0 mL) was allowed to react overnight. Water (0.4 mL) was added and the resulting mixture separated by HPLC to yield the title compound as a clear oil.

Selected Signals: $^1$H NMR (500 MHz; CDCl$_3$) δ 8.84 (d, 2H, J=5.5 Hz), 8.07 (d, 2H, 6.0 Hz), 7.56 (d, 1H, 8.5 Hz), 7.01 (d, 1H, J=9.0 Hz), 4.11 (t, 2H, J=5.8 Hz), 4.02 (b), 3.83 (t, 2H, J=7.2 Hz), 2.94 (t, 2H, J=7.2 Hz), 2.21 (pentet, 2H, J=6.8 Hz), 1.90 (s, 3H), 1.73 (sextet, 2H, J=7.5 Hz), 0.99 (t, 3H, J=7.2 Hz). MS: m/z=477 (M+H).

EXAMPLE 31

Preparation of rac-5-methyl-5-(3-pyridyl)-3-(3-{[7-propyl-3-(trifluoromethyl)-1,2-benzisoxazol-6-yl]oxy}propyl)imidazolidine-2,4-dione.

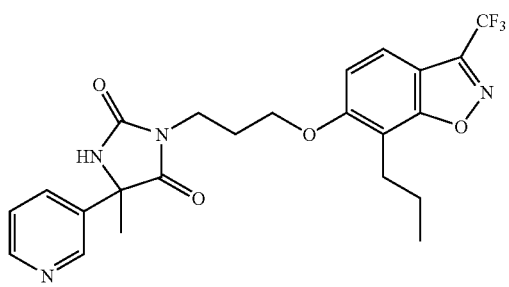

rac-5-Methyl-5-(3-pyridyl)-3-(3-{[7-propyl-3-(trifluoromethyl)-1,2-benzisoxazol-6-yl]oxy}propyl)imidazolidine-2,4-dione was prepared as for Example 30 starting from 3-acetylpyridine.

Selected Signals: $^1$H NMR (500 MHz; CD$_3$OD) δ 8.94 (s, 1H), 8.71 (d, 1H, J=5.5 Hz), 8.58 (dt, 1H, J=8.5, 1.8 Hz), 7.88 (dd, 1H, J=8.0, 5.5 Hz), 7.60 (d, 1H, J=8.5 Hz); 7.18 (d, 1H, J=9.0 Hz), 4.18–4.10 (m, 2H), 3.81–3.75 (m, 2H), 2.91 (t, 2H, J=7.5 Hz), 2.17 (pentet, 2H, J=6.0 Hz), 1.83 (s, 3H), 1.71 (sextet, 2H, J=7.5 Hz), 0.96 (t, 3H, J=7.5 Hz). MS: m/z=477 (M+H).

EXAMPLE 32

Preparation of rac-5-methyl-5-(2-pyridyl)-3-(3-{[7-propyl-3-(trifluoromethyl)-1,2-benzisoxazol-6-yl]oxy}propyl)imidazolidine-2,4-dione.

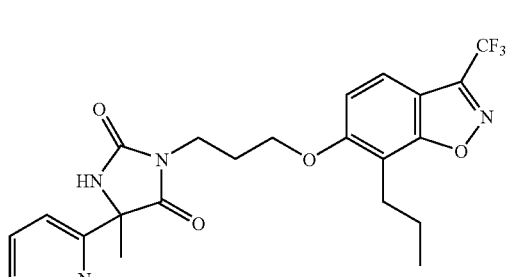

rac-5-Methyl-5-(2-pyridyl)-3-(3-{[7-propyl-3-(trifluoromethyl)-1,2-benzisoxazol-6-yl]oxy}propyl)imidazolidine-2,4-dione was prepared as for Example 30 starting from 2-acetylpyridine.

Selected Signals: $^1$H NMR (500 MHz; CDCl$_3$) δ 8.66 (d, 1H, J=5.0 Hz), 7.86 (td, 1H, J=8.0,1.8 Hz), 7.82 (d, 1H, J=8.0 Hz), 7.53 (d, 1H, J=8.5 Hz), 7.42–7.41 (m, 1H), 7.02 (d, 1H, J=9.0 Hz), 4.16–4.08 (m, 2H), 3.87–3.82 (m, 2H), 2.91 (t, 2H, J=7.5 Hz), 2.22 (pent, 2H, J=6.8 Hz), 1.85 (s, 3H), 1.71 (sext, 2H, J=7.5 Hz), 0.98 (t, 3H, J=7.2 Hz). MS: m/z=477 (M+H).

EXAMPLE 33

Separation of the Active Enantiomer of 5-Methyl-5-(2-pyridyl)-3-(3-{[7-propyl-3-(trifluoromethyl)-1,2-benzisoxazol-6-yl]oxy}propyl)imidazolidine-2,4-dione.

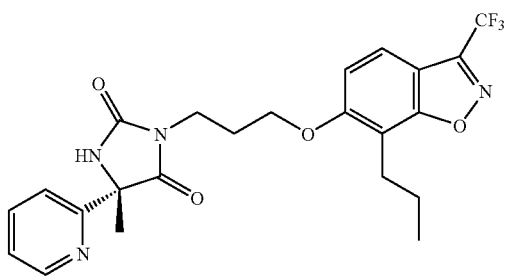

The racemic product prepared in Example 32 was separated using chiral stationary phase HPLC (Chiracell AD column; 30% iPA in pentane) to yield the active enantiomer as the first eluting compound.

EXAMPLE 34

Preparation of 3-(3-{[7-propyl-3-(trifluoromethyl)-1,2-benzisoxazol-6-yl]oxy}propyl)-1-pyrimidin-2-ylimidazolidine-2,4-dione.

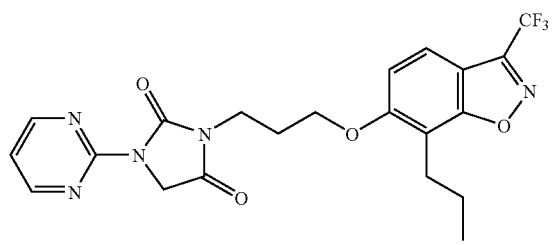

3-(3-{[7-Propyl-3-(trifluoromethyl)-1,2-benzisoxazol-6-yl]oxy}propyl)-1-pyrimidin-2-ylimidazolidine-2,4-dione was prepared as for Example 24 above starting from 2-aminopyrimidine.

Selected Signals: $^1$H NMR (500 MHz; CDCl$_3$) δ 8.63 (d, 2H, J=5.0 Hz), 7.54 (d, 1H, J=8.5 Hz), 7.10 (t, 1H, J=4.8 Hz), 7.04 (d, 1H, J=9.0 Hz), 4.54 (s, 2H), 4.18 (t, 2H, J=6.0 Hz), 3.90 (t, 2H, J=7.0 Hz), 2.91 (t, 2H, J=7.5 Hz), 2.27 (pent, 2H, J=6.5 Hz), 1.70 (sext, 2H, J=7.5 Hz), 0.95 (t, 3H, J=7.5 Hz). MS: m/z=464 (M+H).

EXAMPLE 35

Preparation of 3-(3-{[7-propyl-3-(trifluoromethyl)-1,2-benzisoxazol-6-yl]oxy}propyl)-1-pyrazin-2-ylimidazolidine-2,4-dione.

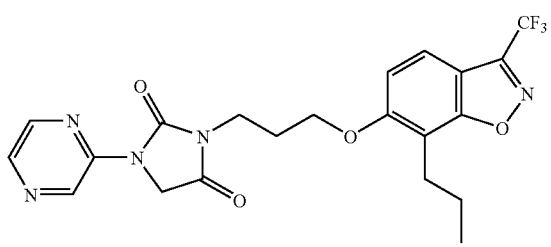

3-(3-{[7-Propyl-3-(trifluoromethyl)-1,2-benzisoxazol-6-yl]oxy}propyl)-1-pyrazin-2-ylimidazolidine-2,4-dione was prepared as for Example 24 above starting from 2-aminopyrazine.

Selected Signals: $^1$H NMR (500 MHz; CDCl$_3$) δ 9.60 (s, 1H); 8.38 (s, 1H); 8.31 (s, 1H); 7.57 (d, 1H, J=9.0 Hz); 7.07 (d, 1H, J=8.5 Hz); 4.52 (s, 2H); 4.21 (t, 2H, J=6.0 Hz); 3.93 (t, 2H, J=7.0 Hz); 2.93 (t, 2H, J=7.5 Hz); 2.30 (pentet, 2H, J=6.5 Hz); 1.73 (sextet, 2H, J=7.5 Hz); 0.98 (t, 3H, J=7.2 Hz). MS: m/z=464 (M+H).

EXAMPLE 36

Preparation of rac-3-[2,5-dioxo-4-phenyl-1-(3-{[7-propyl-3-(trifluoromethyl)-1,2-benzisoxazol-6-yl]oxy}propyl)imidazolidin-4-yl]propanoic acid.

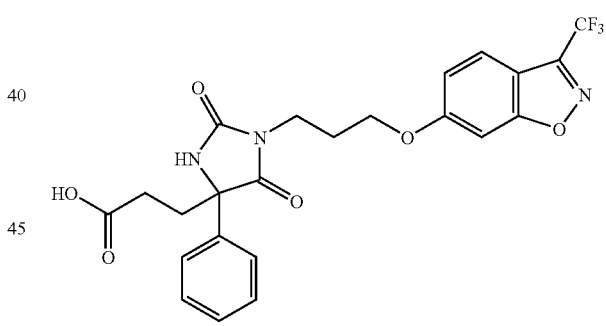

A mixture of 3-benzoylpropionic acid (2.26 g), NH$_4$HCO$_3$ (3.63 g), and KCN (1.03 g) in a solution of 5 mL EtOH and 4 mL conc. NH$_4$OH was heated to 60 C in an oil bath under a reflux condenser overnight. Water was added and the mixture extracted with ether, acidified with concentrated HCl, extracted with EtOAc and then CH$_2$Cl$_2$. The extracts of the acidified aqueous were reduced in vacuo to yield crude 2,5-dioxo-4-phenylimidazolidin-4-yl]propanoic acid.

A mixture of 7-propyl-3-trifluoromethyl-6-(3-bromopropyloxy)-1,2-benzisoxazole (54 mg), crude 2,5-dioxo-4-phenylimidazolidin-4-yl]propanoic acid (56 mg), and Cs$_2$CO$_3$ (95 mg) in 3.0 mL DMF was allowed to react overnight. After aqueous workup, the mixture was separated by preparative scale TLC (40% EtOAc in hexanes with 1% MeOH added) to give the titled compound.

Selected Signals: $^1$H NMR (400 MHz; CDCl$_3$) δ 8.25 (s, 1H); 7.58 (d, 1H, J=8.5 Hz); 7.54–7.52 Hz (m, 2H);

7.43–7.35 (m,4H); 7.06 (d, 1H, J=9.0 Hz); 4.32 (td, 2H, J$_1$=6.2 Hz, J$_2$=1.3 Hz); 4.16 (t, 2H, J=6.0 Hz); 2.92 (t, 2H, J=7.5 Hz); 2.53 (t, 2H, J=7.0 Hz); 2.45–2.35 (m, 2H); 2.18 (p, 2H, J=6.5 Hz); 1.71 (sextet, 2H, 7.5 Hz); 0.97 (t, 3H, J=7.5 Hz).

EXAMPLE 37

Preparation of 4-[5,5-dimethyl-2,4-dioxo-3-(3-{[7-propyl-3-(trifluoromethyl)-1,2-benzisoxazol-6-yl]oxy}propyl)imidazolidin-1-yl]butanoic acid.

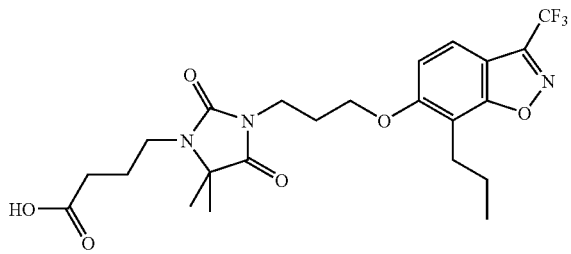

A mixture of 5,5-dimethylhydantoin (5.25 g), 1-bromo-3-chloropropane (8.5 mL), and Cs$_2$CO$_3$ (20.78 g) in 40 mL DMF was allowed to react overnight. The reaction was poured into 125 mL H$_2$O, extracted with ether, and the combined extracts dried over MgSO$_4$. The crude extract was filtered, then reduced in vacuo to yield a clear oil. The residue was chromatographed (50% EtOAc in hexanes) to yield 3-(3-chloropropyl)-5,5-dimethylimidazolidinedione as a white solid.

To a solution of 3-(3-chloropropyl)-5,5-dimethylimidazolidinedione (109 mg), in DMF (5.0 mL) at 0 C was added 1.0 M lithium hexamethyldisilazide (0.64 mL, in hexanes). After 5 minutes, ethyl 4-bromobutyrate (0.23 mL) was added, and the mixture allowed to warm gradually to RT overnight. Water (10 mL) was added and the mixture extracted with ether. Combined ether extracts were dried over MgSO$_4$, filtered and reduced in vacuo. The residue was separated by HPLC to yield 1-alkylated product, ethyl 4-[5,5-dimethyl-2,4-dioxo-3-(3-bromopropyl)imidazolidin-1-yl]butanoate, as a clear oil.

A mixture of the 1-alkylated product (45 mg), 7-propyl-3-trifluoromethyl-6-(3-bromopropyloxy)-1,2-benzisoxazole from Example 7 (36 mg), and Cs$_2$CO$_3$ (104 mg) in 4.0 mL DMF was allowed to react overnight. The reaction mixture was filtered, then separated by HPLC to yield ethyl 4-[5,5-dimethyl-2,4-dioxo-3-(3-{[7-propyl-3-(trifluoromethyl)-1,2-benzisoxazol-6-yl]oxy}propyl)imidazolidin-1-yl]butanoate as a clear oil. To a solution of 13 mg of the ethyl ester in 1.0 mL EtOH was added 0.45 mL H$_2$O and 3 mg KOH. The mixture was allowed to react overnight, then diluted to 4 mL with 50% aqueous CH$_3$CN. The solution was separated by preparative BPLC to yield the title compound.

Selected Signals: $^1$H NMR (500 MHz; CDCl$_3$) δ 7.56 (d, 1H, J=9.0 Hz), 7.06 (d, 1H, J=9.0 Hz), 4.13 (t, 2H, J=6.2 Hz), 3.77 (t, 2H, J=7.2 Hz), 3.36 (t, 2H, J=7.5 Hz), 2.95 (t, 2H, J=7.5 Hz), 2.46 (t, 2H, J=7.2 Hz), 2.20 (pent, 2H, J=6.8 Hz), 1.98 (pent, 2H, J=7.5 Hz), 1.74 (sext, 2H, J=7.5 Hz), 1.42 (s, 6H), 0.99 (t, 3H, J=7.5 Hz). MS: m/z=500 (M+H).

EXAMPLE 38

Preparation of 4-[5,5-dimethyl-2,4-dioxo-3-(3-{[7-propyl-3-(trifluoromethyl)-1,2-benzisoxazol-6-yl]oxy}propyl)imidazolidin-1-yl]pentanoic acid.

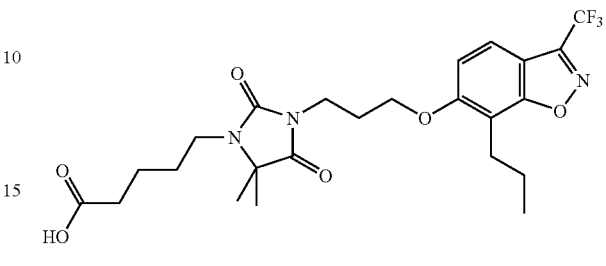

4-[5,5-Dimethyl-2,4-dioxo-3-(3-{[7-propyl-3-(trifluoromethyl)-1,2-benzisoxazol-6-yl]oxy}propyl)imidazolidin-1-yl]pentanoic acid was prepared as for Example 37, substituting 5-bromovalerate for the 4-bromobutyrate of Example 37.

Selected Signals: $^1$H NMR (500 MHz; CDCl$_3$) δ 7.56 (d, 1H, J=9.0 Hz), 7.06 (d, 1H, J=9.0 Hz), 4.13 (t, 2H, J=6.0 Hz), 3.77 (t, 2H, J=7.0 Hz), 3.30 (t, 2H, J=7.0 Hz), 2.95 (t, 2H, J=7.0 Hz), 2.42 (t, 2H, J=6.8 Hz), 2.21 (pent, 2H, J=6.8 Hz), 1.76–1.70 (m, 6H), 1.40 (s, 6H), 1.00 (t, 3H, J=7.5 Hz). MS: m/z=514 (M+H).

EXAMPLE 39

Preparation of 1-(3-{[7-propyl-3-(trifluoromethyl)-1,2-benzisoxazol-6-yl]oxy}propyl)imidazolidin-2-one.

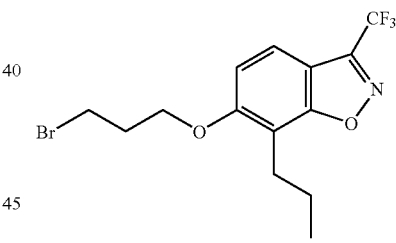

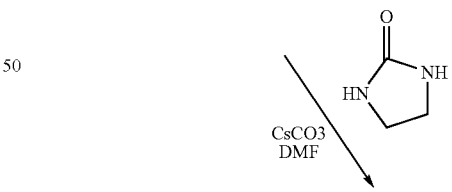

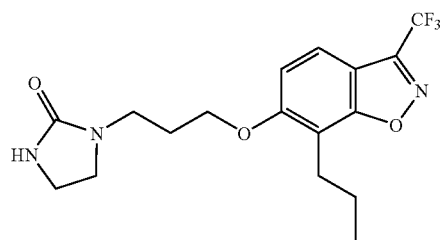

To a DMF solution (5 mL) of 7-propyl-3-(trifluoromethyl)-6-(3-bromopropyloxy)-1,2-benzisoxazole as prepared in Example 7 (322 mg, 0.88 mmol), was added 2-imidazolidinone (320 mg, 3.52 mmol) and CsCO₃ (320 mg, 0.97 mmol) then stirred at room temperature overnight. After aqueous work-up and silica gel chromatography (hexanes: 70% ethyl acetate), the title compound was obtained.

Selected Signals: ¹H NMR (CDCl₃) δ 7.57 (d, 1H, J=9 Hz), 7.08 (d, 1H, J=9 Hz), 4.28 (s, 1H) 4.18 (t, 2H, J=6.5 Hz), 3.49 (m, 2H), 3.47 (m, 4H), 2.95 (t, 2H, J=7.5 Hz), 2.12 (m, 2H), 1.75 (m, 2H), 0.96 (t, 3H, J=7 Hz). MS: m/z=372 (M+H)

EXAMPLE 40

Preparation of methyl 2-[2-oxo-3-(3-{[7-propyl-3-(trifluoromethyl)-1,2-benzisoxazol-6-yl]oxy}propyl)imidazolidin-1-yl]propanoate.

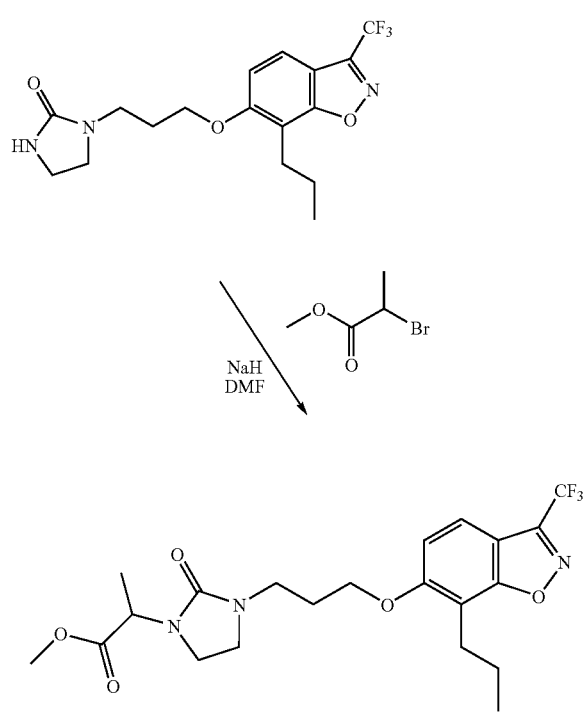

To a DMF solution (2 mL) of 1-(3-{[7-propyl-3-(trifluoromethyl)-1,2-benzisoxazol-6-yl]oxy}propyl)imidazolidin-2-one as prepared in Example 39 (10 mg, 0.027 mmol), was added NaH (4.3 mg, 1.08 mmol) and stirred at room temperature for 30 minutes. Methyl 2-bromopropionate (27 mg, 0.16 mmol) was added and the mixture stirred for another 3 hour. After aqueous work-up and silica gel chromatography (hexanes:70% ethyl acetate), the title compound was obtained.

Selected Signals: ¹H NMR (CDCl₃) δ 7.57 (d, 1H, J=9 Hz), 7.09 (d, 1H, J=9 Hz), 4.67 (q, 1H, J=7.5 & 14.5 Hz), 4.17 (t, 2H, J=7.5 Hz), 3.7 (s, 3H), 3.39–3.51 (m, 6H), 2.94 (t, 2H, J=7.5 Hz), 2.10 (m, 2H), 1.75 (m, 2H), 1.43 (d, 3H, J=7.5 Hz), 0.98 (t, 3H, J=7.0 Hz). MS: m/z=458 (M+H)

EXAMPLE 41

Preparation of 2-[2-oxo-3-(3-{[7-propyl-3-(trifluoromethyl)-1,2-benzisoxazol-6-yl]oxy}propyl)imidazolidin-1-yl]propanoic acid.

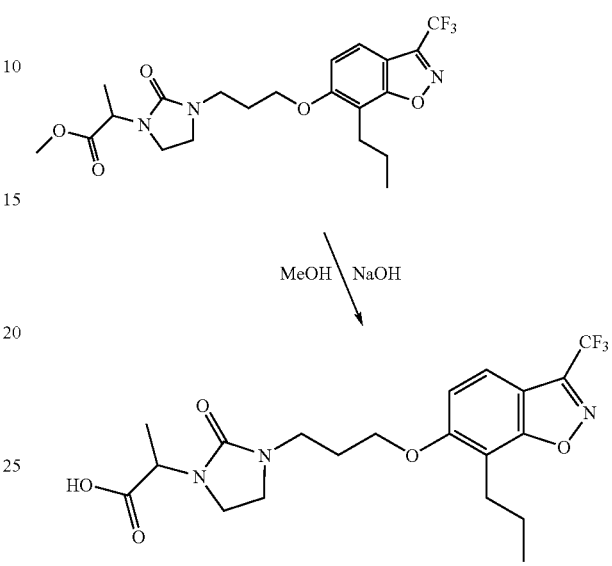

To a MeOH solution (0.6 mL) of methyl 2-[2-oxo-3-(3-{[7-propyl-3-(trifluoromethyl)-1,2-benzisoxazol-6-yl]oxy}propyl)imidazolidin-1-yl]propanoate as prepared in Example 40 (17.6 mg, 0.039 mmol), was added NaOH (0.6 mL, 0.154 mmol) and the mixture stirred at room temperature overnight. The reaction mixture was neutralized with 1N HCl and purified by preparative HPLC and the title compound was obtained.

Selected Signals: ¹H NMR (CDCl₃) δ 7.57 (d, 1H, J=9 Hz), 7.09 (d, 1H, J=9 Hz), 4.67 (q, 1H, J=7.5 & 14.5 Hz), 4.17 (t, 2H, J=7.5 Hz), 3.39–3.51 (m, 6H), 2.94 (t, 2H, J=7.5 Hz), 2.10 (m, 2H), 1.75 (m, 2H), 1.43(d, 3H, J=7.5 Hz), 0.98 (t, 3H, J=7.0 Hz). MS: m/z=444 (M+H)

EXAMPLE 42

Preparation of 1-(3-{[7-propyl-3-(trifluoromethyl)-1,2-benzisoxazol-6-yl]oxy}propyl)imidazolidine-2,4-dione.

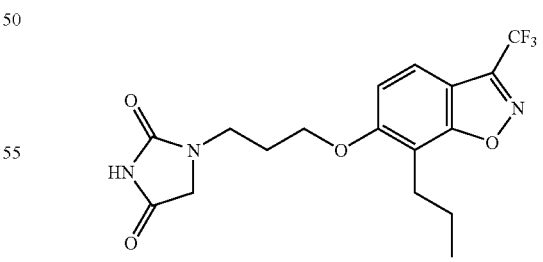

A mixture of imidazolidine-2,4-dione (5.01 g), Cs₂CO₃, and 4-methoxybenzyl chloride (8.0 mL) in DMF (250 mL) was allowed to react overnight. The reaction was added to 400 mL brine then extracted with ether. The desired product precipitated from the ether, and was collected by filtration to yield 1-(4-methoxybenzyl)-imidazolidine-2,4-dione as a white solid.

A mixture of 1-(4-methoxybenzyl)-imidazolidine-2,4-dione (57 mg), 7-propyl-3-trifluoromethyl-6-(3-bromopropyloxy)-1,2-benzisoxazole from Example 7 (86 mg), and Cs$_2$CO$_3$ (146 mg) in DMF (4.0 mL) was allowed to react overnight. Water was added and the mixture separated by HPLC to yield 1-(3-{[7-propyl-3-(trifluoromethyl)-1,2-benzisoxazol-6-yl]oxy}propyl)-3-(4-methoxybenzyl)-imidazolidine-2,4-dione as a clear oil.

To a solution of this compound (39 mg) in a mixture of CH$_3$CN (5.4 mL) and H$_2$O (0.6 mL) was added ceric ammonium nitrate (210 mg) and the resultant solution was allowed to react overnight. The reaction was diluted with H$_2$O (9 mL), then extracted with EtOAc. The combined organic layers were washed sequentially with saturated NaHCO$_3$, NaHSO$_3$, and with brine and dried over Na$_2$SO$_4$. The crude extract was filtered and the solvent removed in vacuo to yield a clear oil/white solid, which was dissolved in 2:1 CH$_3$CN and separated by HPLC to yield the title compound.

Selected Signals: $^1$H NMR (500 MHz; CDCl$_3$) δ 7.73 (s, 1H), 7.60 (d, 1H, J=9.0 Hz), 7.07 (d, 1H, J=8.5 Hz), 4.19 (t, 2H, J=6.0 Hz), 4.00 (s, 2H); 3.66 (t, 2H, J=7.0 Hz), 2.95 (t, 2H, J=7.5 Hz), 2.18 (pent, 2H, J=6.8 Hz), 1.74 (sext, 2H, J=7.5 Hz), 1.00 (t, 3H, J=7.2 Hz). MS: m/z=386 (M+H).

EXAMPLE 43

Preparation of 5,5-dimethyl-1-(3-{[7-propyl-3-(trifluoromethyl)-1,2-benzisoxazol-6-yl]oxy}propyl)imidazolidine-2,4-dione.

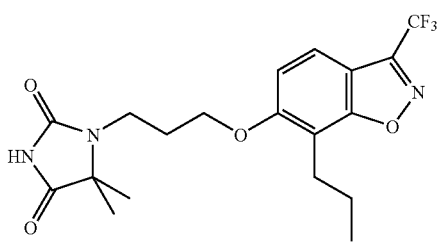

5,5-Dimethyl-1-(3-{[7-propyl-3-(trifluoromethyl)-1,2-benzisoxazol-6-yl]oxy}propyl)imidazolidine-2,4-dione was prepared as for Example 42 starting from 5,5-dimethylimidazolidinedione.

Selected Signals: $^1$H NMR (500 MHz; CDCl$_3$) δ 8.54 (s, 1H), 7.60 (d, 1H, J=9.0 Hz), 7.08 (d, 1H, J=8.5 Hz), 4.19 (t, 2H, J=6.0 Hz), 3.52 (t, 2H, J=7.5 Hz), 2.96 (t, 2H, J=7.8 Hz), 2.27 (pent, 2H, J=7.2 Hz), 1.75 (sext, 2H, J=7.5 Hz), 1.47 (s, 6H), 1.02 (t, 3H, J=7.5 Hz). MS: m/z=414 (M+H).

EXAMPLE 44

Step 1: Preparation of cis 2-({tert-butyl(dimethyl)silyloxy}methyl)cyclohexanol.

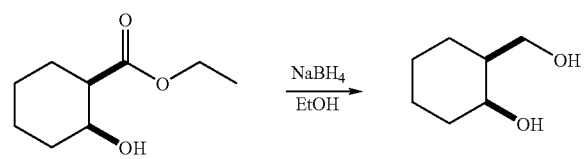

To a solution of ethyl cis-2-hydroxy-1-cyclohexanecarboxylate (2 g, 11.62 mmol) in EtOH (70 mL) was added NaBH$_4$ (2.2 g, 11.62 mmol) in portions at 0° C. The mixture was stirred at room temperature overnight. The reaction mixture was partitioned between ethyl acetate and water. The combined organic layers were washed with brine, dried over Na$_2$SO$_4$ and filtered. The solvent was evaporated in vacuo to give the diol.

tert-Butyldimethylsilyl chloride (1.7 g, 11.07 mmol) in dry THF (11 mL) was added dropwise to a mixture of the diol (1.2 g, 9.23 mmol) and imidazole (1.56 g, 22.15 mmol) in dry THF (14 mL) at 0° C. The reaction mixture was stirred at room temperature 72 hrs. Solvent was evaporated and the residue dissolved in ethyl ether, washed with water three times, dried over Na$_2$SO$_4$ and filtered. The solvent was evaporated in vacuo. The residue was purified by chromatography on silica gel using acetone and hexane (1:99) to give the title compound.

Selected Signals: $^1$H NMR (CDCl$_3$) δ 4.056 (m, 1H), 3.735 (dd, 1H), 3.671 (dd, 1H), 1.773–1.183 (m, 9H), 0.855 (s, 9H), 0.023 (s, 6H).

Step 2: Preparation of 6-{[cis-2-({[tert-butyl(dimethyl)silyl]oxy}methyl)-cyclohexyl]oxy}-7-propyl-3-(trifluoromethyl)-1,2-benzisoxazole.

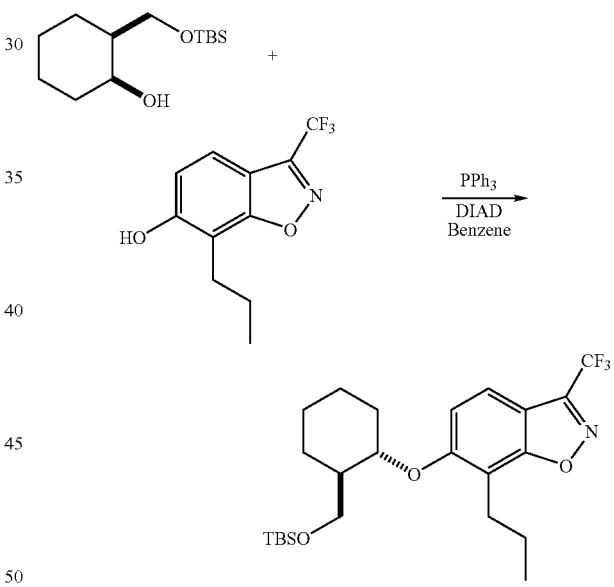

A mixture of 6-hydroxy-7-propyl-3-(trifluoromethyl)-1,2-benzisoxazole (730 mg, 2.98 mmol), 2-({tert-butyl(dimethyl)silyloxy}methyl)-cyclohexanol (800 mg, 3.28 mmol) from this Example step 1, and triphenylphosphine (1.02 g, 3.874 mmol) was dissolved in dry benzenes (16 mL). Diisopropylazodicarboxylate (0.78 mL, 3.874 mmol) was added dropwise. The reaction mixture was stirred at room temperature overnight. The solvent was evaporated in vacuo and the residue purified by chromatography on silica gel using acetone and hexane (1:99) to give the title compound.

Selected Signals: $^1$H NMR (CDCl$_3$) δ 7.53 (d, 1H, J=9 Hz), 7.182 (d, 1H, J=8.9 Hz), 4.374 (m, 4H), 3.825 (m, 1H), 3.684 (m, 1H), 2.930 (t, 2H, J=7.5 Hz, 7.6 Hz), 2.146–1.327 (m, 11H), 1.004 (t, 3H, J=7.3 Hz, 7.4 Hz), 0.898 (d, 9H, J=21.3 Hz), 0.037 (t, 6H, J=29.5 Hz, 37.8 Hz).

Step 3: Preparation of 6-{[cis-2-(hydroxymethyl)cyclohexyl]oxy}-7-propyl-3-(trifluoromethyl)-1,2-benzisoxazole.

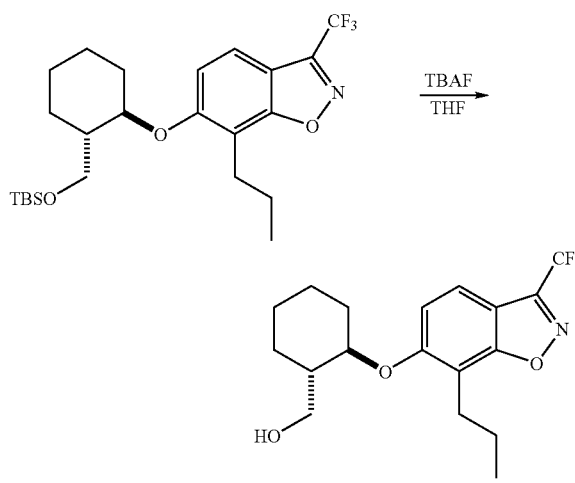

To a solution of 6-{[(1S,2S)-2-({[tert-butyl(dimethyl)silyl]oxy}-methyl)cyclohexyl]oxy}-7-propyl-3-(trifluoromethyl)-1,2-benzisoxazole (550 mg, 1.17 mmol), from this Example step 2, in dry THF (17 ml) was added tetrabutylammonium fluoride (1M THF, 1.75 mL, 1.75 mmol) at 0° C. The reaction mixture was stirred at room temperature for two hours. Saturated NaHCO$_3$ was added. The mixture was extracted with ethyl acetate three times and the combined organic layers washed with brine, dried over Na$_2$CO$_3$ and filtered. The solvent was evaporated in vacuo. The residue was purified by chromatography on silica gel using ethyl acetate and hexane (20:80) to give the title compound.

Selected Signals: $^1$H NMR (CDCl$_3$) δ 7.551 (d, 1H, J=9 Hz), 7.167 (d, 1H, J=8.9 Hz), 4.351 (m, 4H), 3.792 (m, 2H), 2.922 (t, 2H, J=7.6 Hz, 7.8 Hz), 2.138–1.590 (m, 8H), 1.438–1.316 (m, 4H), 0.994 (t, 3H, J=7.3 Hz, 7.3 Hz).

Step 4: Preparation of cis(2-{[7-propyl-3-(trifluoromethyl)-1,2-benzisoxazol-6-yl]oxy}cyclohexyl)methyl methanesulfonate.

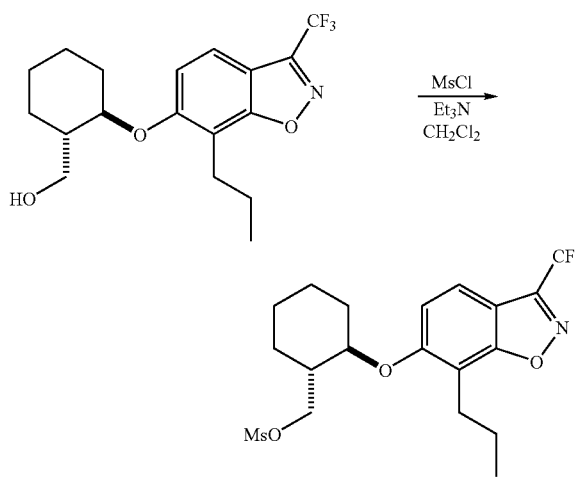

To a solution of 6-{[cis-2-(hydroxymethyl)cyclohexyl]oxy}-7-propyl-3-(trifluoromethyl)-1,2-benzisoxazole (388 mg, 1.09 mmol), from this Example step 3, in CH$_2$Cl$_2$ (11 mL) was added Et$_3$N (0.230 ml, 1.635 mmol) at 0° C., followed by methanesulfonyl chloride (0.093 mL, 1.2 mmol). The reaction mixture was stirred from 0° C. to room temperature for four hours. The mixture was diluted with CH$_2$Cl$_2$, washed with 5% HCl, followed by H$_2$O then NaHCO$_3$. Organic extracts were dried over NaSO$_4$ and filtered. The solvent was evaporated in vacuo to give title compound.

Selected Signals: $^1$H NMR (CDCl$_3$) δ 7.555 (d, 1H, J=8.7 Hz), 7.103 (d, 1H, J=8.9 Hz), 4.447 (m, 1H), 4.33 (m, 2H), 2.934 (s, 3H), 2.913 (t, 2H, J=7.5 Hz, 7.8 Hz), 2.197–1.994 (m, 4H), 1.841–1.335 (m, 7H), 0.985 (t, 3H, J=7.4 Hz, 7.5 Hz). MS: m/z=436.1 (M+1)

Step 5: Preparation of 1-[cis-2-{[7-propyl-3-(trifluoromethyl)-1,2-benzisoxazol-6-yl]oxy}cyclohexyl)methyl]dihydropyrimidine-2,4(1H,3H)-dione.

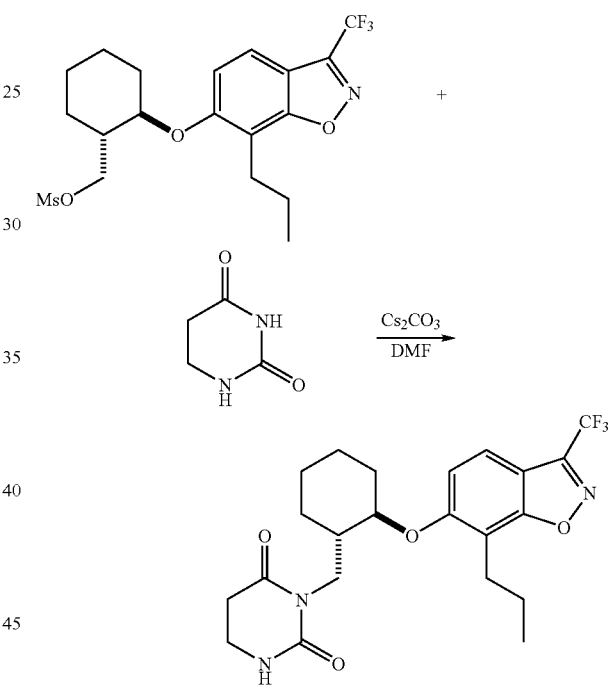

cis-(2-{[7-Propyl-3-(trifluoromethyl)-1,2-benzisoxazol-6-yl]oxy}cyclohexyl)methyl methanesulfonate (50 mg, 0.115 mmol from this Example step 4), 5,6-dihydrouracil (39.4 mg, 0.345 mmol) and Cs$_2$CO$_3$ (150 mg, 0.46 mmol) were dissolved in dry DMF (1 mL) and stirred at room temperature 72 hrs. The reaction mixture was diluted with water and partitioned between ethyl acetate and water. The combined organic extracts were washed with water and brine, dried over Na$_2$SO$_4$ and filtered. The solvent was evaporated in vacuo. The residue was purified by preparative TLC using ethyl acetate and hexane (20:80) to give the title compound.

Selected Signals: $^1$H NMR (CDCl$_3$) δ 7.536 (d, 1H, J=8.9 Hz), 7.12 (d, 1H, J=9 Hz), 4.298 (m, 1H), 4.117 (m, 1H), 3.798 (m, 1H), 3.329 (m, 2H), 2.936 (m, 2H), 2.658 (m, 2H), 2.280(m, 1H), 2.051–1.622 (m, 5H), 1.369–1.206 (m, 4H), 0.990 (t, 3H, J=7.3 Hz, 7.4 Hz). MS: m/z=454.2 (M+1)

EXAMPLE 45

Step 1: Preparation of (trans-2-{[7-propyl-3-(trifluoromethyl)-1,2-benzisoxazol-6-yl]oxy}cyclopentyl)methyl methanesulfonate.

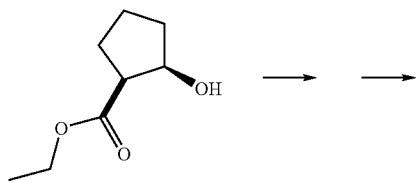

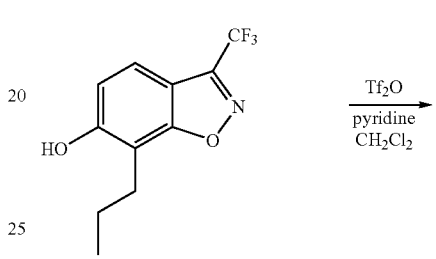

(trans-2-{[7-Propyl-3-(trifluoromethyl)-1,2-benzisoxazol-6-yl]oxy}cyclopentyl) methyl methanesulfonate was prepared as for Example 44 Steps 1 through 4 starting from ethyl cis-2-hydroxycyclopentanecarboxylate.

Selected Signals: $^1$H NMR (CDCl$_3$) δ 7.57 (d, 1H, J=8.7 Hz), 7.12 (d, 1H, J=8.7 Hz), 4.8 (m, 1H), 4.27 (m, 2H), 30336 (s, 3H), 2.896 (t, 2H, J=7.3 Hz, 7.6 Hz), 2.197–1.994 (m, 4H), 1.841–1.335 (m, 7H), 0.985 (t, 3H, J=7.3 Hz, 7.4 Hz). MS: m/z=422.2 (m+1)

Step 2: Preparation of 1-[trans-2-{[7-propyl-3-(trifluoromethyl)-1,2-benzisoxazol-6-yl]oxy}cyclopentyl)methyl]dihydropyrimidine-2,4(1H,3H)-dione.

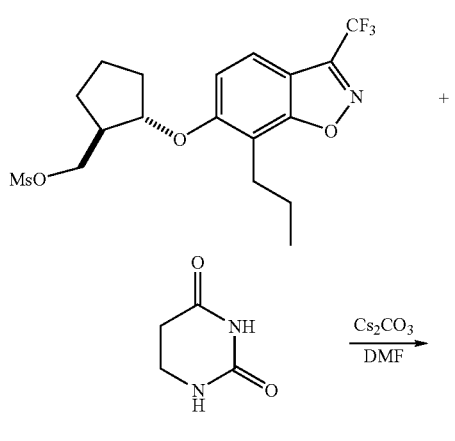

1-[((1R,2S)-2-{[7-Propyl-3-(trifluoromethyl)-1,2-benzisoxazol-6-yl]oxy}cyclopentyl)methyl]dihydropyrimidine-2,4(1H,3H)-dione was prepared from the mesylate of this Example step 1 as for Example 44 Step 5. The product was purified by preparative TLC using ethyl acetate and hexane (50:50) to give title compound.

Selected Signals: $^1$H NMR (CDCl$_3$) δ 7.537 (d, 1H, J=8.9 Hz), 7.056 (d, 1H, J=8.9 Hz), 4.764 (m, 1H), 3.685 (m, 1H), 3.826 (m, 1H), 3.288 (m, 2H), 2.873 (t, 2H, J=7.3 Hz, 7.3 Hz). MS: m/z=440.2 (M+1)

EXAMPLE 46

Step 1: Preparation of 7-propyl-3-(trifluoromethyl)-1,2-benzisoxazol-6-yl trifluoromethanesulfonate.

To a solution of 6-hydroxy-7-propyl-3-(trifluoromethyl)-1,2-benzisoxazole (500 mg, 2.04 mmol) in dry CH$_2$Cl$_2$ was added pyridine (0.82 mL, 10.2 mmol) at 0° C. under N$_2$. Tf$_2$O was then added dropwise to the reaction mixture and the resulting mixture stirred for 30 min. 1N NaOH was added and the mixture extracted with CH$_2$Cl$_2$. Combined organic extracts were washed with brine, dried over Na$_2$SO$_4$ and the solvent evaporated in vacuo. The residue was purified by chromatography on silica gel using ethyl acetate and hexane (10:90) to give the title compound.

Selected Signals: $^1$H NMR (CDCl$_3$) δ 7.75 (d, 1H, J=8.9 Hz), 7.43 (d, 1H, J=8.7 Hz), 3.07 (t, 2H), 1.85 (m, 2H), 1.06 (t, 3H, J=7.3 Hz, 7.3 Hz).

Step 2: Preparation of (but-3-enyloxy)(tert-butyl)dimethylsilane.

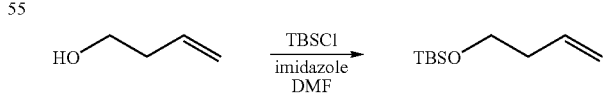

To a solution of but-3-en-1-ol (2.39 mL, 27.73 mmol) in DMF was added imidazole (3.78 g, 55.46 mmol), and tert-butyldimethylsilyl chloride (6.3 g, 41.59 mmol). The mixture was stirred at room temperature overnight. Saturated NH$_4$Cl was added and the mixture was extracted with ethyl acetate three times. Combined organic extracts were washed twice with water and brine then dried over Na$_2$SO$_4$.

The solvent was evaporated in vacuo to give title compound.

Selected Signals: $^1$H NMR (CDCl$_3$) δ 5.84 (m, 1H), 5.07 (m, 2H), 3.68 (t, 2H, J=6.7 Hz, 6.8 Hz), 2.31 (m, 2H), 0.92 (t, 9H), 0.08 (t, 6I).

Step 3: Preparation of 6-(4-{[tert-butyl(dimethyl)silyl]oxy}butyl)-7-propyl-3-(trifluoromethyl)-1,2-benzisoxazole.

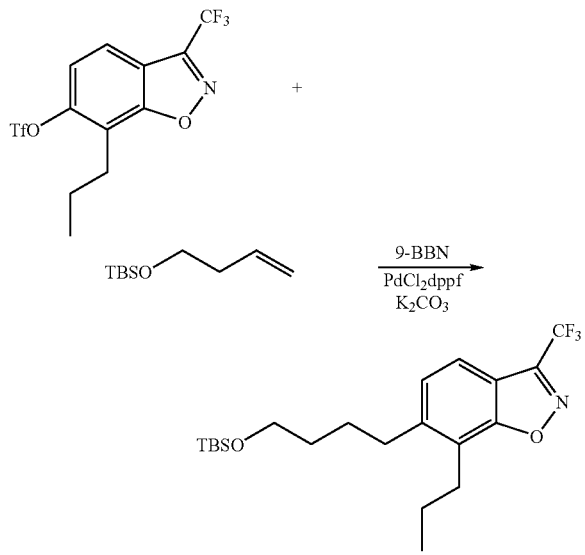

To a solution of (but-3-enyloxy)(tert-butyl)dimethylsilane, from this Example step 2, (148 mg, 0.79 mmol) in dry THF (0.25 mL) was added 9-BBN (0.5M 1.75 mL, 0.88 mmol) at 0° C. under N$_2$. The mixture was stirred for 5 hours, then added to a mixture of 7-propyl-3-(trifluoromethyl)-1,2-benzisoxazol-6-yl trifluoromethanesulfonate, as prepared in this Example step 1, (300 mg, 0.79 mmol), K$_2$CO$_3$ (220 mg, 1.59 mmol), and dichlorobis(triphenylphosphene) palladium (32.5 mg, 0.039 mmol) in DMF (3 mL) under N$_2$ in a sealed tube. The mixture was stirred overnight at 55° C. The reaction mixture was partitioned between ethyl acetate and water. Combined organic extracts were washed with water twice and brine and then dried over Na$_2$SO$_4$. The solvent was evaporated in vacuo. The residue was purified by chromatography on silica gel using ethyl acetate and hexane (1:30) to give the title compound.

Selected Signals: $^1$H NMR (CDCl$_3$) δ 7.56 (d, 1H, J=8.2 Hz), 7.29 (d, 1H, J=8.3 Hz), 3.68 (t, 2H, J=6.2 Hz, 5.9 Hz), 2.98 (t, 2H, J=8 Hz, 7.9 Hz), 2.83 (t, 2H, J=7.5 Hz, 8.1 Hz), 1.72 (m, 6H), 1.06 (t, 3H). 0.916 (s, 9H), 0.072 (s, 6H).

Step 4: Preparation of 4-[7-propyl-3-(trifluoromethyl)-1,2-benzisoxazol-6-yl]butan-1-ol.

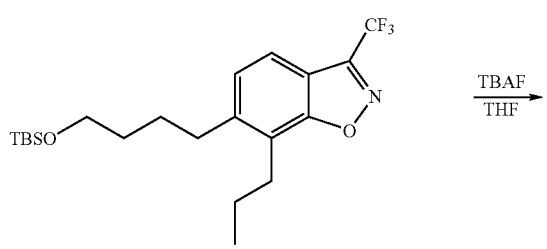

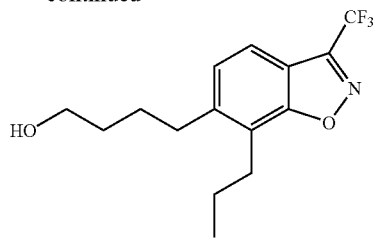

To a solution of 6-(4-{[tert-butyl(dimethyl)silyl]oxy}butyl)-7-propyl-3-(trifluoromethyl)-1,2-benzisoxazole, from this Example step 3, (2.8 g, 6.7 mmol) in dry THF (75 mL) was added tetrabutylammonium fluoride (1.0M 10.1 mL, 10.1 mmol) at 0° C. The mixture was stirred at room temperature for 2 hours. Saturated NaHCO$_3$ was added and the mixture was extracted with ethyl acetate 3 times. Combined organic extracts were washed with brine and dried over Na$_2$SO$_4$. The solvent was evaporated in vacuo. The residue was purified by chromatography on silica gel using ethyl acetate and hexane (20:80) to give the title compound.

Selected Signals: $^1$H NMR (CDCl$_3$) δ 7.56 (d, 1H, J=8.2 Hz), 7.3 (d, 1H, J=8.0 Hz), 3.72 (m, 2H), 2.98 (t, 2H, J=7.8 Hz, 8 Hz), 2.85 (t, 2H, J=7.1 Hz, 8 Hz), 1.73 (m, 6H), 1.05 (t, 3H, J=7.3 Hz, J=Hz).

Step 5: Preparation of 4-[7-propyl-3-(trifluoromethyl)-1,2-benzisoxazol-6-yl]butyl methanesulfonate.

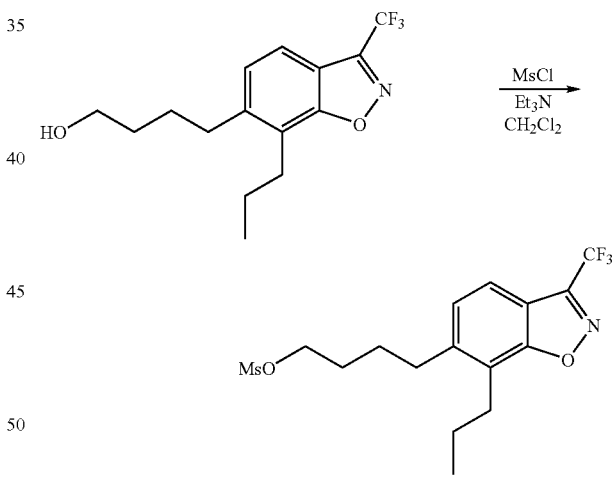

To a solution of 4-[7-propyl-3-(trifluoromethyl)-1,2-benzisoxazol-6-yl]butan-1-ol, from this Example step 4, in CH$_2$Cl$_2$ (25 mL) was added Et$_3$N (0.42 mL, 2.99 mmol) and methanesulfonyl chloride (0.17 mL, 2.2 mmol) at 0° C. The mixture was stirred from 0° C. to room temperature for 2 hours. 0.5N HCl was added and the mixture extracted 3 times with CH$_2$Cl$_2$. Combined organic extracts were washed with water and brine then dried over Na$_2$SO$_4$. The solvent was evaporated in vacuo to give the title compound.

Selected Signals: $^1$H NMR (CDCl$_3$) δ 7.58 (d, 1H J=8.2 Hz), 7.29 (d, 1H J=8.2 Hz), 4.3 (t, 2H, J=6.1 Hz, 6.4 Hz), 3.037 (s, 3H), 2.98 (t, 2H), 2.87(t, 2H, J=8 Hz, 7.5 Hz), 1.88 (m, 2H), 1.78 (m, 4H), 1.06 (t, 2H, J=7.3 Hz, 7.3 Hz).

Step 6: Preparation of 1-{4-[7-propyl-3-(trifluoromethyl)-1,2-benzisoxazol-6-yl]butyl}dihydropyrimidine-2,4(1H,3H)-dione.

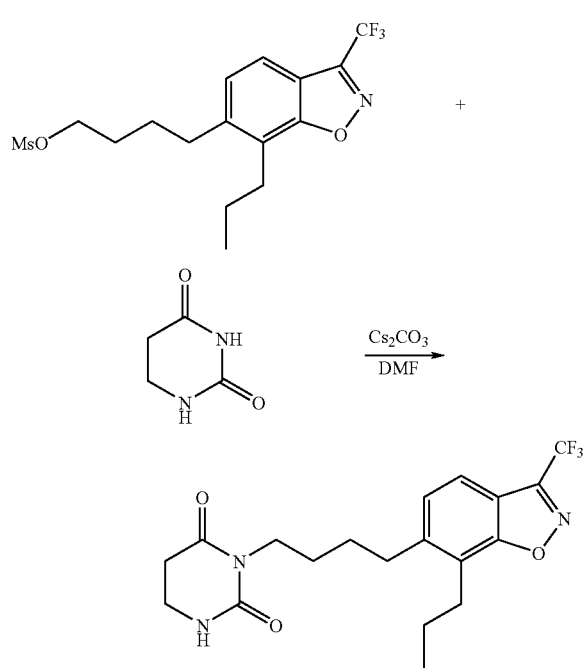

A mixture of 4-[7-propyl-3-(trifluoromethyl)-1,2-benzisoxazol-6-yl]butyl methanesulfonate (60 mg, 0.16 mmol), from this Example step 5, $Cs_2CO_3$ (206 mg, 0.63 mmol) and 5,6-dihydrouracil (54.2 mg, 0.48 mmol) in dry DMF (1.5 mL) was stirred at room temperature overnight. The reaction mixture was partitioned between ethyl acetate and water. Combined organic extracts were washed with water and brine, dried over $Na_2SO_4$ and the solvent evaporated in vacuo. The residue was purified by preparative TLC using ethyl acetate to give the title compound.

Selected Signals: $^1$H NMR (CDCl$_3$) δ 7.55 (d, 1H J=8.2 Hz), 7.28 (d, 1H J=8.2 Hz), 5.704 (s, 1H), 3.8 (t, 2H, J=6.9 Hz, 6.3 Hz), 3.42 (m, 2H,) 2.96 (t, 2H), 2.832 (t, 2H, J=8.0 Hz, 7.1 Hz), 2.741 (t, 2H, J=6.7 Hz, 6.8 Hz), 1.68 (m, 6H), 1.044 (t, 2H, J=7.3, 7.3 Hz). MS: m/z=398.2 (M+1)

EXAMPLE 47

Step 1: Preparation of 5-phenyldihydropyrimidine-2,4(1H,3H)-dione.

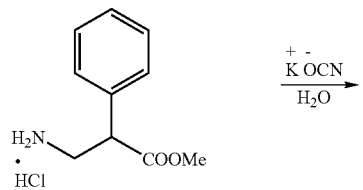

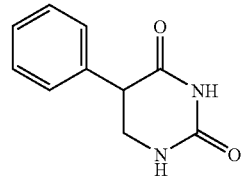

A mixture of D-(−)-alpha-phenylglycine ethyl ester HCl (200 mg, 0.93 mmol) and potassium cyanate (92.7 mg, 1.14 mmol) in water (15 mL) was heated at reflux overnight. Upon cooling to room temperature, the product precipitated from the reaction mixture. The product was collected by filtration and dried for use without purification.

Selected Signals: $^1$H NMR (CD$_3$OD) δ 7.3 (m, 5H), 3.9 (m, 1H), 3.61 (m, 1H), 3.53 (m, 1H).

Step 2: Preparation of 5-phenyl-3-(3-{[7-propyl-3-(trifluoromethyl)-1,2-benzisoxazol-6-yl]oxy}propyl)dihydropyrimidine-2,4(1H,3H)-dione.

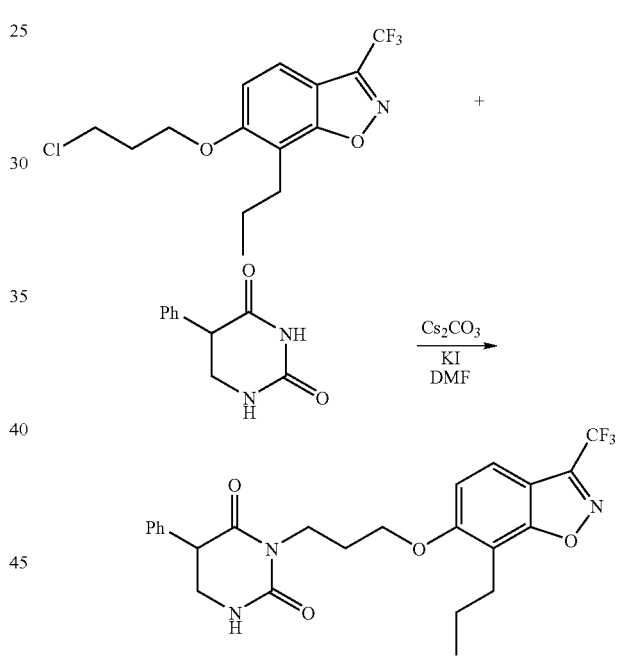

A mixture of 6-(3-chloropropoxy)-7-propyl-3-(trifluoromethyl)-1,2-benzisoxazole, prepared as for Example 7 from bromochloropropane, (36 mg, 0.12 mmol), 5-phenyldihydropyrimidine-2,4(1H,3H)-dione, from this Example step 1, (42.5 mg, 0.22 mmol), Cs$_2$CO$_3$ (145.7 mg, 0.45 mmol) and KI (9.3 mg, 0.056 mmol) in dry DMF was stirred at room temperature overnight. The reaction mixture was diluted with water and partitioned between ethyl acetate and water. Combined organic extracts were washed with water and brine, dried over Na$_2$SO$_4$ and the solvent evaporated in vacuo. The product was purified by HPLC using 30% to 70% gradient CH$_3$CN:H$_2$O).

Selected Signals: $^1$H NMR (CDCl$_3$) δ 7.55 (d, 1H, J=8.7 Hz), 7.36 (m, 5H) 7.04 (d, 1H, J=8.7 Hz), 5.722 (s, 1H), 4.13 (m, 4H), 3.93 (m, 1H), 3.66 (m, 2H), 2.93 (t, 2H, J=7.5 Hz, 7.6 Hz), 2.21 (m, 2H), 1.74 (m, 2H), 0.992 (t, 3H, J=7.1 Hz, 7.3 Hz). MS: m/z=476.2 (M+1)

EXAMPLE 48

Step 1: Preparation of 6-phenyldihydropyrimidine-2,4(1H,3H)-dione.

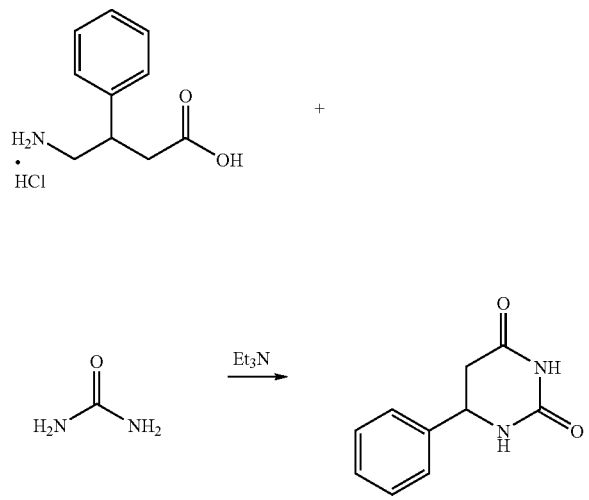

A neat mixture of (R)-(−)-2-phenylglycine (500 mg, 2.4795 mmol) and carbamide (2 g, 33.3 mmol) was heated to 150° C. $Et_3N$ (0.6913 mL, 4.959 mmol) was added after the mixture melted. Stirring was continued at 150° C. for 4 hours followed by cooling to room temperature. The product was dissolve in water at 100° C., then cool to room temperature. Product precipitated out of the solution. The product was collected by filtration and dried for use without purification.

Selected Signals: $^1$H NMR ($CD_3OH$) δ 7.37 (m, 5H), 4.76 (m, 1H), 2.9 (m, 1H), 2.75 (m, 1H).

Step 2: Preparation of 6-phenyl-3-(3-{[7-propyl-3-(trifluoromethyl)-1,2-benzisoxazol-6-yl]oxy}propyl)dihydropyrimidine-2,4(1H,3H)-dione.

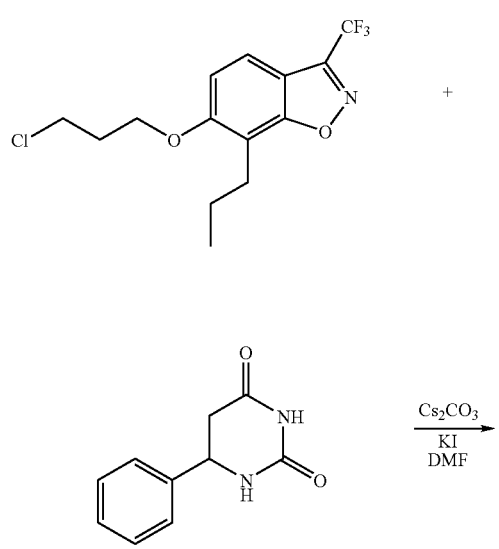

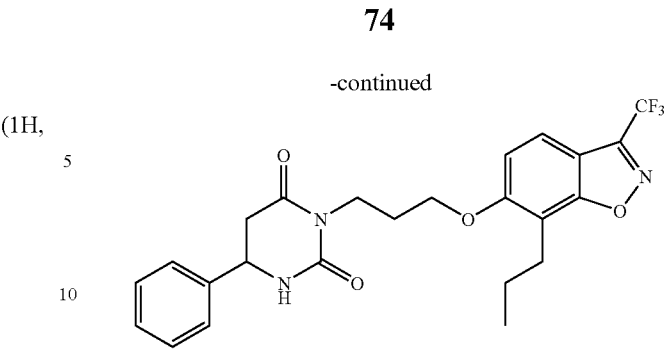

6-Phenyl-3-(3-{[7-propyl-3-(trifluoromethyl)-1,2-benzisoxazol-6-yl]oxy}propyl)dihydropyrimidine-2,4(1H,3H)-dione was prepared as in step 2 Example 47 above. The product was purified by preparative TLC using ethyl acetate and hexane (70:30) to give the title compound.

Selected Signals: $^1$H NMR ($CDCl_3$) δ 7.57 (d, 1H J=8.7 Hz), 7.40 (m, 5H), 7.05 (d, 1H, J=8.7 Hz), 5.65 (s, 1H)4.71 (m, 4H), 4.09(m, 4H), 3.0 (m, 3H), 2.87 (m, 1H), 2.2 (m, 2H), 1.76 (m, 2H), 1.01 (t, 3H, J=7.6 Hz, 7.3 Hz). MS: m/z=476.2 (M+1)

EXAMPLE 49

Preparation of 5-Methyl-3-(3-{[7-propyl-3-(trifluoromethyl)-1,2-benzisoxazol-6-yl]oxy}propyl)dihydropyrimidine-2,4(1H,3H)-dione.

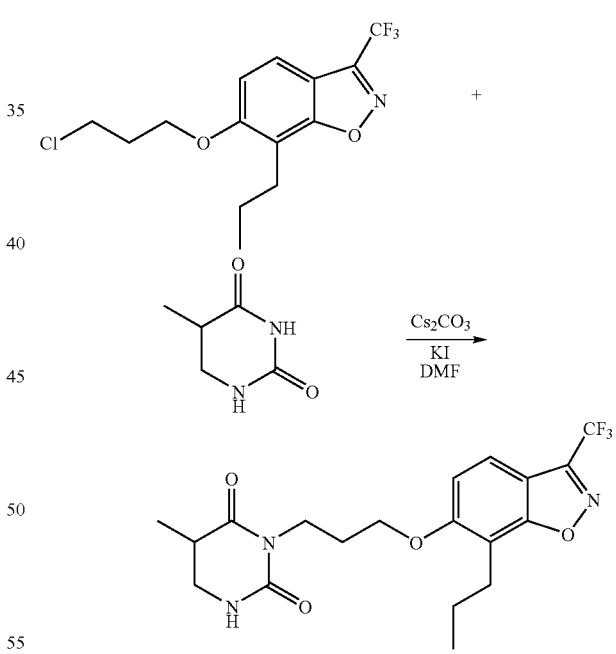

5-Methyl-3-(3-{[7-propyl-3-(trifluoromethyl)-1,2-benzisoxazol-6-yl]oxy}propyl)dihydropyrimidine-2,4(1H,3H)-dione was prepared as in step 2 Example 47 above from the chloride and commercially available 5-methyl-dihydropyrimidine-2,4(1H,3H)-dione.

Selected Signals: $^1$H NMR ($CDCl_3$) δ 7.56 (d, 1H J=8.7 Hz), 7.05 (d, 1H, J=8.9 Hz), 5.3 (s, 1H), 4.14 (t, 4H, J=6.2 Hz, 6.4 Hz), 4.02(m, 2H), 3.72 (m, 1H), 2.96 (t, 2H, J=7.3 Hz, J=7.8 Hz), 2.76 (m, 1H), 2.47 (m, 1H), 2.15 (m, 2H), 1.72 (m, 2H), 1.29 (d, 3H, J=6.2 Hz), 1.0 (t, 3H, J=7.6 Hz, 7.3 Hz).

EXAMPLE 50

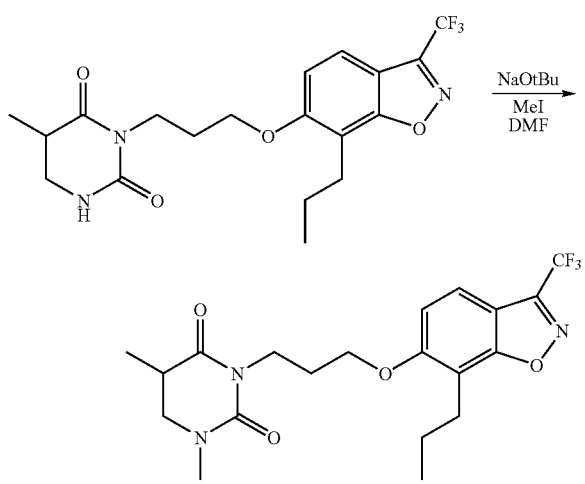

To a mixture of 5-Methyl-3-(3-{[7-propyl-3-(trifluoromethyl)-1,2-benzisoxazol-6-yl]oxy}propyl)dihydropyrimidine-2,4(1H,3H)-dione (30 mg, 0.073 mmol), from Example 49, and NaOtBu (7.3 mg, 0.076 mmol) in dry DMF (1 mL) was added MeI (6.8 μL, 0.109 mmol) at room temperature. Reaction mixture was stirred for 5 days. The reaction mixture was partitioned between ethyl acetate and water. Combined organic extracts were washed with water and brine, dried over $Na_2SO_4$ and the solvent evaporated in vacuo. The product was purified by preparative TLC using ethyl acetate and hexane (70:30) to give the title compound.

Selected Signals: $^1$H NMR (CDCl$_3$) δ 7.57 (d, 1H, J=8.7 Hz), 7.07 (d, 1H, J=8.9 Hz), 4.12 (m, 3H,), 4.0(m, 1H), 3.56 (m, 1H), 3.07 (s, 3H), 2.9 (m, 3H,), 2.56 (m, 2H), 2.17 (m, 2H), 1.74 (m, 2H), 1.25 (d, 3H, J=6.6 Hz), 1.0 (t, 3H, J=7.4 Hz, 7.3 Hz). MS: m/z=428.2 (M+1)

EXAMPLE 51

Step 1: Preparation of 3-(3-{[tert-butyl(dimethyl)silyl]oxy}propyl)-dihydropyrimidine-2,4(1H,3H)-dione.

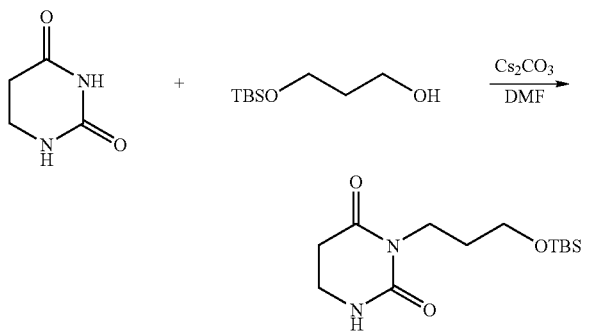

A mixture 5,6-dihydrouracil (4.45 g, 39.028 mmol), 3-{[tert-butyl(dimethyl)silyl]oxy}propan-1-ol (3 mL, 13.01 mmol) and $Cs_2CO_3$ (16.95 g, 52.04 mmol) in dry DMF (120 mL) was stirred at room temperature overnight. The reaction mixture was partitioned between ethyl acetate and water. Combined organic extracts were washed with water and brine, dried over $Na_2SO_4$ and the solvent evaporated in vacuo. Purified by chromatography on silica gel using ethyl acetate and hexane (60:40) to give the title compound.

Selected Signals: $^1$H NMR (CDCl$_3$) δ 5.48 (s, 1H), 3.86 (t, 2H, J=7.5 Hz, 7.45 Hz), 3.68 (t, 2H, J=6.4 Hz, 6.4 Hz), 3.4 (m, 2H), 2.72 (t, 2H, J=6.7 Hz, 6.8 Hz), 1.81 (m, 2H), 0.91 (s, 9H), 0.06 (s, 6H).

Step 2: Preparation of 3-(3-{[tert-butyl(dimethyl)silyl]oxy}propyl)-1-phenyldihydropyrimidine-2,4(1H,3H)-dione.

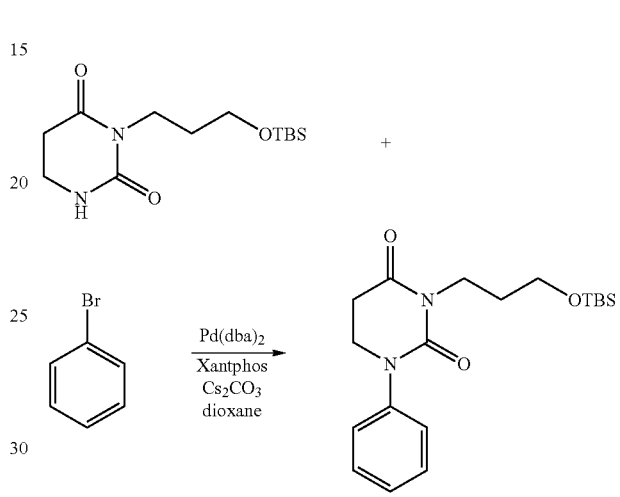

A mixture of 3-(3-{[tert-butyl(dimethyl)silyl]oxy}propyl)-dihydropyrimidine-2,4(1H,3H)-dione (100 mg, 0.35 mmol), from this Example step 1, bromobenzene (0.037 mL, 0.35 mmol), tris(dibenzylideneacetone)dipalladium (6.4 mg, 0.01 mmol), Xantphos (0.0121 g, 0.021 mmol) and $Cs_2CO_3$ (0.171 g, 0.52 mmol) were combined in dry dioxane (1 mL) and stirred at 100° C. overnight in a sealed tube. The reaction mixture was partitioned between ethyl acetate and water. Combined organic extracts were washed with water and brine, dried over $Na_2SO_4$ and the solvent evaporated in vacuo. The product was purified by preparative TLC using ethyl acetate and hexane (30:70) to give the title compound.

Selected Signals: $^1$H NMR (CDCl$_3$) δ 7.43 (t, 2H, J=8.3 Hz, 7.5 Hz), 7.3 (m, 3H), 3.94 (t, 2H), 3.82 (t, 2H, J=6.7 Hz, 6.8 Hz), 3.71 (t, 2H, J=6.4 Hz, 6.4 Hz), 2.88 (t, 2H, J=6.89 Hz, 6.6 Hz), 1.87 (m, 2H), 0.916 (s, 9H), 0.074 (s, 6H).

Step 3: Preparation of 3-(3-hydroxypropyl)-1-phenyldihdropyrimidine-2,4(1H,3H)-dione.

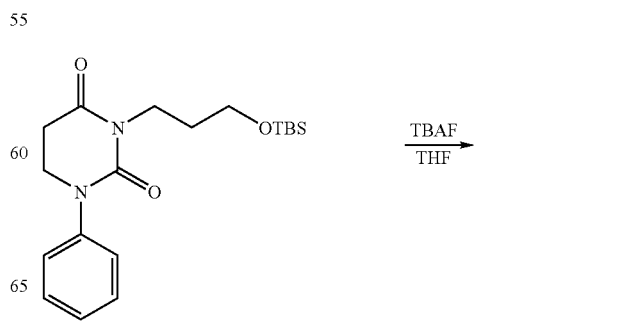

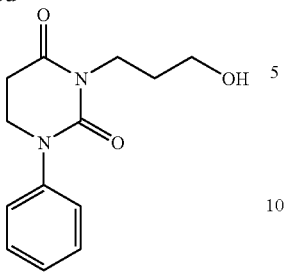

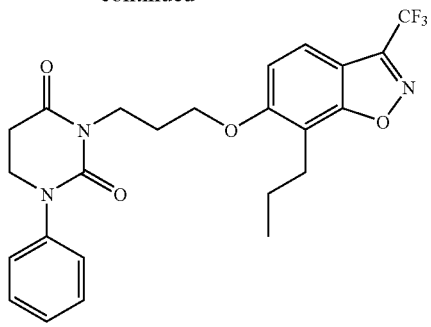

To a solution of 3-(3-{[tert-butyl(dimethyl)silyl]oxy}propyl)-1-phenyldihydropyrimidine-2,4(1H,3H)-dione (115 mg, 0.318 mmol), from this Example step 2, in dry THF (3.5 mL) was added tetra-butylammonium fluoride (1.0 M THF, 0.477 ml, 0.476 mmol) at 0° C. The reaction was stirred from 0° C. to room temperature for 2 hours. Saturated NaHCO$_3$ was added, and the mixture extracted with CH$_2$Cl$_2$ three times. Extracts were dried over Na$_2$SO$_4$ and the solvent evaporated in vacuo. The product was purified by preparative TLC using ethyl acetate and hexane (80:20) to give the title compound.

Selected Signals: $^1$H NMR (CDCl$_3$) δ 7.44 (t, 2H, J=8.5 Hz, 7.4 Hz), 7.3(m, 3H), 4.02 (t, 2H, J=6.2 Hz, 5.9 Hz), 3.85 (t, 2H, J=6.9 Hz, 6.6 Hz), 3.60 (m, 2H), 3.072 (t, 1H, J=6.8 Hz, 6.9 Hz) 2.92 (m, 2H), 1.867 (m, 2H).

Step 4: Preparation of 1-1,2-phenyl-3-(3-{[7-propyl-3-(trifluoromethyl)-1,2-benzisoxazol-6-yl]oxy propyl)dihydropyrimidine-2,4(1H,3H)-dione.

To a mixture of 6-hydroxy-7-propyl-3-(trifluoromethyl)-1,2-benzisoxazole (56.7 mg, 0.23 mmol), 3-(3-hydroxypropyl)-1-phenyldihydropyrimidine-2,4(1H,3,H)-dione (0.0574 g, 0.231 mmol), from this Example step 3, and triphenylphosphine (78.9 mg, 0.30 mmol) in dry benzene (1.3 mL) was added diisopropylazodicarboxylate (0.059 mL, 0.30 mmol). The reaction mixture was stirred at room temperature overnight. The solvent was evaporated in vacuo and the product purified by preparative TLC using 40% diethyl ether/hexane then 70% diethyl ether/hexane to give the title compound.

Selected Signals: $^1$H NMR (CDCl$_3$) δ 7.56 (d, 1H, J=8.9 Hz), 7.31 (m, 5H), 7.08 (d, 1H, J=9 Hz), 4.19 (t, 2H, J=6.4 Hz, 6.4 Hz), 4.103 (t, 2H, J=7.2 Hz, 7.3 Hz), 3.85 (t, 2H, J=6.7 Hz, 6.8 Hz), 2.96 (t, 2H, J=7.4 Hz, 7.7 Hz), 2.92 (t, 2H, 6.6 Hz, 6.6 Hz), 2.25 (m, 2H), 1.74 (m, 2H), 0.993 (t, 3H, J=7.3 Hz, 7.4 Hz). MS: m/z=476.0 (M+1)

EXAMPLE 52

Step 1: Preparation of 3-(3-hydroxypropyl)-1-pyridin-2-yldihydroprimidine-2,4(1H,3H)-dione.

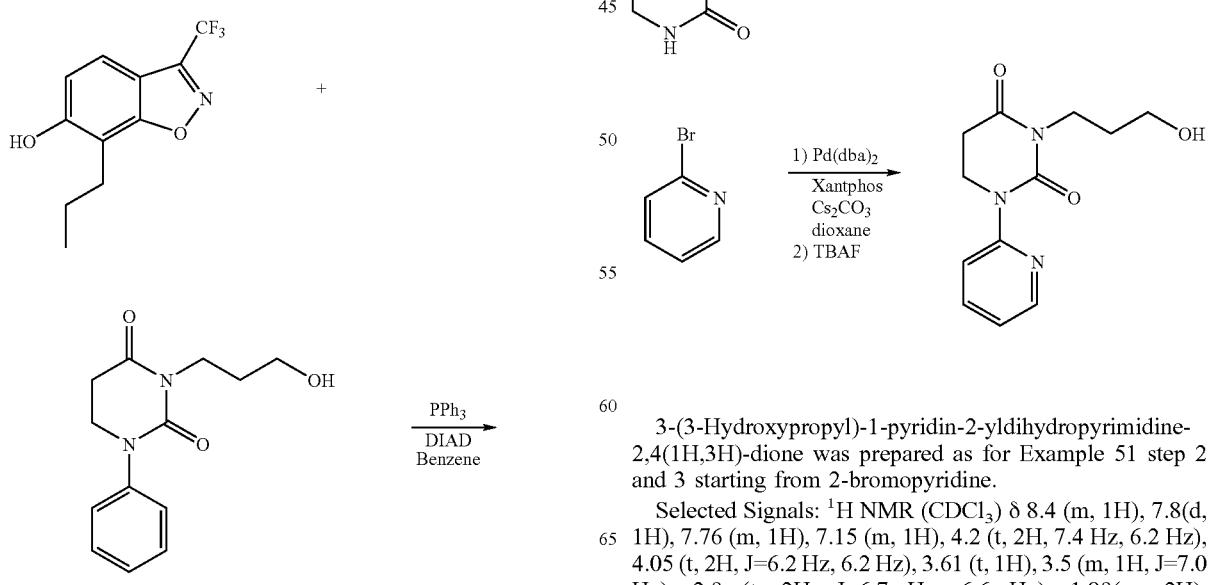

3-(3-Hydroxypropyl)-1-pyridin-2-yldihydropyrimidine-2,4(1H,3H)-dione was prepared as for Example 51 step 2 and 3 starting from 2-bromopyridine.

Selected Signals: $^1$H NMR (CDCl$_3$) δ 8.4 (m, 1H), 7.8(d, 1H), 7.76 (m, 1H), 7.15 (m, 1H), 4.2 (t, 2H, 7.4 Hz, 6.2 Hz), 4.05 (t, 2H, J=6.2 Hz, 6.2 Hz), 3.61 (t, 1H), 3.5 (m, 1H, J=7.0 Hz), 2.9 (t, 2H, J=6.7 Hz, 6.6 Hz), 1.89(m, 2H).

Step 2: Preparation of 3-(3-{[7-propyl-3-(trifluoromethyl)-1,2-benzisoxazol-6-yl]oxy}propyl)-1-pyridin-2-yldihydropyrimidine-2,4(1H,3H)-dione.

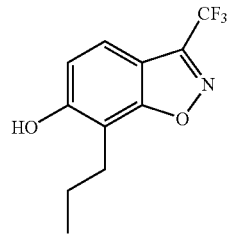

+

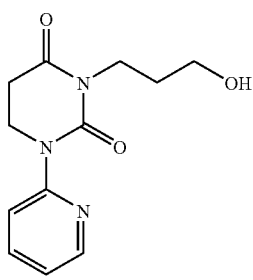

PPh₃
DIAD
Benzene
→

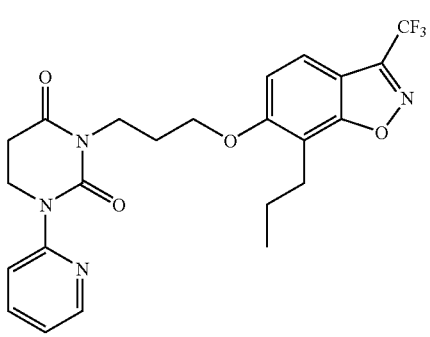

3-(3-{[7-Propyl-3-(trifluoromethyl)-1,2-benzisoxazol-6-yl]oxy}propyl)-1-pyridin-2-yldihydropyrimidine-2,4(1H,3H)-dione was prepared as for Example 51 step 4. The product was purified by preparative TLC using ethyl acetate and hexane (50:50) to give the title compound.

Selected Signals: ¹H NMR (CDCl₃) δ 8.4 (m, 1H), 7.81 (d, 1H, J=8.5 Hz), 7.4 (m, 1H), 7.57 (d, 1H, J=8.7 Hz), 7.13 (m, 1H) 7.07 (d, 1H J=8.7), 4.16 (m, 6H), 2.96 (t, 2H, J=7.4 Hz, 7.5 Hz), 2.88 (t, 2H, J=6.6 Hz, 6.7 Hz), 2.23 (m, 2H,), 0.995 (t, 3H, J=7.6 Hz, 7.2 Hz). MS: m/z=477.2 (M+1)

EXAMPLE 53

Step 1. Preparation of 3-(3-hydroxypropyl)-5,6-dihydro-2H-1,2'-bipyrimidine-2,4(3H)-dione.

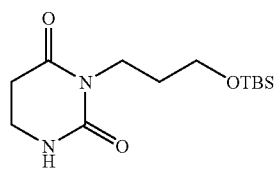

+

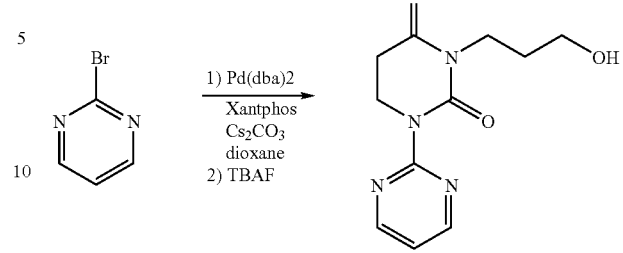

3-(3-Hydroxypropyl)-5,6-dihydro-2H-1,2'-bipyrimidine-2,4(3H)-dione was prepared as for Example 51 step 2 and 3 starting from 2-bromopyrimidine. The product was purified by preparative TLC using ethyl acetate and hexane (80:20) to give the title compound.

Selected Signals: ¹H NMR (CDCl₃) δ 8.73 (d, 2H, J=4.8 Hz), 7.14 (t, 1H, J=4.8 Hz), 4.1 (t, 1H, J=6.4 Hz, 6.6 Hz), 3.97 (t, 2H), 3.71 (t, 2H, J=6.4 Hz, 6.2 Hz), 2.87 (t, 2H, J=6.4 Hz, 6.7 Hz), 1.89 (m, 2H), 0.903 (s, 9H), 0.061 (s, 6H).

Step 2: Preparation of 3-(3-{[7-propyl-3-(trifluoromethyl)-1,2-benzisoxazol-6-yl]oxy}propyl)-5,6-dihydro-2H-1,2'-bipyrimidine-2,4(3H)-dione.

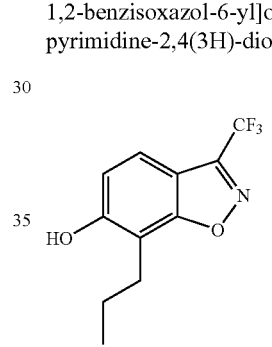

+

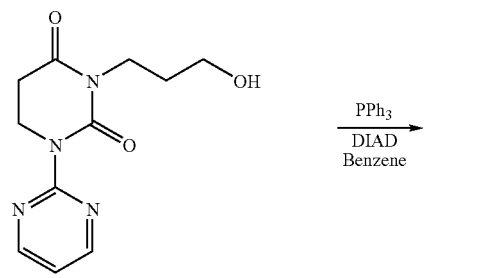

3-(3-{[7-Propyl-3-(trifluoromethyl)-1,2-benzisoxazol-6-yl]oxy}propyl)-5,6-dihydro-2H-1,2'-bipyrimidine-2,4(3H)-dione was prepared as for Example 51 step 4. The product was purified by preparative TLC using ethyl acetate and hexane (70:30) then 100% ethyl acetate to give the title compound.

Selected Signals: ¹H NMR (CDCl₃) δ 8.75 (d, 1H, J=4.8 Hz), 7.56(d, 1H, J=8.9 Hz), 7.17 (t, 1H, J=4.8 Hz, 4.8 Hz), 7.07 (d, 1H, J=8.9 Hz), 4.15 (m, 6H), 2.93 (m, 4H), 2.27 (m, 2H), 1.74 (m, 2H,), 0.988 (t, 3H, J=7.3 Hz, 7.6 Hz). MS: m/z=478.2 (M+1)

EXAMPLE 54

Step 1: Preparation of 3-(3-hydroxypropyl)-5,6-dihydro-2H-1,5'-bipyrimidine-2,4(3H)-dione.

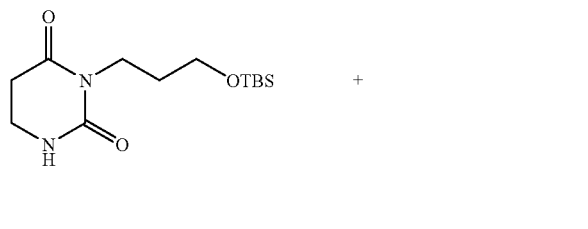

+

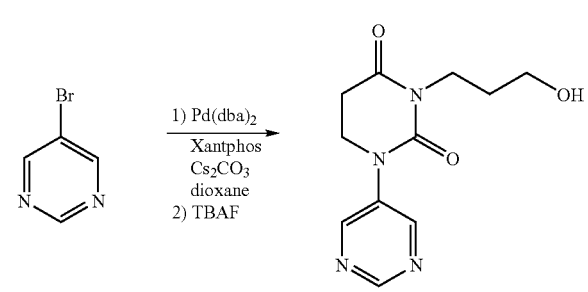

3-(3-Hydroxypropyl)-5,6-dihydro-2H-1,5'-bipyrimidine-2,4(3H)-dione was prepared as for Example 51 step 2 and 3 starting from 5-bromopyrimidine.

The product was purified by preparative TLC using ethyl acetate and hexane (80:20) to give the title compound.

Selected Signals: ¹H NMR (CDCl₃) δ 9.11 (s, 1H), 8.797(s, 2H), 4.04 (t, 2H, J=6.1 Hz, 6.4 Hz), 3.93 (t, 2H, J=6.6 Hz, 6.9 Hz), 3.63 (t, 2H, J=5.7 Hz, 5.5 Hz), 3.0 (t, 2H, J=6.6 Hz, 6.7 Hz), 1.88 (m, 2H).

Step 2: Preparation of 3-(3-{[7-propyl-3-(trifluoromethyl)-1,2-benzisoxazol-6-yl]oxy}propyl)-5,6-dihydro-2H-1,5'-bipyrimidine-2,4(3H)-dione.

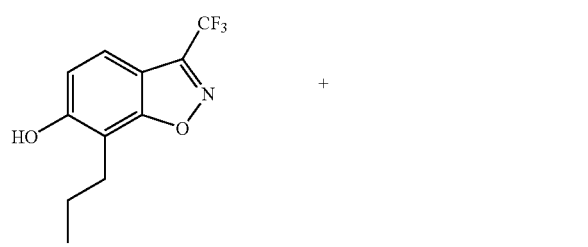

+

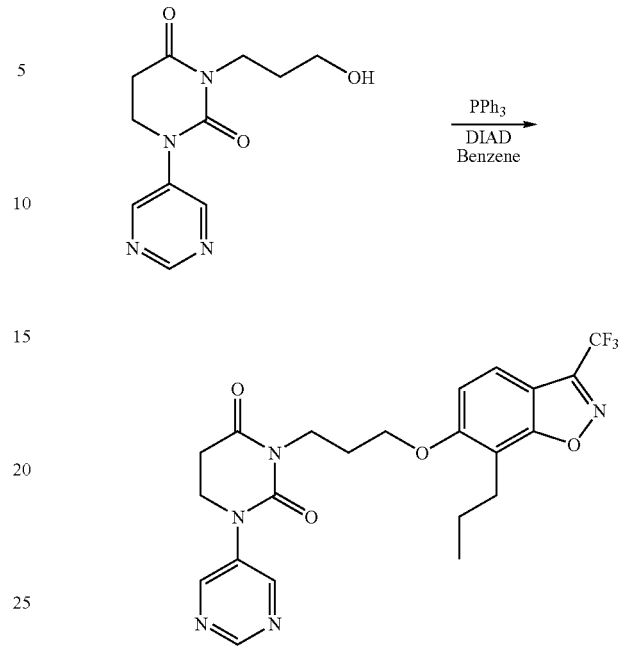

3-(3-{[7-propyl-3-(trifluoromethyl)-1,2-benzisoxazol-6-yl]oxy}propyl)-5,6-dihydro-2H-1,5'-bipyrimidine-2,4(3H)-dione was prepared as for Example 51 step 4. The product was purified by preparative TLC using ethyl acetate and hexane (70:30) then 100% ethyl acetate to give the title compound.

Selected Signals: ¹H NMR (CDCl₃) δ 9.11 (s, 1H), 8.799(s, 2H), 7.57 (d, 1H, J=8.7 Hz), 7.07 (d, 1H, J=8.7 Hz), 4.19 (t, 2H, J=6.2 Hz, 6.2 Hz), 4.13 (t, 2H, J=7.1 Hz, 7.3 Hz), 3.93 (t, 2H, J=6.8 Hz, 6.7 Hz), 2.98 (m, 4H), 2.1 (m, 2H), 1.74 (m, 2H), 0.995 (t, 3H, J=7.3 Hz, 7.5 Hz). MS: m/z=478.2 (M+1)

EXAMPLE 55

Preparation of 1-(3-{[7-propyl-3-(neopentyl)-1,2-benzisoxazol-6-yl]oxy}-propyl)piperidin-2-one.

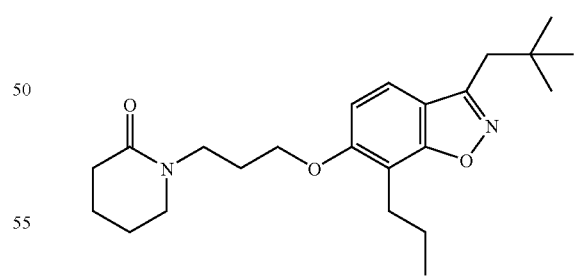

1-(3-{[7-propyl-3-(neopentyl)-1,2-benzisoxazol-6-yl]oxy}propyl)piperidin-2-one was prepared as for Example 10 from piperidin-2-one and the bromide from Example 9. After aqueous work-up and silica gel chromatography, the title compound was obtained.

Selected Signals: ¹H NMR (400 MHz; CDCl₃) δ 7.3 (d 2H, J=8.6 Hz), 6.90 (d, 2H, J=8.6 Hz), 3.63 (t, 2H, J=7.2 Hz), 3.29 (m, 2H), 2.82 (s, 2H), 2.14 (m, 2H), 1.85 (m, 4H), 1.71 (sext, 2H, J=7.4 Hz), 0.986 (t, 3H, J=7.3 Hz).

EXAMPLE 56

Preparation of 1-(3-{[7-propyl-3-(trifluoromethyl)-1,2-benzisoxazol-6-yl]oxy}propyl)piperidin-2-one.

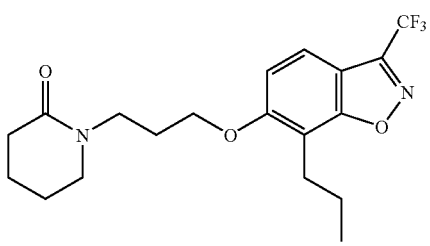

1-(3-{[7-Propyl-3-(trifluoromethyl)-1,2-benzisoxazol-6-yl]oxy}propyl)piperidin-2-one was prepared as for Example 10 from piperidin-2-one and the bromide from Example 7. After aqueous work-up and silica gel chromatography, the title compound was obtained.

Selected Signals: $^1$H NMR (400 MHz; CDCl$_3$) δ 7.57 (d, 1H, J=8.8 Hz); 7.06 (d, 1H, J=8.8 Hz); 4.15 (t, 2H, J=6.2 Hz); 3.63 (t, 2H, J=7.4 Hz); 3.40 (t, 2H, J=5.6 Hz); 2.93 (t, 2H, J=6.2 Hz); 2.51 (t, 2H, J=6.2); 2.16 (pentet, 2H, J=6.7 Hz); 1.90–1.8 (m, 4H); 1.73 (sextet, 2H, J=7.5 Hz); 0.99 (t, 3, J=7.6 Hz).

EXAMPLE 57

Preparation of 1-(3-{[7-propyl-3-(trifluoromethyl)-1,2-benzisoxazol-6-yl]oxy}propyl)piperidin-2,6-dione.

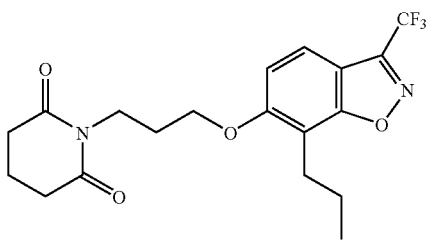

1-(3-{[7-Propyl-3-(trifluoromethyl)-1,2-benzisoxazol-6-yl]oxy}propyl)-piperidin-2,6-dione was prepared as for Example 10 from piperidin-2,6-dione and the bromide from Example 7. After aqueous work-up and silica gel chromatography, the title compound was obtained.

Selected Signals: $^1$H NMR (400 MHz; C$_6$D$_6$) δ 6.43 (d, 1H, J=8.8 Hz); 3.90 (t, 2H, J=7.4 Hz); 3.51 (t, 2H, J=6.4 Hz); 2.93 (t, 2H, J=7.6 Hz); 1.91–1.82 (m, 6H); 1.72 (sextet, 2H, J=7.5 Hz); 0.95 (t, 3H, J=7.4 Hz); 0.83 (pentet, 2H, J=6.6 Hz).

EXAMPLE 58

Preparation of 1-(3-{[7-propyl-3-(phenyl)-1,2-benzisoxazol-6-yl]oxy}propyl)piperidin-2,5-dione.

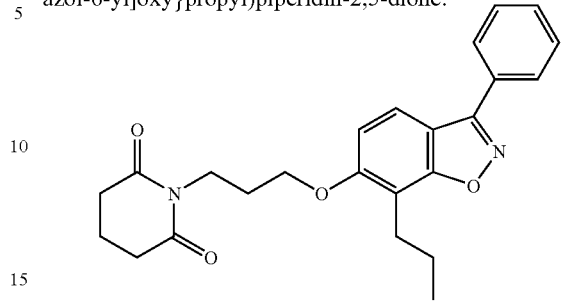

1-(3-{[7-Propyl-3-(phenyl)-1,2-benzisoxazol-6-yl]oxy}propyl)piperidin-2,5-dione was prepared as for Example 10 from piperidin-2,5-dione and the bromide from Example 27. After aqueous work-up and silica gel chromatography, the title compound was obtained.

Selected Signals: $^1$H NMR (400 MHz; CDCl$_3$) δ 7.96–7.93 (m, 2H); 7.66 (d, 1H, J=8.8 Hz); 7.58–7.53 (m, 3); 6.98 (d, 1H, J=8.4 Hz); 4.12 (t, 2H, J=6.2 Hz); 4.04 (t, 2H, J=7.2 Hz); 2.97 (t, 2H, J=7.6 Hz); 2.69 (t, 4H, J=6.4 Hz); 2.10 (pentet, 2H, J=6.7 Hz); 1.96 (pentet, 2H, J=6.6 Hz); 1.77 (sextet, 2H, J=7.6 Hz); 1.02 (t, 3H, J=7.4 Hz).

EXAMPLE 59

Preparation of 4-(3-{[7-propyl-3-(trifluoromethyl)-1,2-benzisoxazol-6-yl]oxy}propyl)morpholine-3,5-dione.

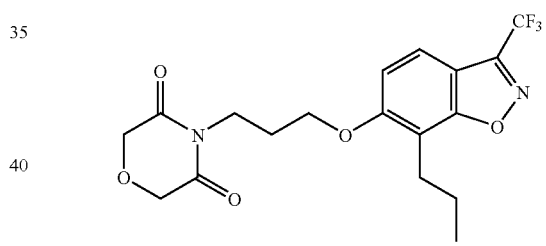

4-(3-{[7-Propyl-3-(trifluoromethyl)-1,2-benzisoxazol-6-yl]oxy}propyl)morpholine-3,5-dione was prepared as for Example 10 from morpholine-3,5-dione and the bromide from Example 7. After aqueous work-up and silica gel chromatography, the title compound was obtained.

Selected Signals: $^1$H NMR (400 MHz; CDCl$_3$) δ 7.57 (d, 1H, J=8.8 Hz); 7.04 (d, 1H, J=8.8 Hz); 4.38 (s, 4H); 4.14 (t, 2H, J=6.0 Hz); 4.07 (t, 2H, J=7.2 Hz); 2.96 (t, 2H, J=7.4 Hz); 2.16 (pentet, 2H, J=6.6 Hz); 1.74 (sextet, 2H, J=7.5 Hz); 1.00 (t, 3H, J=7.2 Hz).

EXAMPLE 60

Preparation of 1-(3-}[7-propyl-3-(trifluoromethyl)-1,2-benzisoxazol-6-yl]oxy}propyl)piperazine-2,5-dione.

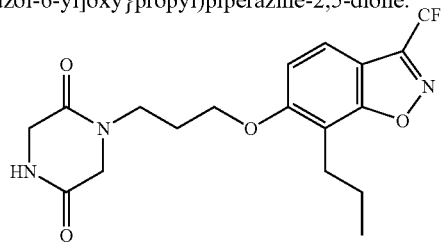

1-(3-{[7-Propyl-3-(trifluoromethyl)-1,2-benzisoxazol-6-yl]oxy}propyl)piperazine-2,5-dione was prepared as for Example 10 from piperazine-2,5-dione and the bromide from Example 7. After aqueous work-up and silica gel chromatography, the title compound was obtained.

Selected Signals: $^1$H NMR (400 MHz; CDCl$_3$) δ 7.58 (d, 1H, J=8.8 Hz); 7.06 (d, 1H, J=8.8 Hz); 6.41 (s, 1H); 4.17 (t, 2H, J=6.0 Hz); 4.09 (s, 2H); 3.68 (t, 2H, J=7.2 Hz); 2.94 (t, 2H, J=7.6 Hz); 2.18 (pentet, 2H, J=7.0 Hz); 1.74 (sextet, 2H, J=7.5 Hz); 1.00 (t, 3H, J=7.4).

EXAMPLE 61

Preparation of 4-(3-{[7-propyl-3-(trifluoromethyl)-1,2-benzisoxazol-6-yl]oxy}propyl)piperazine-2-one.

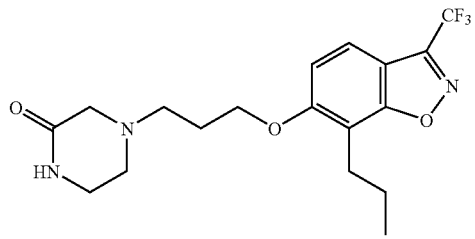

4-(3-{[7-Propyl-3-(trifluoromethyl)-1,2-benzisoxazol-6-yl]oxy}propyl)piperazine-2-one was prepared as for Example 10 from piperazine-2-one and the bromide from Example 7. After aqueous work-up and silica gel chromatography, the title compound was obtained.

Selected Signals: $^1$H NMR (400 MHz; CD$_3$OD) δ 7.64 (d, 1H, J=8.8 Hz); 7.27 (d, 1H, J=8.8 Hz); 4.21 (t, 2H, J=6.0 Hz); 3.85 (s, 1H); 3.71 (t, 2H, J=7.2 Hz); 3.68 (t, 2H, J=5.4 Hz); 2.96 (t, 2H, J=7.6 Hz); 2.16 (pentet, 2H, J=7.0 Hz); 1.73 (sextet, 2H, J=7.5 Hz); 0.98 (t, 3H, J=7.4 Hz).

EXAMPLE 62

Preparation of 3-(3-{[7-propyl-3-(trifluoromethyl)-1,2-benzisoxazol-6-yl]oxy}propyl)-1,3,5-triazinane-2,4-dione.

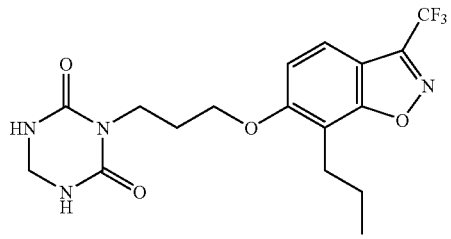

3-(3-{[7-Propyl-3-(trifluoromethyl)-1,2-benzisoxazol-6-yl]oxy}propyl)-1,3,5-triazinane-2,4-dione was prepared as for Example 10 from triazinane-2,4-dione and the bromide from Example 7. After aqueous work-up and silica gel chromatography, the title compound was obtained.

Selected Signals: $^1$H NMR (400 MHz; CDCl$_3$) δ 7.56 (d, 1H, J=8.8 Hz); 7.06 (d, 1H, J=8.8 Hz); 5.7 (s, 2H) 4.54 (t, 2H, J=2.4 Hz); 4.17 (t, 2H, J=6.2 Hz); 3.98 (t, 2H, J=7.0 Hz); 2.96 (t, 2H, J=7.4 Hz); 2.22 (pentet, 2H, J=6.8 Hz); 1.73 (sextet, 2H, J=7.4 Hz); 0.99 (t, 3H, J=7.4 Hz).

EXAMPLE 63

Preparation of 3-(3-{[7-propyl-3-(phenyl)-1,2-benzisoxazol-6-yl]oxy}propyl)-dihydropyrimidine-2,4(1H,3H)-dione.

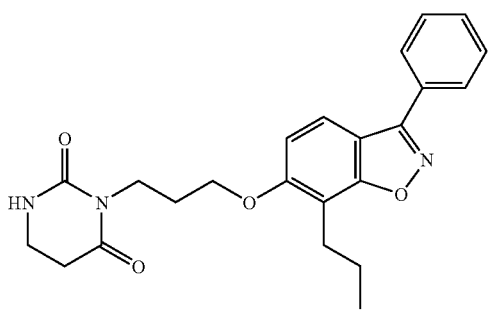

3-(3-{[7-Propyl-3-(phenyl)-1,2-benzisoxazol-6-yl]oxy}propyl)dihydropyrimidine-2,4(1H,3H)-dione was prepared as for Example 10 from dihydropyrimidine-2,4(1H,3H)-dione and the bromide from Example 27. After aqueous work-up and silica gel chromatography, the title compound was obtained.

Selected Signals: $^1$H NMR (400 MHz, CDCl$_3$) δ 7.96–7.94 (m, 2H); 7.66 (d, 1H, J=8.8 Hz); 7.58–7.53 (m, 3H); 6.99 (d, 1H J=8.8 Hz); 5.87 (s, 1H); 4.14 (t, 2H, J=6.2 Hz); 4.04 (t, 2H, J=7.2 Hz); 3.40 (td, 2H, J$_1$=7.0 Hz, J$_2$=2.5 Hz); 2.98 (t, 2H, J=7.6 Hz); 2.74 (t, 2H, J=6.8 Hz); 2.16 (pentet, 2H, J=7.0 Hz); 1.77 (sextet, H, J=7.6 Hz); 1.02 (t, 3H, J=7.4 Hz).

EXAMPLE 64

Preparation of 6-methyl-3-(3-{[7-propyl-3-(trifluoromethyl)-1,2-benzisoxazol-6-yl]oxy}propyl)dihydropyrimidine-2,4(1H,3H)-dione.

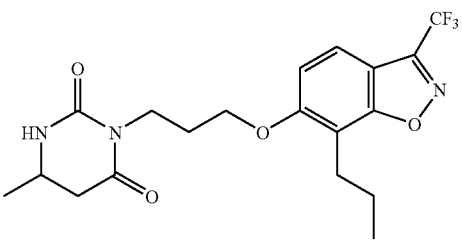

6-Methyl-3-(3-{[7-propyl-3-(trifluoromethyl)-1,2-benzisoxazol-6-yl]oxy}propyl)dihydropyrimidine-2,4(1H,3H)-dione was prepared as for Example 10 from 6-methyldihydropyrimidine-2,4(1H,3H)-dione and the bromide from Example 7. After aqueous work-up and silica gel chromatography, the title compound was obtained.

Selected Signals: $^1$H NMR (400 MHz; CDCl$_3$) δ 7.55 (d, 1H, J=8.8 Hz), 7.05 (d, 1H, J=8.8 Hz), 4.14 (t, 2H, J=6.2 Hz), 4.02 (clean nine line pattern, 2H, J=7.1 Hz), 3.72 (m, 1H), 2.96 (collapsed dd, 2H, J=7.5 Hz), 2.76 (ddd, B of ABX, 1H, J=16.4, 4.0, 1.6 Hz), 2.47 (dd, A of ABX, 1H, J=16.4, 10.4 Hz), 2.16 (pent, 2H, J=6.8 Hz), 1.73 (sext, 2H, J=7.6 Hz), 1.29 (d, 3H, J=6.4 Hz), 0.994 (t, 3H, J=7.4 Hz).

EXAMPLE 65

Preparation of 1-(3-{[7-Propyl-3-(trifluoromethyl)-1,2-benzisoxazol-6-yl]oxy}propyl)azepan-2-one.

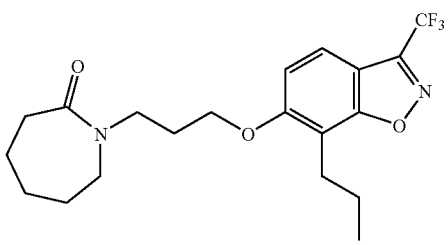

1-(3-{[7-Propyl-3-(trifluoromethyl)-1,2-benzisoxazol-6-yl]oxy}propyl)azepan-2-one was prepared as for Example 10 from caprolactam and the bromide from Example 7. After aqueous work-up and silica gel chromatography, the title compound was obtained.

Characteristic NMR Resonances; $^1$H NMR 400 MHz (CDCl$_3$); δ 7.57 (d, 1H, J=8.8 Hz); 7.07 (d, 1H, J=8.8 Hz); 4.13 (t, 2H, J=6.4 Hz); 3.63 (t, 2H, J=7.2 Hz); 3.45–3.43 (m, 2H); 2.93 (t, 2H, J=7.6 Hz); 2.60–2.57 (m, 2H); 2.12 (pentet, 2H, J=7.0 Hz); 1.77–1.67 (m, 8H); 0.99 (t, 3H, J=7.4 Hz).

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the active agents used in the instant invention as indicated above. Likewise, the specific pharmacological responses observed may vary according to and depending upon the particular active compound selected or whether there are present pharmaceutical carriers, as well as the type of formulation employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:
1. A compound of formula I

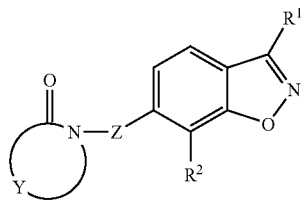

or a pharmaceutically acceptable salt, ester or tautomer thereof, wherein

R$^1$ is selected from the group consisting of:
(a) —CF$_3$,
(b) —CH$_2$C(CH$_3$)$_3$,
(c) phenyl, unsubstituted, mono- or poly-substituted with halo,
(d) —C$_{1-6}$ alkyl, and
(e) —C$_{1-2}$alkyl-phenyl;

R$^2$ is selected from the group consisting of:
(a) —C$_{1-6}$ alkyl,
(b) —COOR$^3$,
(c) —CR$^3$R$^4$—O—R$^5$,
(d) —CR$^3$R$^4$—S—R$^5$, and
(e) —COR$^3$;

R$^3$, R$^4$ and R$^5$ are independently selected at each occurrence from the group consisting of —H, phenyl, and C$_{1-6}$ alkyl;

Y is joined together with the nitrogen and the carbonyl carbon shown in Formula I to which Y is respectively attached, to form a heterocyclic ring selected from:
(a) a 5-membered heterocyclic ring selected from the group consisting of:

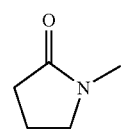
(i)

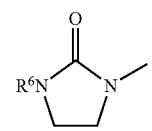
(ii)

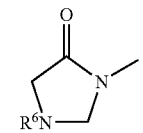
(iii)

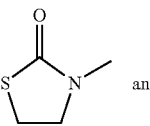
(iv)
and

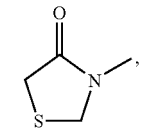
(v)

(b) a 6-membered heterocyclic ring selected from the group consisting of:

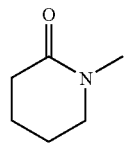
(i)

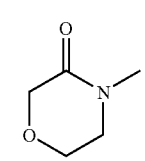
(ii)

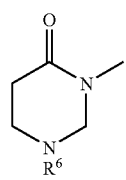 (iii)

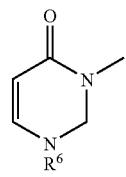 (iv)

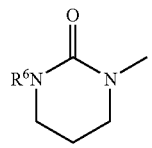 (v)

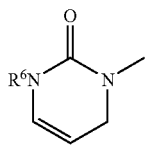 (vi)

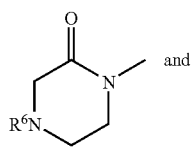 (vii)

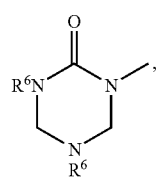 and (viii)

provided that when $R_1$ is —$CF_3$, $R_2$ is n-propyl, and Z is n-propyloxy, the 6-membered heterocyclic ring is not unsubstituted 5,6 dihydrouracil,

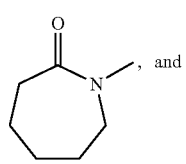 (c)

(d) a bicyclic heterocyclic ring selected from the group consisting of:

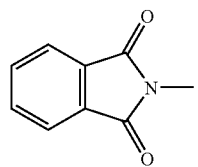 (i)

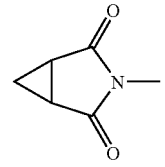 (ii)

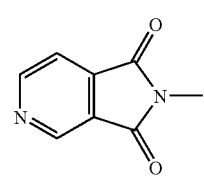 (iii)

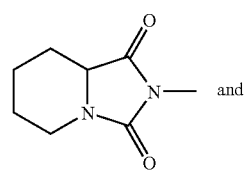 and (iv)

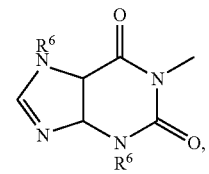 (v)

wherein each carbon atom in the heterocyclic ring, formed when Y is joined together with the nitrogen and the carbonyl carbon shown in Formula I, is independently unsubstituted, mono- or di-substituted with a substituent independently selected at each occurrence from $R^7$;

$R^6$ is independently selected at each occurrence from the group consisting of:
 (a) —H,
 (b) —$C_{1-6}$alkyl, unsubstituted, mono- or poly-substituted with a substituent selected from the group consisting of halo, —OH, —$NR^3R^4$, —$OR^3$, —$COOR^3$, and —CN,
 (c) —$C_{1-6}$alkyl-phenyl, unsubstituted, mono- or poly-substituted with a substituent selected from the group consisting of halo, —$C_{1-3}$alkyl, and —$COOR^3$,
 (d) —$C_{3-6}$cycloalkyl, unsubstituted, mono- or poly-substituted with a substituent selected from the group consisting of halo, —OH, —$OR^3$, —$COOR^3$, and —CN,
 (e) —$C_{3-6}$cycloheteroalkyl, unsubstituted, mono- or poly-substituted with a substituent selected from the group consisting of halo, —OH, —$(CH_2)_nOR^3$, —$OR^3$, —$COOR^3$, and —CN, wherein n is an integer selected from 2, 3, 4, 5 and 6,
 (f) —$C_{2-6}$alkenyl,
 (g) —$C(O)C_{1-6}$alkyl,
 (h) —$COOR^3$,
 (i) —$C(O)$—$(CH_2)_p$—$COOR^3$, wherein p is an integer selected from 2, 3 and 4, (j) phenyl, unsubstituted, mono- or poly-substituted with a substituent selected from the group consisting of halo, —$C_{1-3}$alkyl, and —$COOR^3$, (k) pyridyl, unsubstituted, mono- or poly-substituted with a substituent selected from the group consisting of halo, —$C_{1-3}$alkyl, and —$COOR^3$, (l) pyrimidinyl, unsubstituted, mono- or poly-substituted with a substituent selected from the group consisting of halo, —$C_{1-3}$alkyl, and —$COOR^3$, (m) pyrazinyl, unsubstituted, mono- or poly-substituted with a substituent selected from the group consisting of halo, —$C_{1-3}$alkyl, and —$COOR^3$, and (n) thiazolyl, unsubstituted, mono- or poly-substituted with a substituent selected from the group consisting of halo, —$C_{1-3}$alkyl, and —$COOR^3$;

$R^7$ is independently selected at each occurrence from the group consisting of:
(a) =O,
(b) —$C_{1-6}$alkyl-phenyl, unsubstituted, mono- or poly-substituted with a substituent selected from the group consisting of halo, —CN, —$COOR^3$, —$COR^3$, and —OH,
(c) —$C_{1-6}$alkyl, unsubstituted, mono- or poly-substituted with a substituent selected from the group consisting of halo, —OH, —$COOR^3$, tetrazole and —CN,
(d) —$C_{3-6}$ cycloalkyl,
(e) —$C_{3-6}$ spiroalkyl,
(f) —$COOR^3$,
(g) halo,
(h) —$NR^3R^4$,
(i) phenyl, unsubstituted, mono- or poly-substituted with a substituent selected from the group consisting of halo, —$COOR^3$ and —$C_{1-4}$alkyl,
(j) pyridyl, unsubstituted, mono- or poly-substituted with a substituent selected from the group consisting of halo, —$C_{1-3}$alkyl, and —$COOR^3$,
(k) pyrimidinyl, unsubstituted, mono- or poly-substituted with a substituent selected from the group consisting of halo, —$C_{1-3}$alkyl, and —$COOR^3$, and
(l) pyrazinyl, unsubstituted, mono- or poly-substituted with a substituent selected from the group consisting of halo, —$C_{1-3}$alkyl, and —$COOR^3$; and Z is selected from the group consisting of:
(a) —$C_{1-6}$alkyl-,
(b) —$C_{1-6}$alkyl-O—,
(c) —$C_{3-6}$cycloalkyl-, and
(d) —$C_{3-6}$cycloalkyl-O—;

and wherein the pharmaceutically acceptable ester of the compound of formula I is selected from the group consisting of (a) a phenyl ester, (b) a —$C_{1-6}$alkyl ester and (c) a substituted $C_{1-4}$alkyl ester wherein the substituent is selected from the group consisting of phenyl-, dimethylamino- and acetylamino-.

2. The compound of claim 1 wherein Z is —$C_{2-4}$alkyl-O—.

3. The compound of claim 2 wherein $R^1$ is selected from the group consisting of:
(a) —$CF_3$,
(b) —$CH_2C(CH_3)_3$, and
(c) phenyl, unsubstituted, mono- or poly-substituted with halo; and $R^2$ is selected from the group consisting of:
(a) —$C_{1-6}$ alkyl, and
(b) —$COR^3$.

4. The compound of claim 3 wherein $R^2$ is n-propyl.

5. The compound of claim 4 wherein Y is joined together with the nitrogen and the carbonyl carbon shown in Formula I to which Y is respectively attached, to form a heterocyclic ring selected from:

(a) a 5-membered heterocyclic ring selected from the group consisting of:

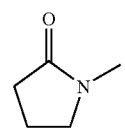

(i)

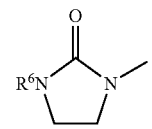

(ii)

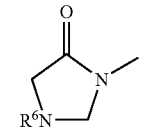

(iii)

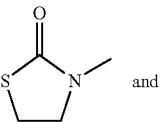

and (iv)

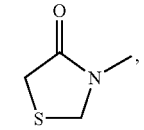

(v)

(b) a 6-membered heterocyclic ring selected from the group consisting of:

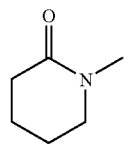

(i)

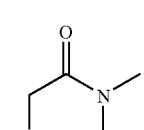

(ii)

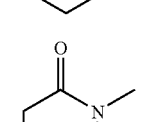

(iii)

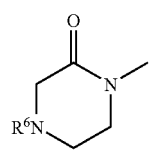

(iv)

-continued

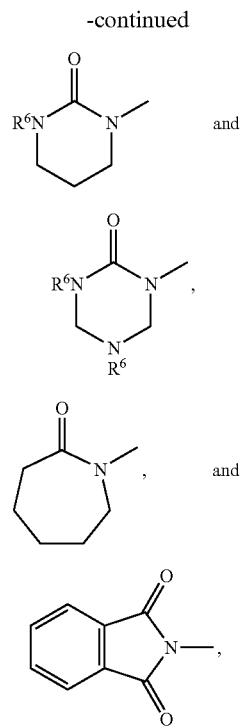

wherein each carbon atom in the heterocyclic ring, formed when Y is joined together with the nitrogen and the carbonyl carbon shown in Formula I, is independently unsubstituted, mono- or di-substituted with a substituent independently selected at each occurrence from $R^7$.

6. The compound of claim 5 wherein $R^6$ is independently selected at each occurrence from the group consisting of:
(a) —H,
(b) —$C_{1-6}$alkyl, unsubstituted, mono- or poly-substituted with a substituent selected from the group consisting of halo, —OH, —$NR^3R^4$, —$OR^3$, —$COOR^3$, and —CN,
(c) —$C_{1-6}$alkyl-phenyl, unsubstituted, mono- or poly-substituted with a substituent selected from the group consisting of halo, —$C_{1-3}$alkyl, and —$COOR^3$,
(d) —C(O)—$(CH_2)_p$—$COOR^3$, wherein p is an integer selected from 2, 3 and 4,
(e) phenyl, unsubstituted, mono- or poly-substituted with a substituent selected from the group consisting of halo, —$C_{1-3}$alkyl, and —$COOR^3$,
(f) pyridyl, unsubstituted, mono- or poly-substituted with a substituent selected from the group consisting of halo, —$C_{1-3}$alkyl, and —$COOR^3$, and
(g) pyrimidinyl, unsubstituted, mono- or poly-substituted with a substituent selected from the group consisting of halo, —$C_{1-3}$alkyl, and —$COOR^3$.

7. The compound of claim 6 wherein $R^7$ is independently selected from the group consisting of:
(a) =O,
(b) —$CH_2$-phenyl, unsubstituted, mono- or poly-substituted with a substituent selected from the group consisting of halo, —CN, —$COOR^3$, —$COR^3$, and —OH,
(c) —$C_{1-6}$alkyl, unsubstituted, mono- or poly-substituted with a substituent selected from the group consisting of halo, —OH, —$COOR^3$, tetrazole and —CN,
(d) halo,
(e) —$NH_2$,
(f) phenyl, unsubstituted, mono- or poly-substituted with a substituent selected from the group consisting of halo, —$COOR^3$ and —$C_{1-4}$alkyl, and
(g) pyridyl, unsubstituted, mono- or poly-substituted with a substituent selected from the group consisting of halo, —$C_{1-3}$alkyl, and —$COOR^3$.

8. The compound of claim 2 wherein $R^1$ is selected from the group consisting of:
(a) —$CF_3$, and
(b) phenyl, unsubstituted, mono- or poly-substituted with halo.

9. The compound of claim 8 wherein Y is joined together with the nitrogen and the carbonyl carbon shown in Formula I to which Y is respectively attached, to form a heterocyclic ring selected from:
(a) a 5-membered heterocyclic ring selected from the group consisting of:

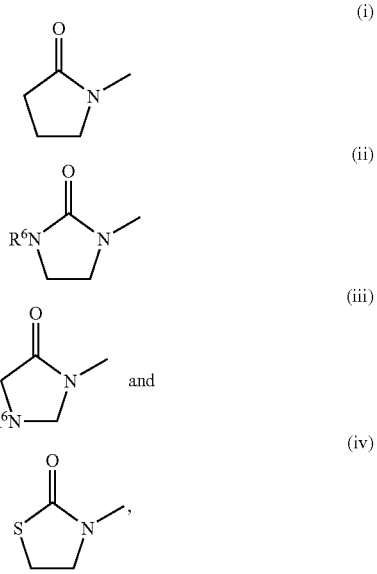

(b) a 6-membered heterocyclic ring selected from the group consisting of:

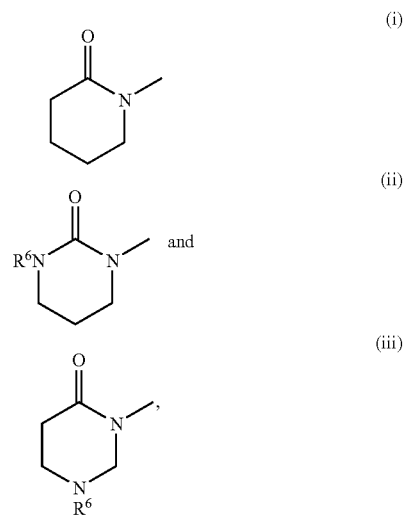

-continued

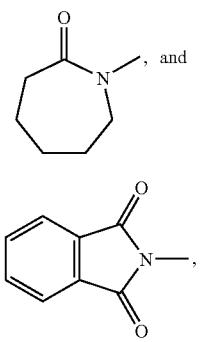
(c) and

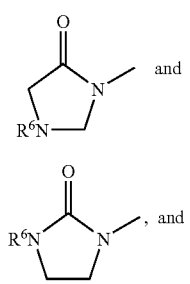
(d)

wherein each carbon atom in the heterocyclic ring, formed when Y is joined together with the nitrogen and the carbonyl carbon shown in Formula I, is independently unsubstituted, mono- or di-substituted with a substituent independently selected at each occurrence from $R^7$.

10. The compound of claim 2 wherein $R^1$ is —$CF_3$.

11. The compound of claim 10 wherein Y is joined together with the nitrogen and the carbonyl carbon shown in Formula I to which Y is respectively attached, to form a heterocyclic ring selected from:

(a) a 5-membered heterocyclic ring selected from the group consisting of:

(i) and (ii) , (b) a 6-membered heterocyclic ring selected from the group consisting of:

(i) and

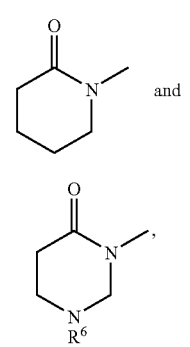
(ii)

wherein each carbon atom in the heterocyclic ring, formed when Y is joined together with the nitrogen and the carbonyl carbon shown in Formula I, is independently unsubstituted, mono- or di-substituted with a substituent independently selected at each occurrence from $R^7$.

12. The compound of claim 1 wherein Z is —$C_{3-6}$cycloalkyl-O—.

13. The compound of claim 1 wherein Z is —$C_{4-6}$alkyl-.

14. A compound selected from the group consisting of:
(1) 1-(3-{[7-propyl-3-(neopentyl)-1,2-benzisoxazol-6-yl]oxy}propyl)pyrrolidine-2,5-dione;
(2) 1-(3-{[7-propyl-3-(trifluoromethyl)-1,2-benzisoxazol-6-yl]oxy}propyl)pyrrolidine-2,5-dione;
(3) 2-(3-{[7-propyl-3-(trifluoromethyl)-1,2-benzisoxazol-6-yl]oxy}propyl)-1H-isoindole-1,3(2H)-dione;
(4) 3,3-dimethyl-1-(3-{[7-propyl-3-(trifluoromethyl)-1,2-benzisoxazol-6-yl]oxy}propyl)pyrrolidine-2,5-dione;
(5) 3-methyl-3-phenyl-1-(3-{[7-propyl-3-(trifluoromethyl)-1,2-benzisoxazol-6-yl]oxy}propyl)pyrrolidine-2,5-dione;
(6) 3-(3-{[7-propyl-3-(neopentyl)-1,2-benzisoxazol-6-yl]oxy}propyl)thiazolidine-2,4-dione;
(7) 3-(3-{[7-propyl-3-(trifluoromethyl)-1,2-benzisoxazol-6-yl]oxy}propyl)thiazolidine-2,4-dione;
(8) 5,5-dimethyl-3-(3-{[7-propyl-3-(neopentyl)-1,2-benzisoxazol-6-yl]oxy}propyl)thiazolidine-2,4-dione;
(9) [2,4-dioxo-3-(3-{[7-propyl-3-(neopentyl)-1,2-benzisoxazol-6-yl]oxy}propyl)-1,3-thiazolidin-5-yl]acetic acid;
(10) 3-(3-{[7-propyl-3-(neopentyl)-1,2-benzisoxazol-6-yl]oxy}propyl)imidazolidine-2,4-dione;
(11) 3-(3-{[7-propyl-3-(trifluoromethyl)-1,2-benzisoxazol-6-yl]oxy}propyl)imidazolidine-2,4-dione;
(12) 1-methyl-3-(3-{[7-propyl-3-(trifluoromethyl)-1,2-benzisoxazol-6-yl]oxy}propyl)imidazolidine-2,4-dione;
(13) 5(R)-methyl-3-(3-{[7-propyl-3-(trifluoromethyl)-1,2-benzisoxazol-6-yl]oxy}propyl)imidazolidine-2,4-dione;
(14) 5,5-dimethyl-3-(3-{[7-propyl-3-(trifluoromethyl)-1,2-benzisoxazol-6-yl]oxy}propyl)imidazolidine-2,4-dione;
(15) 1-(2-pyridyl)-3-(3-{[7-propyl-3-(trifluoromethyl)-1,2-benzisoxazol-6-yl]oxy}propyl)imidazolidine-2,4-dione;
(16) 5-methyl-5-phenyl-3-(3-{[7-propyl-3-(trifluoromethyl)-1,2-benzisoxazol-6-yl]oxy}propyl)imidazolidine-2,4-dione;
(17) 5-methyl-5-phenyl-3-(3-{[7-propyl-3-(neopentyl)-1,2-benzisoxazol-6-yl]oxy}propyl)imidazolidine-2,4-dione;
(18) 5-methyl-5-phenyl-3-(3-{[7-propyl-3-(phenyl)-1,2-benzisoxazol-6-yl]oxy}propyl)imidazolidine-2,4-dione;
(19) 5-methyl-5-phenyl-3-(3-{[7-propyl-3-(trifluoromethyl)-1,2-benzisoxazol-6-yl]oxy}butyl)imidazolidine-2,4-dione;
(20) 5-methyl-5-(3-carboxyphenyl)-3-(3-{[7-propyl-3-(trifluoromethyl)-1,2-benzisoxazol-6-yl]oxy}propyl)imidazolidine-2,4-dione;
(21) 5-methyl-5-(4-pyridyl)-3-(3-{[7-propyl-3-(trifluoromethyl)-1,2-benzisoxazol-6-yl]oxy}propyl)imidazolidine-2,4-dione;
(22) 5-methyl-5-(3-pyridyl)-3-(3-{[7-propyl-3-(trifluoromethyl)-1,2-benzisoxazol-6-yl]oxy}propyl)imidazolidine-2,4-dione;
(23) 5-methyl-5-(2-pyridyl)-3-(3-{[7-propyl-3-(trifluoromethyl)-1,2-benzisoxazol-6-yl]oxy}propyl)imidazolidine-2,4-dione;
(24) 3-(3-{[7-propyl-3-(trifluoromethyl)-1,2-benzisoxazol-6-yl]oxy}propyl)-1-pyrimidin-2-ylimidazolidine-2,4-dione;

(25) 3-(3-{[7-propyl-3-(trifluoromethyl)-1,2-benzisoxazol-6-yl]oxy}propyl)-1-pyrazin-2-ylimidazolidine-2,4-dione;
(26) 3-[2,5-dioxo-4-phenyl-1-(3-{[7-propyl-3-(trifluoromethyl)-1,2-benzisoxazol-6-yl]oxy}propyl)imidazolidin-4-yl]propanoic acid;
(27) 4-[5,5-dimethyl-2,4-dioxo-3-(3-{[7-propyl-3-(trifluoromethyl)-1,2-benzisoxazol-6-yl]oxy}propyl)imidazolidin-1-yl]butanoic acid;
(28) 4-[5,5-dimethyl-2,4-dioxo-3-(3-{[7-propyl-3-(trifluoromethyl)-1,2-benzisoxazol-6-yl]oxy}propyl)imidazolidin-1-yl]pentanoic acid;
(29) 1-(3-{[7-propyl-3-(trifluoromethyl)-1,2-benzisoxazol-6-yl]oxy}propyl)imidazolidin-2-one;
(30) methyl 2-[2-oxo-3-(3-{[7-propyl-3-(trifluoromethyl)-1,2-benzisoxazol-6-yl]oxy}propyl)imidazolidin-1-yl]propanoate;
(31) 2-[2-oxo-3-(3-{[7-propyl-3-(trifluoromethyl)-1,2-benzisoxazol-6-yl]oxy}propyl)imidazolidin-1-yl]propanoic acid;
(32) 1-(3-{[7-propyl-3-(trifluoromethyl)-1,2-benzisoxazol-6-yl]oxy}propyl)imidazolidine-2,4-dione;
(33) 5,5-dimethyl-1-(3-{[7-propyl-3-(trifluoromethyl)-1,2-benzisoxazol-6-yl]oxy}propyl)imidazolidine-2,4-dione;
(34) 1-[cis-2-{[7-propyl-3-(trifluoromethyl)-1,2-benzisoxazol-6-yl]oxy}cyclohexyl)methyl]dihydropyrimidine-2,4(1H,3H)-dione;
(35) 1-[trans-2-{[7-propyl-3-(trifluoromethyl)-1,2-benzisoxazol-6-yl]oxy}cyclopentyl)methyl]dihydropyrimidine-2,4(1H,3H)-dione;
(36) 1-{4-[7-propyl-3-(trifluoromethyl)-1,2-benzisoxazol-6-yl]butyl}dihydropyrimidine-2,4(1H,3H)-dione;
(37) 5-phenyl-3-(3-{[7-propyl-3-(trifluoromethyl)-1,2-benzisoxazol-6-yl]oxy}propyl)dihydropyrimidine-2,4(1H,3H)-dione;
(38) 6-phenyl-3-(3-{[7-propyl-3-(trifluoromethyl)-1,2-benzisoxazol-6-yl]oxy}propyl)dihydropyrimidine-2,4(1H,3H)-dione;
(39) 5-Methyl-3-(3-{[7-propyl-3-(trifluoromethyl)-1,2-benzisoxazol-6-yl]oxy}propyl)dihydropyrimidine-2,4(1H,3H)-dione;
(40) 1,5-Dimethyl-3-(3-{[7-propyl-3-(trifluoromethyl)-1,2-benzisoxazol-6-yl]oxy}propyl)dihydropyrimidine-2,4(1H,3H)-dione;
(41) 1-phenyl-3-(3-{[7-propyl-3-(trifluoromethyl)-1,2-benzisoxazol-6-yl]oxy}propyl)dihydropyrimidine-2,4(1H,3H)-dione;
(42) 3-(3-{[7-propyl-3-(trifluoromethyl)-1,2-benzisoxazol-6-yl]oxy}propyl)-1-pyridin-2-yldihydropyrimidine-2,4(1H,3H)-dione;
(43) 3-(3-{[7-propyl-3-(trifluoromethyl)-1,2-benzisoxazol-6-yl]oxy}propyl)-5,6-dihydro-2H1,2'-bipyrimidine-2,4(3H)-dione;
(44) 3-(3-{[7-propyl-3-(trifluoromethyl)-1,2-benzisoxazol-6-yl]oxy}propyl)-5,6-dihydro-2H-1,5'-bipyrimidine-2,4(3H)-dione;
(45) 1-(3-{[7-propyl-3-(neopentyl)-1,2-benzisoxazol-6-yl]oxy}propyl)piperidin-2-one;
(46) 1-(3-{[7-propyl-3-(trifluoromethyl)-1,2-benzisoxazol-6-yl]oxy}propyl)piperidin-2-one;
(47) 1-(3-{[7-propyl-3-(trifluoromethyl)-1,2-benzisoxazol-6-yl]oxy}propyl)piperidin-2,6-dione;
(48) 1-(3-{[7-propyl-3-(phenyl)-1,2-benzisoxazol-6-yl]oxy}propyl)piperidin-2,5-dione;
(49) 4-(3-{[7-propyl-3-(trifluoromethyl)-1,2-benzisoxazol-6-yl]oxy}propyl)morpholine-3,5-dione;
(50) 1-(3-{[7-propyl-3-(trifluoromethyl)-1,2-benzisoxazol-6-yl]oxy}propyl)piperazine-2,5-dione;
(51) 4-(3-{[7-propyl-3-(trifluoromethyl)-1,2-benzisoxazol-6-yl]oxy}propyl)piperazine-2-one;
(52) 3-(3-{[7-propyl-3-(trifluoromethyl)-1,2-benzisoxazol-6-yl]oxy}propyl)-1,3,5-triazinane-2,4-dione;
(53) 3-(3-{[7-propyl-3-(phenyl)-1,2-benzisoxazol-6-yl]oxy}propyl)dihydropyrimidine-2,4(1H,3H)-dione;
(54) 6-methyl-3-(3-{[7-propyl-3-(trifluoromethyl)-1,2-benzisoxazol-6-yl]oxy}propyl)dihydropyrimidine-2,4(1H,3H)-dione; and
(55) 1-(3-{[7-propyl-3-(trifluoromethyl)-1,2-benzisoxazol-6-yl]oxy}propyl)azepan-2-one;

and pharmaceutically acceptable salts, esters and tautomers thereof, wherein the pharmaceutically acceptable ester are selected from the group consisting of (a) a phenyl ester, (b) a —$C_{1-6}$alkyl ester and (c) a substituted —$C_{1-4}$alkyl ester wherein the substituent is selected from the group consisting of phenyl-, dimethylamino- and acetylamino-.

15. A method for treating dyslipidemia comprising administering a therapeutically effective amount of a compound of claim 1 to a patient in need thereof.

16. The method of claim 15 wherein the dyslipidemia comprises depressed plasma HDL cholesterol level.

17. A method for treating atherosclerosis comprising administering a therapeutically effective amount of a compound of claim 1 to a patient in need thereof.

18. A pharmaceutical composition comprised of a compound of claim 1 and a pharmaceutically acceptable carrier.

19. A compound selected from the group consisting of:
(1) 11-(3-{[7-propyl-3-(trifluoromethyl)-1,2-benzisoxazol-6-yl]oxy}propyl)imidazolidin-2-one;
(2) 1-(3-{[7-propyl-3-(trifluoromethyl)-1,2-benzisoxazol-6-yl]oxy}propyl)pyrrolidine-2,5-dione;
(3) 3-(3-{[7-propyl-3-(trifluoromethyl)-1,2-benzisoxazol-6-yl]oxy}propyl)thiazolidine-2,4-dione;
(4) 3-(3-{[7-propyl-3-(trifluoromethyl)-1,2-benzisoxazol-6-yl]oxy}propyl)imidazolidine-2,4-dione;
(5) 1-Methyl-3-(3-{[7-propyl-3-(trifluoromethyl)-1,2-benzisoxazol-6-yl]oxy}propyl)imidazolidine-2,4-dione;
(6) 5,5-dimethyl-3-(3-{[7-propyl-3-(trifluoromethyl)-1,2-benzisoxazol-6-yl]oxy}propyl)imidazolidine-2,4-dione;
(7) 1-Phenyl-3-(3-{[7-propyl-3-(trifluoromethyl)-1,2-benzisoxazol-6-yl]oxy}propyl)imidazolidine-2,4-dione;
(8) 1-(2-pyridyl)-3-(3-{[7-propyl-3-(trifluoromethyl)-1,2-benzisoxazol-6-yl]oxy}propyl)imidazolidine-2,4-dione;
(9) 5-Phenyl-5-methyl-3-(3-{[7-propyl-3-(trifluoromethyl)-1,2-benzisoxazol-6-yl]oxy}propyl)imidazolidine-2,4-dione;
(10) 5-Phenyl-5-methyl-3-(3-{[7-propyl-3-(trifluoromethyl)-1,2-benzisoxazol-6-yl]oxy}butyl)imidazolidine-2,4-dione;
(11) 5-Phenyl-5-methyl-3-(3-{[7-propyl-3-(phenyl)-1,2-benzisoxazol-6-yl]oxy}propyl)imidazolidine-2,4-dione;
(12) 5-(3-carboxyphenyl)-5-methyl-3-(3-{[7-propyl-3-(trifluoromethyl)-1,2-benzisoxazol-6-yl]oxy}propyl)imidazolidine-2,4-dione;
(13) 5-(2-Pyridyl)-5-methyl-3-(3-{[7-propyl-3-(trifluoromethyl)-1,2-benzisoxazol-6-yl]oxy}propyl)imidazolidine-2,4-dione;

(14) 5-Phenyl-5-(3-propionyl)-3-(3-{[7-propyl-3-(trifluoromethyl)-1,2-benzisoxazol-6-yl]oxy}propyl)imidazolidine-2,4-dione;
(15) 2-[2-oxo-3-(3-{[7-propyl-3-(trifluoromethyl)-1,2-benzisoxazol-6-yl]oxy}propyl)imidazolidin-1-yl]propanoic acid;
(16) 1-(3-{[7-propyl-3-(trifluoromethyl)-1,2-benzisoxazol-6-yl]oxy}propyl)piperidin-2-one;
(17) 1-(3-{[7-propyl-3-(trifluoromethyl)-1,2-benzisoxazol-6-yl]oxy}propyl)piperidin-2,6-dione;
(18) 1-(3-{[7-propyl-3-(phenyl)-1,2-benzisoxazol-6-yl]oxy}propyl)piperidin-2,5-dione;
(19) 1-[cis-2-{[7-propyl-3-(trifluoromethyl)-1,2-benzisoxazol-6-yl]oxy}cyclohexyl)methyl]dihydropyrimidine-2,4(1H,3H)-dione;
(20) 3-(3-{[7-propyl-3-(phenyl)-1,2-benzisoxazol-6-yl]oxy}propyl)-dihydropyrimidine-2,4(1H,3H)-dione;
(21) 6-phenyl-3-(3-{[7-propyl-3-(trifluoromethyl)-1,2-benzisoxazol-6-yl]oxy}propyl)dihydropyrimidine-2,4(1H,3H)-dione;
(22) 1-phenyl-3-(3-{[7-propyl-3-(trifluoromethyl)-1,2-benzisoxazol-6-yl]oxy}propyl)dihydropyrimidine-2,4(1H,3H)-dione;
(23) 3-(3-{[7-propyl-3-(trifluoromethyl)-1,2-benzisoxazol-6-yl]oxy}propyl)-1-pyridin-2-yldihydropyrimidine-2,4(1H,3H)-dione;
(24) 3-(3-{[7-propyl-3-(trifluoromethyl)-1,2-benzisoxazol-6-yl]oxy}propyl)-5,6-dihydro-2H-1,2'-bipyrimidine-2,4(3H)-dione; and
(25) 1-(3-{[7-propyl-3-(trifluoromethyl)-1,2-benzisoxazol-6-yl]oxy}propyl)azepan-2-one, and pharmaceutically acceptable salts, esters and tautomers thereof, wherein the pharmaceutically acceptable ester are selected from the group consisting of (a) a phenyl ester, (b) a —$C_{1-6}$alkyl ester and (c) a substituted —$C_{1-4}$alkyl ester wherein the substituent is selected from the group consisting of phenyl-, dimethylamino- and acetylamino-.

* * * * *